US007456197B2

(12) United States Patent
Balaban et al.

(10) Patent No.: US 7,456,197 B2
(45) Date of Patent: Nov. 25, 2008

(54) PYRIDINIUM CATIONIC LIPIDS AS GENE TRANSFER AGENTS

(75) Inventors: Alexandru T. Balaban, Galveston, TX (US); William A. Seitz, Dickinson, TX (US); Marc A. C. Ilies, Philadelphia, PA (US); Edward Bradbridge Thompson, Galveston, TX (US); Robert E. Garfield, Galveston, TX (US); Betty H. Johnson, Beaumont, TX (US); Aaron L. Miller, Galveston, TX (US); Melissa J. Wentz, Pearland, TX (US)

(73) Assignee: The Texas A&M University System, College Station, TX (US)

( * ) Notice: Subject to any disclaimer, the term of this patent is extended or adjusted under 35 U.S.C. 154(b) by 307 days.

(21) Appl. No.: 10/882,667

(22) Filed: Jul. 1, 2004

(65) Prior Publication Data

US 2005/0196863 A1   Sep. 8, 2005

Related U.S. Application Data

(60) Provisional application No. 60/484,210, filed on Jul. 1, 2003.

(51) Int. Cl.
*C07D 401/02* (2006.01)
*C12N 15/85* (2006.01)
(52) U.S. Cl. ............... 514/318; 546/255; 546/268.1; 546/347; 435/455; 514/317; 514/358
(58) Field of Classification Search ............... 546/347; 514/358
See application file for complete search history.

(56) References Cited

U.S. PATENT DOCUMENTS 6,020,202 A * 2/2000 Jessee .................. 435/458

OTHER PUBLICATIONS

Abstract: Symposium of Structural Biology 2002; poster; "*Heterocyclic Cationic Lipids As Gene Transfer Agents*"; Alexandru T. Balaban, Marc Antoniu Ilies, William A. Seitz, Melissa Wentz, and Robert E. Garfield; 2002.
Poster Content: Biophex/Interphex 2002; "*Heterocyclic Cationic Lipids As Gene Transfer Agents*"; Alexandru T. Balaban, Marc Antoniu Ilies, William A. Seitz, Melissa Wentz, and Robert E. Garfield; 2002.
Poster Content: Biophex/Interphex 2002; "*Evaluation of lipoplex delivery systems for gene therapy*"; Fred O. Makori, Betty H. Johnson, Aaron Miller, Alexandru T. Balaban, Marc A. Ilies, and E. Brad Thompson; 2002.
Abstract: 225th American Chemical Society (ACS) National Meeting (lecture in the Division of Medicinal Chemistry kept by Professor A.T. Balaban); "*Heterocyclic Cationic Lipids As Gene Transfer Agents*"; A.T. Balaban, M.A. Ilies, W.A. Seitz, M. Wentz, and R.E. Garfield; 2003.

Presentation Content: 225th American Chemical Society (ACS) National Meeting; lecture in the Division of Medicinal Chemistry by Professor A.T. Balaban; "*Heterocyclic Cationic Lipids As Gene Transfer Agents*"; A.T. Balaban, M.A. Ilies, W.A. Seitz, M. Wentz, and R.E. Garfield; 2003.
Abstract: 227th ACS National Meeting; lecture in the Division of Colloid and Surface Chemistry by Dr. M.A. Ilies; "*Lipophilic pyrylium salts in the synthesis of pyridinium-based cationic lipids and gemini surfactants for gene transfer*"; M.A. Ilies, W.A. Seitz, B.H. Johnson, A. Miller, E.B. Thompson, A.T. Balaban; 2004.
Presentation Content: 227th ACS National Meeting; lecture in the Division of Colloid and Surface Chemistry by Dr. M.A. Ilies; "*Lipophilic pyrylium salts in the synthesis of pyridinium-based cationic lipids and gemini surfactants for gene transfer*"; M.A. Ilies, W.A. Seitz, B.H. Johnson, A. Miller, E.B. Thompson, A.T. Balaban; 2004.
Poster Abstract: 227th ACS National Meeting; "*Structure-activity relationships in a series of pyridinium-based cationic lipids*"; Marc Antoniu Ilies, William A. Seitz, Betty H. Johnson, Aaron Miller, E. Brad Thompson, and Alexandru T. Balaban; 2004.
Poster Content: 227th ACS National Meeting; "*Structure-activity relationships in a series of pyridinium-based cationic lipids*"; Marc Antoniu Ilies, William A. Seitz, Betty H. Johnson, Aaron Miller, E. Brad Thompson, and Alexandru T. Balaban; 2004.
Poster Abstract: American Society of Gene Therapy's 7th Annual Meeting: "*New pyridinium cationic lipids for gene delivery synthesized via pyrylium salts*"; Marc Antoniu Ilies, Betty H. Johnson, William A. Seitz, Ed L. Ezell, Aaron Miller, E. Brad Thompson, and Alexandru T. Balaban; 2004.
Poster Content: American Society of Gene Therapy's 7th Annual Meeting: "*New pyridinium cationic lipids for gene delivery synthesized via pyrylium salts*"; Marc Antoniu Ilies, Betty H. Johnson, William A. Seitz, Ed L. Ezell, Aaron Miller, E. Brad Thompson, and Alexandru T. Balaban; 2004.
Marc Antoniu Ilies, William A. Seitz, Miron T. Caproiu, Melissa Wentz, Robert E. Garfield and Alexandru T. Balaban; "*Pyridinium-Based Cationic Lipids as Gene-Transfer Agents*"; Eur. J. Org. Chem. 2003, 2645-2655.
Marc Antoniu Ilies, William A. Seitz, Ion Ghiviriga, Betty H. Johnson, Aaron Miller, E. Brad Thompson and Alexandru T. Balaban; "*Pyridinium Cationic Lipids in Gene Delivery: A Structure—Activity Correlation Study*"; American Chemical Society, Journal of Medicinal Chemistry; Jan. 6, 2004 (Published on Internet); 11 pgs.
Marc Antoniu Ilies & Alexandru T. Balaban; "*Recent developments in cationic lipid-mediated gene delivery and gene therapy*"; Ashley Publications, 2001; 1729-1752.
Marc Antoniu Ilies, William A. Seitz and Alexandru T. Balaban; "*Cationic Lipids in Gene Delivery: Principles, Vector Design and Therapeutical Applications*"; Current Pharmaceutical Design, Dec. 2002; 2441-2473.

* cited by examiner

Primary Examiner—Zinna N Davis
(74) Attorney, Agent, or Firm—Howrey LLP

(57) ABSTRACT

Pyridinium cationic lipids useful as non-viral gene delivery agents are disclosed. The agents are prepared by reaction of pyrylium salts with primary amines. Also disclosed are methods of trasfectind cells using the pyridinium cationic lipids as gene transfer agents.

16 Claims, 13 Drawing Sheets

3Myr  3Ole

5Myr  5Ole

PYRIDINIUM CATIONIC LIPIDS AS GENE TRANSFER AGENTS

RELATED APPLICATIONS

This application claims the benefit of provisional application Ser. No. 60/484,210, filed Jul. 1, 2003, the entire contents of which is incorporated herein by reference.

FIELD OF THE INVENTION

The invention relates to the fields of molecular biology and chemistry and, more specifically, to methods and reagents for transfecting cells. In particular, pyridinium cationic lipids useful as gene transfer agents are disclosed, along with a method of synthesizing these lipids by reacting pyrylium salts with primary amines.

BACKGROUND OF THE INVENTION

The prospect of gene therapy gives a new perspective to medicine, allowing a revolutionary approach to treat diseases at the level where they are generated, namely the living cell. When the cellular machinery is impaired due to a deficient gene, a functional gene incorporated into an appropriate vector may be delivered to the affected cells, tissues or organs. After internalization, the DNA is transferred to the nucleus where the gene is integrated into the host genome, transcribed and finally translated into the proteins needed to correct the cellular imbalance. Despite the simple concept, the eventual success of this new form of therapy relies on the efficiency of the overall delivery process.

Viral vectors are currently the most efficient systems for the transfer and expression (transfection) of foreign DNA into living cells. However, their effectiveness is hampered by serious side effects, such as immunogenicity, difficulties associated with good manufacturing practice (GMP) production or storage, a limited size of the DNA that can be inserted into the virion, mutagenicity, and sometimes fatal toxicity.

Cationic lipids have emerged as safer alternatives to viral delivery. Having low immunogenicity and cytotoxicity, they also allow the use of plasmids of practically unlimited size and can be easily manufactured and stored in bulk quantities under GMP-compliant norms. In order to bind and compact DNA efficiently, the cationic lipids usually must self-assemble first into cationic liposomes. Under this form they interact with the negatively charged plasmids to yield cationic lipids-DNA complexes (lipoplexes) with differing sizes and shapes. The characteristics of the lipoplexes are essential for their efficiency. Variables such as the lipid nature and composition of the parent cationic liposomes, the characteristics of the plasmid or the method used to generate the lipoplexes are critical for achieving high levels of transfection.

Despite tremendous synthetic efforts that have generated several commercial cationic lipid transfection systems (DOTMA—Di-C14-amidine), there is still a need for improving in vivo efficiency and decreasing cytotoxicity. In this context, the heterocyclic cationic lipids newly introduced by several different groups represent a promising alternative, displaying higher transfection efficiencies and a reduced cytotoxicity when compared with their tetraalkylammonium congeners.

SUMMARY OF THE INVENTION

Accordingly, one aspect of the invention is to provide compounds useful as transfection agents for transfecting cells. One embodiment of the invention is a compound useful as a gene transfer agent, the compound having Formula I:

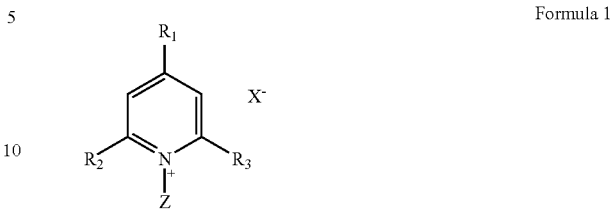

Formula 1 wherein $R^1$ is selected from the group consisting of $C_{1-25}$ alkyl; $C_{1-25}$ alkenyl; $C_{1-25}$ alkynyl; $C_{1-25}$ alkoxy; $C_{1-25}$ alkylaminomethyl; $C_{1-25}$ dialkylaminomethyl; phenyl; phenyl substituted with one or more substitutents selected from the group consisting of $C_{1-5}$ alkyl, $C_{1-5}$ alkenyl, $C_{1-5}$ alkynyl, $C_{1-5}$ alkoxy, and $C_{1-5}$ amino; styryl; and styryl substituted with one or more substitutents selected from the group consisting of $C_{1-25}$ alkyl, $C_{1-25}$ alkenyl, $C_{1-25}$ alkynyl, $C_{1-25}$ alkoxy, and $C_{1-25}$ dialkylamino; $R^2$ and $R^3$ are $C_{1-25}$ alkyl, $C_{1-25}$ alkenyl, or $C_{1-25}$ alkynyl; X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, and wherein Z is selected from the group consisting of:

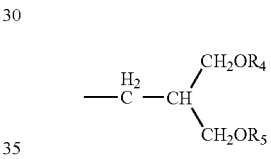

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl;

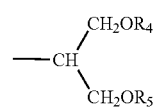

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl;

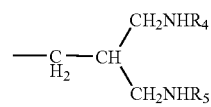

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl;

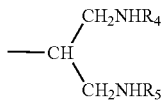

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl;

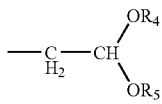

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl;

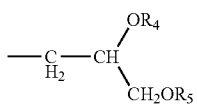

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl;

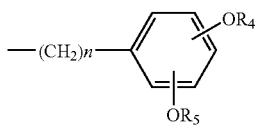

wherein n is 0-25 and $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl;

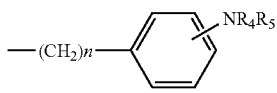

wherein n is 0-25 and $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl;

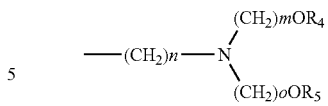

wherein n, m, and o are independently 0-25 and $R_4$ and $R_5$ are independently selected from the group consisting of $C_{1-25}$ alkyl, $C_{1-25}$ alkenyl, $C_{1-25}$ alkynyl, $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl;

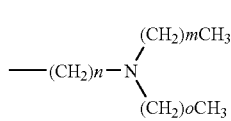

wherein n, m, and o are independently 0-25;

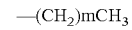

wherein m is 0-25;

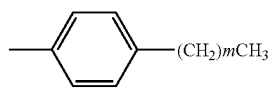

wherein m is 0-25;

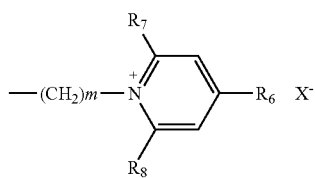

wherein m is 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, and $R_7$ and $R_8$ are independently $C_{1-25}$ alkyl;

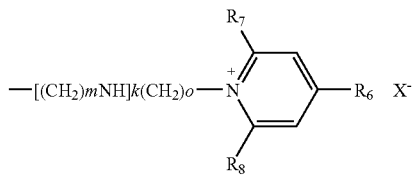

wherein m, k, and o are independently 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, and $R_7$ and $R_8$ are independently $C_{1-25}$ alkyl;

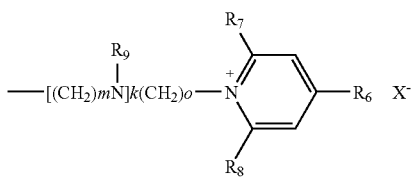

wherein m, k, and o are independently 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, $R_7$ and $R_8$ are independently $C_{1-25}$ alkyl; and $R_9$ is selected from the group consisting of $C_{1-25}$ alkyl, hydroxy $C_{1-25}$ alkyl, amino $C_{1-25}$ alkyl, $C_{1-25}$ alkenyl, $C_{1-25}$ alkynyl, $C_{1-25}$ acyl, hydroxy $C_{1-25}$ acyl, amino $C_{1-25}$ acyl, $C_{1-25}$ alkyloxycarbonyl, t-butyloxycarbonyl, adamantyloxycarbonyl, perfluoro $C_{1-25}$ alkyl; perfluoro $C_{1-25}$ acyl; poly(ethyleneoxy)alkyl, poly(ethyleneoxy)acyl, and cholesteryloxycarbonyl;

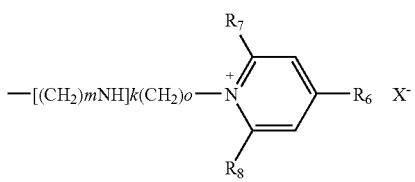

wherein m, k, and o are independently 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, and $R_7$ and $R_8$ are independently $C_{1-25}$ alkyl;

—$(CH_2)mMR_4$ wherein m is 0-25 and M is O, S, or NH and $R_4$ is selected from the group consisting of $C_{1-25}$ alkyl, $C_{1-25}$ alkenyl, $C_{1-25}$ alkynyl, $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl;

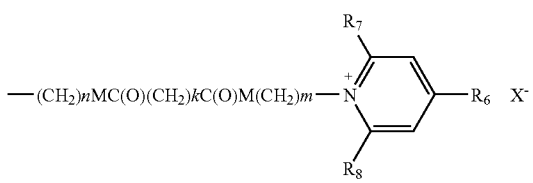

wherein n, m, and k are independently 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, and $R_7$ and $R_8$ are independently $C_{1-25}$ alkyl, and M is O, S, or NH;

—$(CH_2)mSSR_4$ wherein m is 0-25 and $R_4$ is selected from the group consisting of H, $C_{1-25}$ alkyl $C_{1-25}$ alkenyl, $C_{1-25}$ alkynyl, $C_{1-25}$ acyl; and

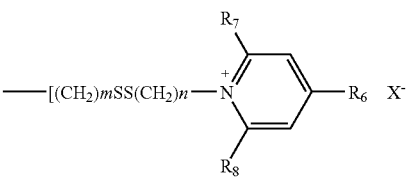

wherein m and n are independently 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, and $R_7$ and $R_8$ are independently $C_{1-25}$ alkyl.

A further aspect of the invention is a method of preparing compounds according to Figure I, by reacting a compound having the formula:

Formula II

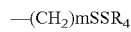

wherein $R^1$ is selected from the group consisting of $C_{1-25}$ alkyl; halogeno $C_{1-25}$ alkyl, $C_{1-25}$ alkenyl; $C_{1-25}$ alkynyl; $C_{1-25}$ alkoxy; $C_{1-25}$ alkylaminomethyl; $C_{1-25}$ dialkylaminomethyl; phenyl; phenyl substituted with one or more substitutents selected from the group consisting of $C_{1-5}$ alkyl, $C_{1-5}$ alkenyl, $C_{1-5}$ alkynyl, $C_{1-5}$ alkoxy, and $C_{1-5}$ amino; styryl; and styryl substituted with one or more substitutents selected from the group consisting of $C_{1-25}$ alkyl, $C_{1-25}$ alkenyl, $C_{1-25}$ alkynyl, $C_{1-25}$ alkoxy, and $C_{-125}$ dialkylamino;

$R^2$ and $R^3$ are $C_{1-25}$ alkyl, $C_{1-25}$ alkenyl, or $C_{1-25}$ alkynyl;

wherein X is selected from the group consisting of halogen, perchlorate, tetrafluoroborate, trifluoromethanesulfonate, sulfoacetate, and hexafluorophosphate;

with a primary amine.

A still further aspect of the invention is a method tranfecting cells by mixing at least one plasmid or polynucleotide with a compound of Formula I and bringing the mixture thus obtained into contact with the cells to be transfected.

DETAILED DESCRIPTION OF THE INVENTION

Figure 1:
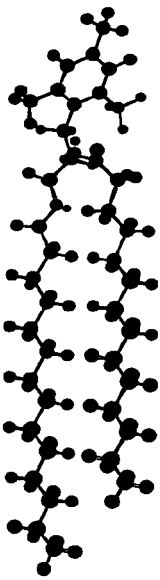
FIGS. 1A and 1B. The structures of representative pyridinium cationic lipids and of tetramethylammonium lipid DOTAP used as reference. The energy minimization was performed with the Chem3DPro software (ChemOffice, CambridgeSoft Corp.) using MM2 molecular mechanics routine towards a 0.001 RMS gradient.
Figure 1:
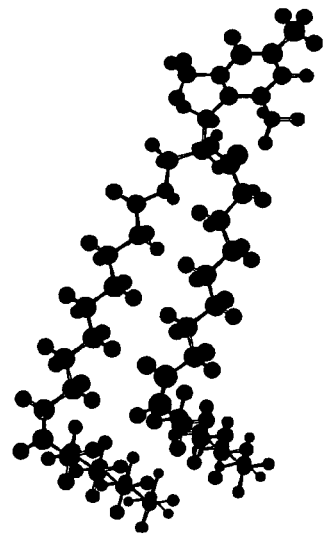
Figure 1:
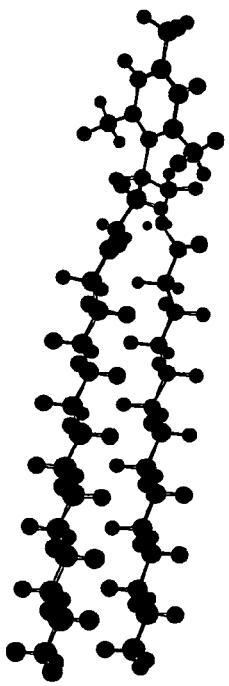
Figure 1:
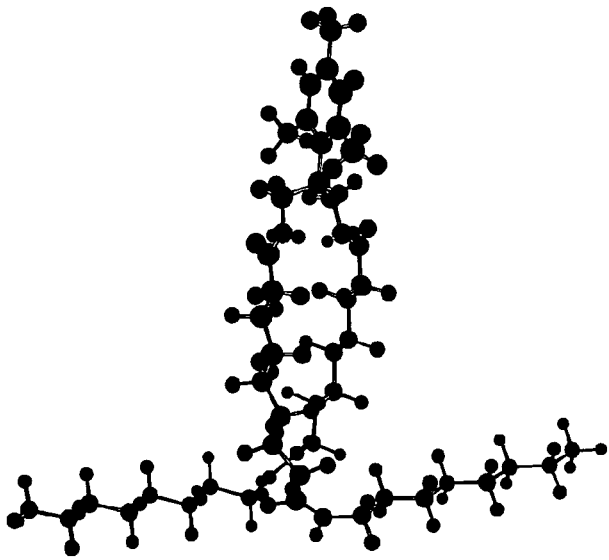
Figure 1B:
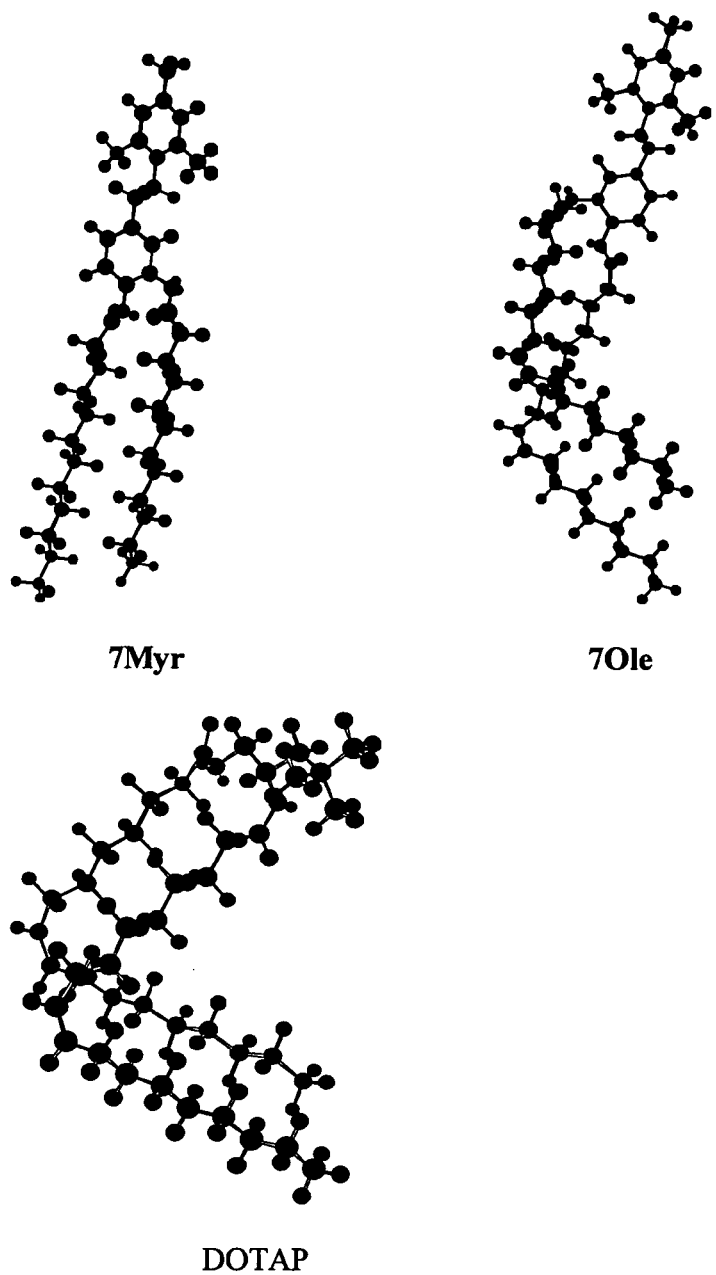

An object of the present invention is to provide compounds useful as transfection agents for transfecting cells. One embodiment of the invention is a compound useful as a gene transfer agent, the compound having Formula I:

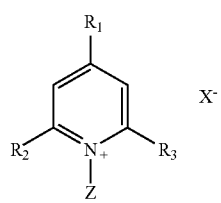

Formula I wherein $R^1$ is selected from the group consisting of $C_{1-25}$ alkyl; $C_{1-25}$ alkenyl; $C_{1-25}$ alkynyl; $C_{1-25}$ alkoxy; $C_{1-25}$ alkylaminomethyl; $C_{1-25}$ dialkylaminomethyl; phenyl; phenyl substituted with one or more substitutents selected from the group consisting of $C_{1-5}$ alkyl, $C_{1-5}$ alkenyl, $C_{1-5}$ alkynyl, $C_{1-5}$ alkoxy, and $C_{1-5}$ amino; styryl; and styryl substituted with one or more substitutents selected from the group consisting of $C_{1-25}$ alkyl, $C_{1-25}$ alkenyl, $C_{1-25}$ alkynyl, $C_{1-25}$ alkoxy, and $C_{1-25}$ dialkylamino; $R^2$ and $R^3$ are $C_{1-25}$ alkyl, $C_{1-25}$ alkenyl, or $C_{1-25}$ alkynyl; and X is selected from the group consisting of halogen, perchlorate, tetrafluoroborate, trifluoromethanesulfonate, sulfoacetate, and hexafluorophosphate. As shown below, various choices of $R_{1-3}$, Z and X provides extreme flexibility in tailoring the transfection agent for a particular application. For example, the particular counter-ion, X, can be selected by balancing the need for effective transfection with the cytotoxicity of the transfection agent. Furthermore, the counterion can be changed, using an anion exchange resin, so other counterions such as halogen, methanesulfonate, p-toluenesulfonate, methosulfate, acetate, trifluoroacetate, or hemisuccinate can be accessed via this approach. As shown below, for example, perchlorate as a counter-ion may provide the most effective transfection, in some cases, but may be too cytotoxic for some applications. According to particular embodiments, hexafluorophosphate or chloride may strike a better balance of cytotoxicity and effectiveness.

The present invention provides extreme flexibility in the choice of the aliphatic portion of lipid, Z. According to one embodiment, Z is selected from the group consisting of:

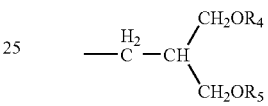

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl. Alternatively, Z is

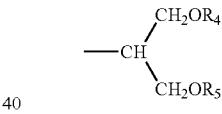

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl. Alternatively, Z is

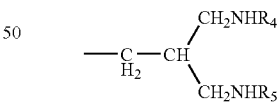

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl. Alternatively, Z is

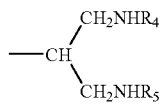

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl. Alternatively, Z is

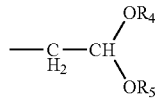

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl. Alternatively, Z is

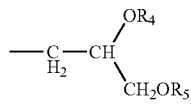

wherein $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl. Alternatively, Z is

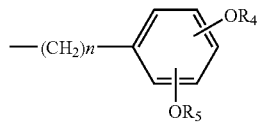

wherein n is 0-25 and $R_4$ and $R_5$ are independently selected from the group consisting of $C_{1-25}$ alkyl, $C_{1-25}$ alkenyl, $C_{1-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl. Alternatively, Z is

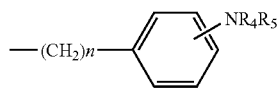

wherein n is 0-25 and $R_4$ and $R_5$ are independently selected from the group consisting of $C_{1-25}$ alkyl, $C_{1-25}$ alkenyl, $C_{1-25}$ alkynyl, $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl. Alternatively, Z is

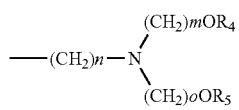

wherein n, m, and o are independently 0-25 and $R_4$ and $R_5$ are independently selected from the group consisting of $C_{1-25}$ alkyl, $C_{1-25}$ alkenyl, $C_{1-25}$ alkynyl, $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl; Alternatively, Z is

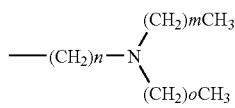

wherein n, m, and o are independently 0-25 Alternatively, Z is

—$(CH_2)mCH_3$ wherein m is 0-25. Alternatively, Z is

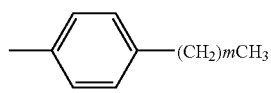

wherein m is 0-25. Alternatively, Z is

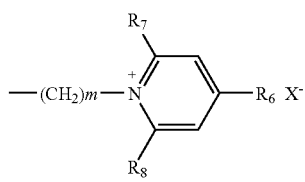

wherein m is 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, and $R_7$ and $R_8$ are independently $C_{1-25}$ alkyl. Alternatively, Z is

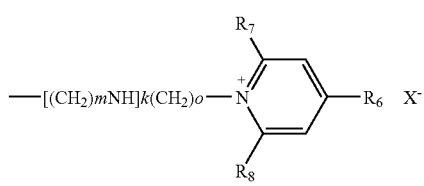

wherein m, k, and o are independently 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, and $R_7$ and $R_8$ are independently $C_{1-25}$ alkyl. Alternatively, Z is

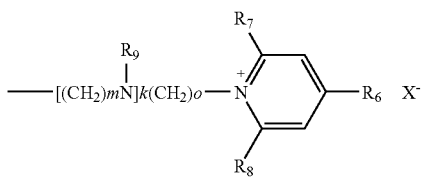

wherein m, k, and o are independently 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, $R_7$ and $R_8$ are independently $C_{1-25}$ alkyl; and $R_9$ is selected from the group consisting of $C_{1-25}$ alkyl, hydroxy $C_{1-25}$ alkyl, amino $C_{1-25}$ alkyl, $C_{1-25}$ alkenyl, $C_{1-25}$ alkynyl, $C_{1-25}$ acyl, hydroxy $C_{1-25}$ acyl, amino $C_{1-25}$ acyl, $C_{1-25}$ alkyloxycarbonyl, t-butyloxycarbonyl, adamantyloxycarbonyl, perfluoro $C_{1-25}$ alkyl; perfluoro $C_{1-25}$ acyl; poly(ethyleneoxy)alkyl, poly(ethyleneoxy)acyl, and cholesteryloxycarbonyl. Alternatively, Z is

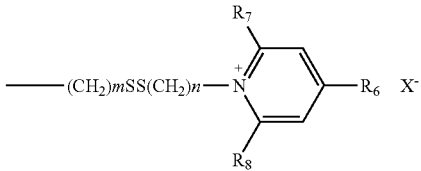

wherein m, k, and o are independently 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, and $R_7$ and $R_8$ are independently $C_{1-25}$ alkyl. Alternatively, Z is —$(CH_2)mMR_4$ wherein m is 0-25 and M is O, S, or NH and $R_4$ is selected from the group consisting of $C_{1-25}$ alkyl, $C_{1-25}$ alkenyl, $C_{1-25}$ alkynyl, $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl. Alternatively, Z is

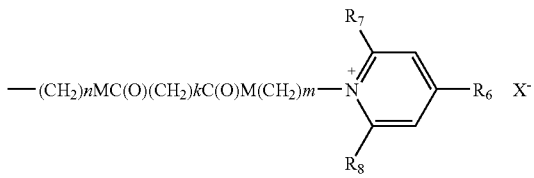

wherein n, m, and k are independently 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, and $R_7$ and $R_8$ are independently $C_{1-25}$ alkyl, and M is O, S, or NH. Alternatively, Z is —$(CH_2)mSSR_4$ wherein m is 0-25 and $R_4$ is selected from the group consisting of H, $C_{1-25}$ alkyl $C_{1-25}$ alkenyl, $C_{1-25}$ alkynyl, $C_{1-25}$ acyl. Alternatively, Z is

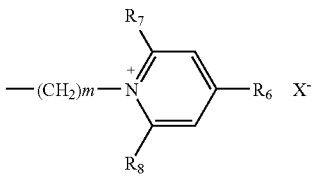

wherein m and n are independently 0-25, X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, $R_6$ is $C_{1-25}$ alkyl, and $R_7$ and $R_8$ are independently $C_{1-25}$ alkyl.

According to a particular embodiment, Z is

—$(CH_2)mCH_3$ wherein m is 14. According to another particular embodiment, Z is

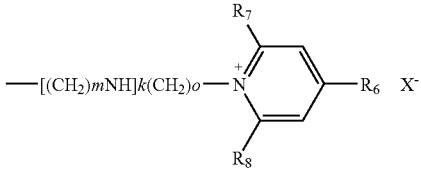

wherein m is 2-8, X is hexafluorophosphate, $R_6$ and $R_7$ are methyl and $R_8$ $C_{14}$ alkyl. According to another particular embodiment m is 2 and $R_8$ is $C_{14}$ alkyl. According to another particular embodiment Z is

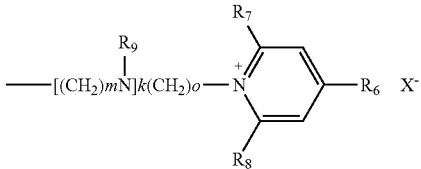

wherein m is 2-4, k is 1 or 2, o is 3, X is hexafluorophosphate, $R_6$ and $R_7$ are methyl and $R_8$ is $C_{14}$ alkyl. According to another particular embodiment Z is

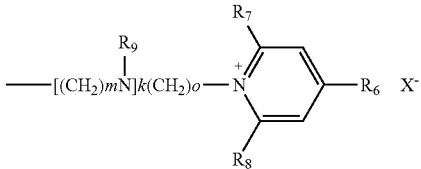

wherein m is 2-4, k is 1 or 2, o is 3, X is hexafluorophosphate $R_6$ and $R_7$ are methyl, $R_8$ is $C_{14}$ alkyl, and $R_9$ is t-butyloxycarbonyl. According to another particular embodiment Z is

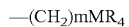

wherein m is 2, M is O or NH, X is hexafluorophosphate and $R_4$ is $C_{1-14}$ acyl.

According to a particular embodiment of the invention, Formula I is selected from the group of compounds consisting of 1-(2,3-dihydroxypropyl)-2,4,6-trimethylpyridinium hexafluorophosphate, 1-(2,3-dilauroyloxypropyl)-2,4,6-trimethylpyridinium hexafluorophosphate, 1-(2,3-dimyristoyloxypropyl)-2,4,6-trimethylpyridinium hexafluorophosphate, 1-(2,3-dipamitoyloxypropyl)-2,4,6-trimethylpyridinium hexafluorophosphate, 1-(2,3-distearoyloxypropyl)-2,4,6-trimethylpyridinium hexafluorophosphate, 1-(2,3-dioleoyloxypropyl)-2,4,6-trimethylpyridinium hexafluorophosphate, 1-(1,3-dihydroxypropane-2-yl)-2,4,6-trimethylpyridinium hexafluorophosphate, 1-(1,3-dilauroyloxypropane-2-yl)-2,4,6-trimethylpyridinium hexafluorophosphate, 1-(1,3-dimyristoyloxypropane-2-yl)-2,4,6-trimethylpyridinium hexafluorophosphate, 1-(1,3-dimyristoyloxypropane-2-yl)-2,4,6-trimethylpyridinium perchlorate, 1-(1,3-dimyristoyloxypropane-2-yl)-2,4,6-trimethylpyridinium tetrafluoroborate, 1-(1,3-dimyristoyloxypropane-2-yl)-2,4,6-trimethylpyridinium chloride, 1-(1,3-dimyristoyloxypropane-2-yl)-2,4,6-trimethylpyridinium iodide, 1-(1,3-dipamitoyloxypropane-2-yl)-2,4,6-trimethylpyridinium hexafluorophosphate, 1-(1,3-distearoyloxypropane-2-yl)-2,4,6-trimethylpyridinium hexafluorophosphate, 1-(1,3-dioleoyloxypropane-2-yl)-2,4,6-trimethylpyridinium hexafluorophosphate, 1-(3,4-dihydroxyphenylethyl)-2,4,6-trimethylpyridinium hexafluorophosphate, 1-(3,4-dioctanoyloxyphenylethyl)-2,4,6-trimethylpyridinium hexafluorophosphate, 1-(3,4-didecanoyloxyphenylethyl)-2,4,6-trimethylpyridinium hexafluorophosphate, 1-(3,4-dilauroyloxyphenylethyl)-2,4,6-trimethylpyridinium hexafluorophosphate, 1-(3,4-dimyristoyloxyphenylethyl)-2,4,6-trimethylpyridinium hexafluorophosphate, 1-(3,4-dipalmitoyloxyphenylethyl)-2,4,6-trimethylpyridinium hexafluorophosphate, 1-(3,4-distearoyloxyphenylethyl)-2,4,6-trimethylpyridinium hexafluorophosphate, and 1-(3,4-dioleoyloxyphenylethyl)-2,4,6-trimethylpyridinium hexafluorophosphate.

A further aspect of the present invention is a method of preparing a compound useful as a gene transfer agent, the method comprising: reacting a compound having the formula:

Formula II

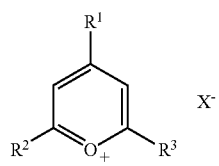

wherein $R^1$ is selected from the group consisting of $C_{1-25}$ alkyl; halogeno $C_{1-25}$ alkyl, $C_{1-25}$ alkenyl; $C_{1-25}$ alkynyl; $C_{1-25}$ alkoxy; $C_{1-25}$ alkylaminomethyl; $C_{1-25}$ dialkylaminomethyl; phenyl; phenyl substituted with one or more substitutents selected from the group consisting of $C_{1-5}$ alkyl, $C_{1-5}$ alkenyl, $C_{1-5}$ alkynyl, $C_{1-5}$ alkoxy, and $C_{1-5}$ amino; styryl; and styryl substituted with one or more substitutents selected from the group consisting of $C_{1-25}$ alkyl, $C_{1-25}$ alkenyl, $C_{1-25}$ alkynyl, $C_{1-25}$ alkoxy, and $C_{1-25}$ dialkylamino; $R^2$ and $R^3$ are $C_{1-25}$ alkyl, $C_{1-25}$ alkenyl, or $C_{1-25}$ alkynyl; wherein X is selected from the group consisting of halogen, perchlorate, tetrafluoroborate, trifluoromethanesulfonate, sulfoacetate, and hexafluorophosphate with a primary amine.

According to one embodiment, the primary amine contains one or more hydroxyl groups and the method further comprises alkylating or acylating the one or more hydroxyl groups. For example, the primary amine may be selected from the group consisting of:

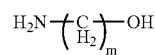

wherein m is 1-25 (formula added)

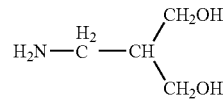

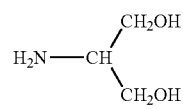

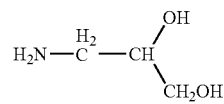

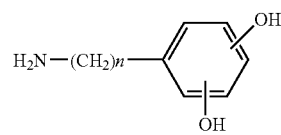

wherein n is 0-25, and

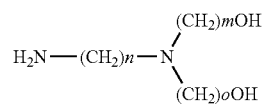

wherein n, m, and o are independently 0-25. The method of preparing the gene transfer agent may further comprise acylating the one or more hydroxyl groups with an acyl halide having the formula $R_4C(O)X$, wherein $R_4$ is selected from the group consisting of $C_{1-25}$ alkyl, $C_{1-25}$ alkenyl, $C_{1-25}$ alkynyl, $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl. Alternatively, the primary amine may comprise one or more hydroxyl groups and the method further comprises forming the tosylate or trifluoromethanesulfonate ester of the one or more hydroxyl groups and reacting the tosylate or trifluoromethanesulfonate ester with an alcohol having the formula $R_4OH$, wherein $R_4$ is selected from the group consisting of $C_{1-25}$ alkyl, $C_{1-25}$ alkenyl, $C_{1-25}$ alkynyl, perfluoro $C_{1-25}$ alkyl, poly(ethyleneoxy)alkyl, in the presence of a strong base such as potassium t-butoxide or sodium hydride.

According to another embodiment, the primary amine contains two or more primary amine groups. According to one embodiment, two equivalents of a compound having Formula II are reacted with a primary amine having two amine groups. According to a particular embodiment, two equivalents of a compound having Formula II are reacted with a primary amine having the formula $NH_2(CH_2)mNH_2$, wherein m is 0-25, to yield a compound having the formula

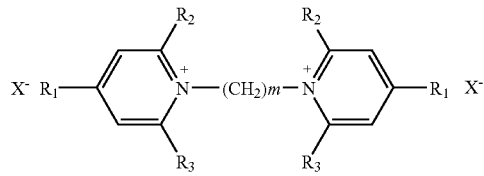

According to another embodiment, two equivalents of a compound having Formula II are reacted with a primary amine having the formula $NH_2[(CH_2)_mNH]_k(CH_2)_oNH_2$, wherein m, k, and o are independently 0-25, to yield a compound having the formula

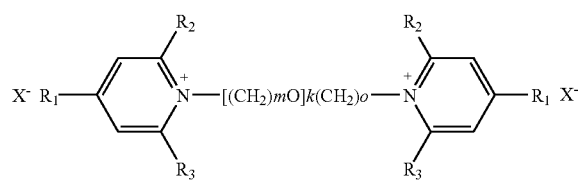

According to another embodiment, two equivalents of a compound having Formula II are reacted with a compound having the formula $NH_2[(CH_2)_mN(R_9)]_k(CH_2)_oNH_2$, wherein m, k, and o are independently 0-25 and $R_9$ is selected from the group consisting of $C_{1-25}$ alkyl, hydroxy $C_{1-25}$ alkyl, amino $C_{1-25}$ alkyl, $C_{1-25}$ alkenyl, $C_{1-25}$ alkynyl, $C_{1-25}$ acyl, hydroxy $C_{1-25}$ acyl, amino $C_{1-25}$ acyl, $C_{1-25}$ alkyloxycarbonyl, t-butyloxycarbonyl, adamantyloxycarbonyl, perfluoro $C_{1-25}$ alkyl; perfluoro $C_{1-25}$ acyl; poly(ethyleneoxy)alkyl, poly(ethyleneoxy)acyl, and cholesteryloxycarbonyl, to yield a compound having the formula

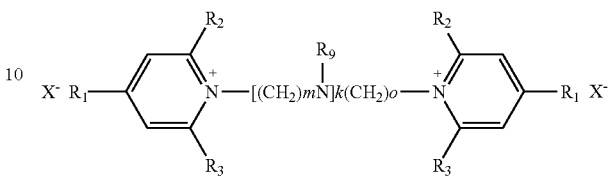

A further aspect of the present invention is a method of transfecting cells comprising mixing at least one plasmid or polynucleotide with a compound of the present invention and bringing the mixture thus obtained into contact with the cells to be transfected. A used herein, the terms plasmid and polynucleotide are broadly construed and may include any nucleotide or genetic material such as DNA, RNA, siRNA, oligonucleotides, and antisense oligonucleotides. An alternative embodiment of the invention, a helper lipid is mixed with the mixture of the gene transfer agent and the plasmid or polynucleotide to aid in the transfection. Examples of suitable helper lipids include cholesterol and dioleoylphosphatidylethanolamine (DOPE). Depending which gene transfer agent of the invention is used; one particular helper lipid may be more effective than the other at affecting transfection. For example, cholesterol may be more effective than DOPE with some particular gene transfer agents whereas DOPE may be more effective with others. It is within the ability of one of skill in the art to optimize the particular helper lipid depending on the particular application, given the disclosure herein. According to one embodiment, the ratio of the ratio of the gene transfer compound to the helper lipid is about 1.0:0.1 to about 1.0:1.5.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

The synthesis of the new cationic lipids is outlined in scheme 1. It is based on the original synthetic strategy reported previously,[17,1] which involves the reaction of substituted pyrylium salts with primary amines[19] to generate the cationic head and the linker in a single step (Scheme 1). Various pyrylium salts can be employed,[19] allowing different designs for the polar head, for targeting purposes or for inducing special optical properties (e.g. fluorescent cationic lipids as membrane markers[17]).

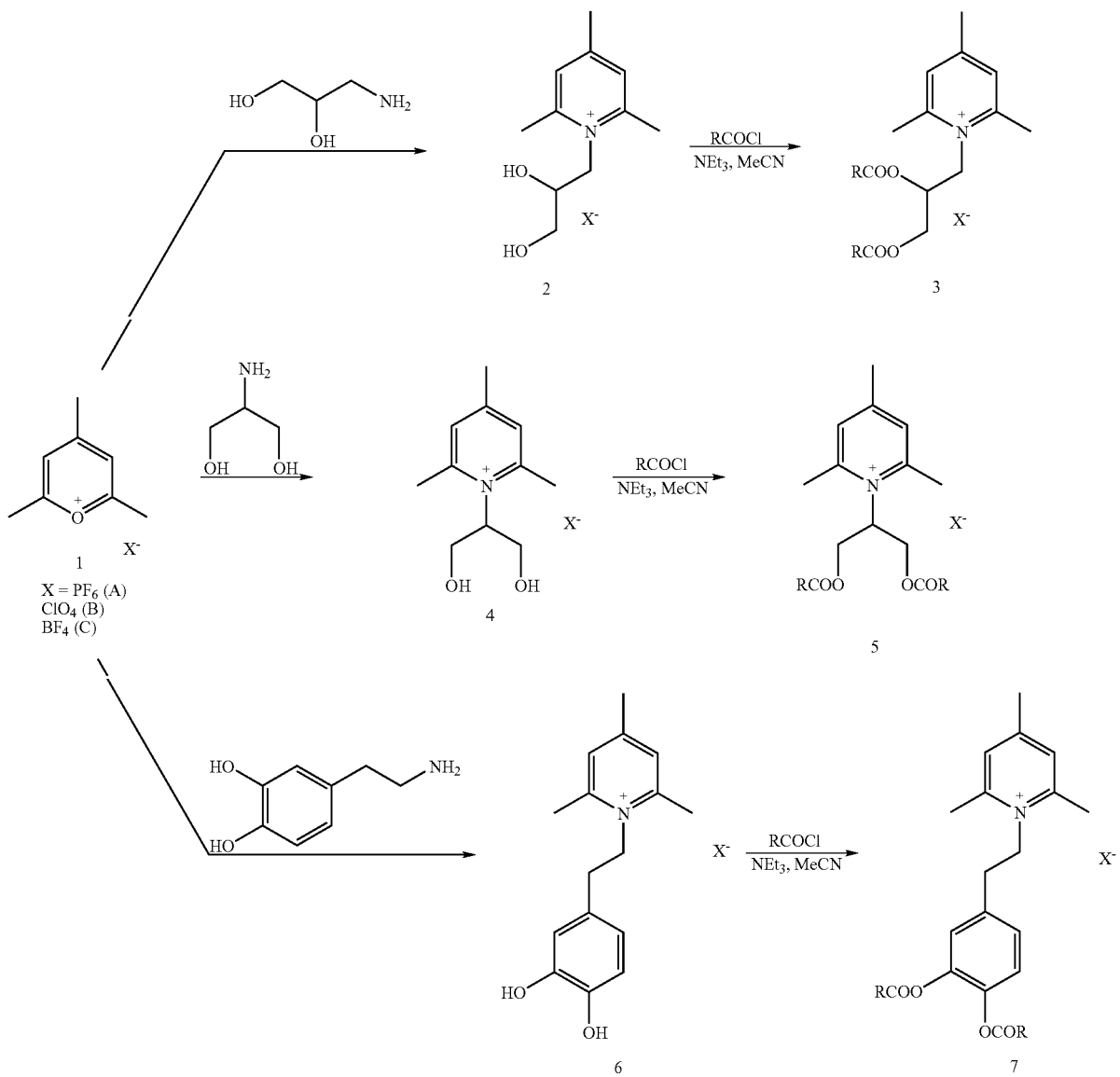

RCO = C$_7$H$_{15}$CO (Cpy)
C$_9$H$_{19}$CO (Cpc)
C$_{11}$H$_{23}$CO (Lau)
C$_{13}$G$_{27}$CO (Myr)
C$_{15}$H$_{31}$CO (Pal)
C$_{17}$H$_{35}$CO (Ste)
9(Z)——C$_{17}$H$_{33}$CO (Ole)

Scheme 1. Synthetic Pathways for the New Cationic Lipids

The choice of the appropriate amine allows the design of the linker. In order to investigate the influence of this structural element on the transfection efficiency of pyridinium cationic lipids, we decided to compare a flexible alkyl linker versus a flat, aromatic one, by using aminopropanediol or dopamine as precursors. Another variable was allowed at this stage by using either 3-amino-1,2-propanediol or serinol in the alkyl linker set. The key intermediates 2, 4 and 6 with two hydroxy groups were obtained in high yields and were subsequently acylated with a wide range of fatty acyl chlorides in order to generate the corresponding cationic lipids 3, 5 and 7. The pyridinium-based cationic lipids will be denoted by numbers followed by capital letters denoting the anion (A=PF$_6^-$, B=ClO$_4^-$, C=BF$_4^-$, D=Cl$^-$, E=I$^-$) and then by three letters indicating the fatty acid (Cpy=caprylic acid, Cpc=capric acid, Lau=lauric acid, Myr=myristic acid, Pal=palmitic acid, Ste=stearic acid, Ole=oleic acid). For the series bearing alkyl linkers we varied the length of the hydrophobic anchor from 12 to 18 carbon atoms, by analogy with similar studies on cationic lipids bearing trimethylammonium polar heads.[20-22] The ten cationic lipids 3ALau-3AOle and 5ALau-5AOle were thus obtained. For the dopamine-based series we also used shorter acyl chlorides (ranging from 8 to 18 carbon atoms) due to the additional contribution of the phenyl ring, yielding the seven pyridinium lipids 7ACpy-7AOle.

The hexafluorophosphate anion was selected as the first counterion in the study, in order to avoid the difficulties associated with the perchlorates (hazardous) or tetrafluoroborates (too soluble). These last two anions were used only in the synthesis of lipid 5Myr (following the same synthetic pathway), for studying of the counterion effect on transfection. The chloride and iodide salts of 5Myr, also used in the counterion study, were obtained via a different strategy, using anion exchange (Scheme 2). In the case of the chloride the anion exchange was accomplished with cesium chloride for the diol 4D, taking advantage of the high solubility of this compound in water, the very low solubility of $CsPF_6$, and the subsequent step of acylation with acyl chloride that conserves the anion. The soluble 5DMyr thus obtained was converted into the corresponding iodide 5EMyr using classic anionic exchange on a Dowex resin.

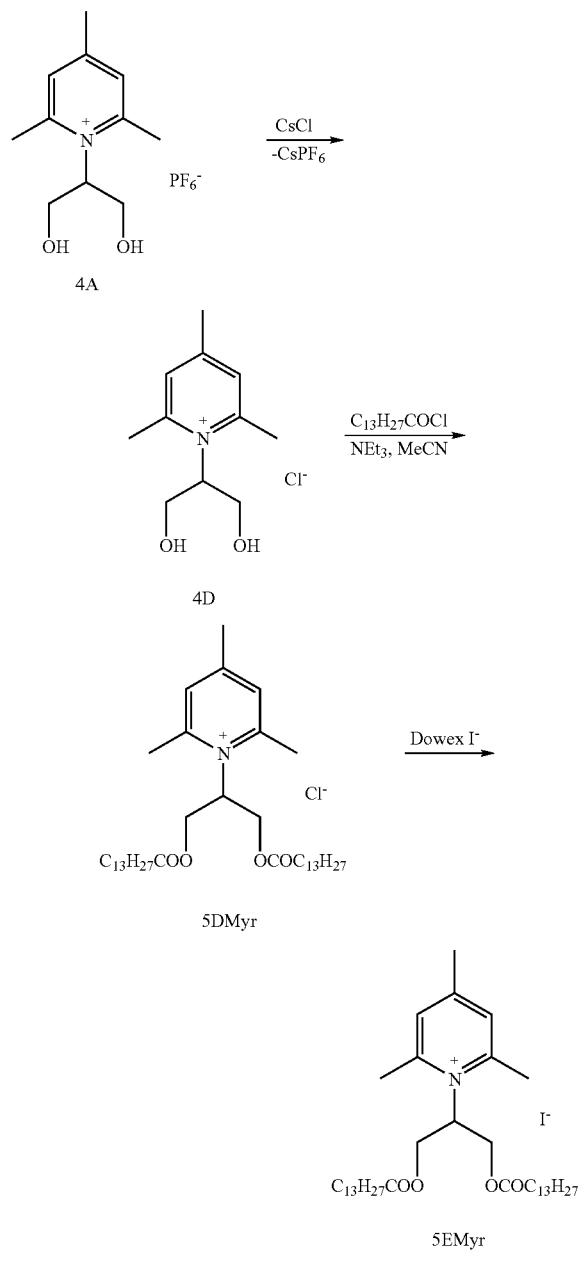

Scheme 2. Preparation of Cationic Lipids with Chloride and Iodide Anions

The resulted cationic lipids considered in this study, together with their critical temperatures, are summarized in Table 1.

TABLE 1

The cationic lipids analyzed in this study and their critical temperatures ($T_c$)

| | | $T_c$ (° C.) | |
|---|---|---|---|
| Lipid | Pure | With cholesterol (1:1 molar ratio) | With DOPE (1:1 molar ratio) |
| 3A Lau | 114.0 | 106.7 | |
| 3A Myr | 121.3 | 112.5 | 107.7 |
| 3A Pal | 123.5 | 114.0 | |
| 3A Ste | 122.5 | 112.7 | |
| 3A Ole | 67.9 | 58.5 | |
| 5A Lau | 58.2 | 41.9 | |
| 5A Myr | 67.8 | 64.8 | 22.4 |
| 5B Myr | 60.2 | 58.4 | |
| 5C Myr | 58.4 | 55.2 | |
| 5D Myr | 76.3 | 81.2 | |
| 5E Myr | 60.8 | 80.1 | |
| 5A Pal | 75.5 | 61.0 | |
| 5A Ste | 79.6 | 66.1 | |
| 5A Ole | 17.0 | 31.0 | |
| 7A Cpy | 134.1 | 127.3 | |
| 7A Cpc | 140.0 | 129.2 | |
| 7A Lau | 140.7 | 126.9 | |
| 7A Myr | 141.2 | 125.8 | |
| 7A Pal | 140.0 | 124.1 | |
| 7A Ste | 138.8 | 123.9 | |
| 7A Ole | 106.8 | 97.3 | |

As expected, one can note that the critical temperature ($T_c$), which is an important parameter for cationic lipids, decreases from the dopamine series to the two propanediol series, and among them it reaches a minimum for the for the 1,3-substituted compounds. Within the same series, the oleoyl derivative has the lowest $T_c$ due to the steric hindrance induced by the cis double bond. This is clearly shown in the energy minimization models performed by MM2 routine for saturated and unsaturated representatives from each series (FIG. 1).

Biological Activity

Influence of the Linker

The three series of cationic lipids newly synthesized were assessed for their transfection efficiency in vitro, using the experimental conditions optimized in a previous study.[23] Essentially the cationic lipids were mixed with cholesterol at a 1:1 molar ratio, dissolved in chloroform/methanol and dried under vacuum to generate a lipid film. The dried lipid film was hydrated with sterile phosphate buffer isotonic saline with pH=7.4 (PBS) and sonicated to yield cationic liposomes. The resulting liposomal solution was allowed to react with a DNA solution to form the final cationic lipid-DNA complexes (lipoplexes), which were assessed for transfection efficiency using different cell cultures. We used a pGL3 plasmid (Promega, Madison, Wisc.), encoding a firefly luciferase gene under the control of the constitutively active SV40 promoter as the reporter for the transfection efficiency. An optimal[23] electrostatic charge ratio cationic lipid/DNA of 2:1 was used in all preparations. We started with cholesterol (Chol) as co-lipid in the liposomal formulations due to the fact that it proved superior to dioleoylphosphatidylethanolamine (DOPE) for this type of pyridinium cationic lipids.[23] All liposomal preparations were sonicated for 30 minutes (twice 15 minutes, with a 15 minutes pause in between), at 65-68° C. for the new compounds and at 37° C. for the chosen reference cationic formulation DOTAP/Chol (1:1 molar ratio).[12,24] These conditions allowed us to generate a relatively homogenous population of liposomes, with sizes ranging from 90 to 140 nm, as determined by dynamic light scattering (see experimental section). The ability of these new cationic lipids to generate relatively small cationic liposomes could be attributed to the relatively large curvature radius induced in the bilayer by the bulky pyridinium cationic head. We used the lung cancer cell line NCI-H23, which among several cultured cell lines tested proved to be the most sensitive towards these cationic lipids[23] as the primary cell culture for in vitro experiments (see Experimental section). The results are summarized in FIG. 2.

Figure 2:
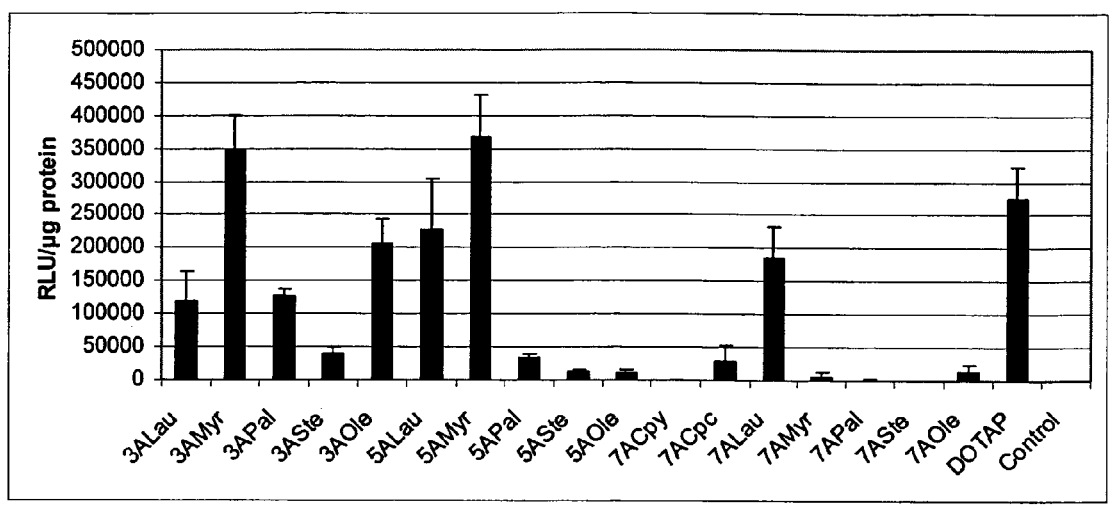
FIG. 2. Transfection data for the three series of cationic lipids and DOTAP (conditioned with cholesterol as helper lipid, at 1:1 molar ratio).

The analysis of data from FIG. 2 clearly shows the superiority of aliphatic linker versus the aromatic ones. In the aromatic series (7) the best transfection efficiency was achieved by the lauroyl derivative 7ALau, which was about five times more active than the decanoyl derivative 7ACpc and about ten times more efficient than the oleoyl derivative 7AOle. The transfection is clearly correlated with the fluidity of the resulted cationic liposomes, as the "stiffer" derivatives 7AMyr-7ASte showed low transfection efficiencies (see also Table 1 for $T_c$). The same trend with respect to the hydrophobic anchor can be recognized in the series 3 and 5, which bear aliphatic, flexible linkers. The highest transfection peaks were with the myristoyl derivatives 3AMyr and 5AMyr; a secondary peak is due to the oleoyl derivative 3AOle. Surprisingly, the 1,3-dioleoylderivative 5AOle displayed low transfection efficiency, and various attempts to improve the transfection efficiency of this compound yielded consistently low results. This fact may be due to the unfavorable conformation adopted by these molecules in the lipidic bilayer generated by the simultaneous action of the 1,3-linker and oleoyl fatty chains (FIG. 1). As a general observation, the oleoyl derivatives were always inferior to their myristoyl congeners for these lipids bearing pyridinium polar heads, a feature observed also by Massing et al.[22] for their DOTAP-like quaternary ammonium lipids conditioned with cholesterol as co-lipid.

Influence of the Helper Lipid

Following these preliminary observations we selected the lead compounds 3AMyr, 3AOle and 5AMyr for further investigations concerning the specific properties of the cationic liposomes they generate and their transfection ability. We started by checking the influence of the commonly used helper lipids cholesterol and DOPE in the transfection efficiency of pyridinium cationic liposomes, against DOTAP as reference. The ability of our lipids to act without any helper lipid was also tested in the same experiment, and the results are summarized in FIG. 3.

Figure 3:
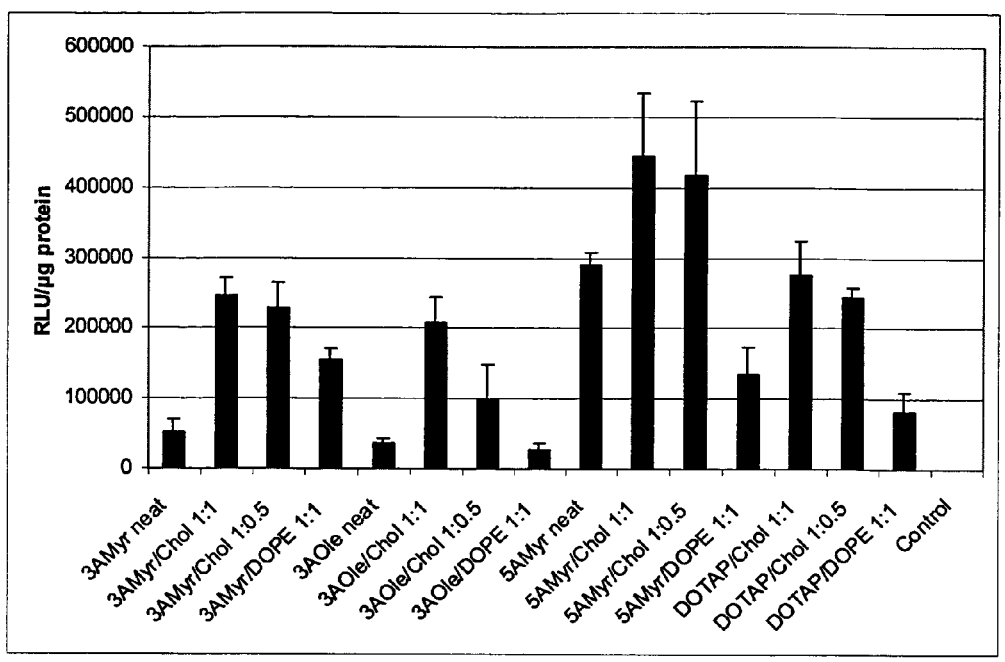
FIG. 3. The transfection efficiency of lead pyridinium cationic lipids and DOTAP (as reference) with different helper lipids FIG. 4. The influence of the sonication time on the cationic lipids 3AMyr, 3AOle and 5AMyr, versus DOTAP as standard. Al preparations were done with cholesterol as helper lipid at 1:1 molar ratio.

The data of FIG. 3 confirm the previous finding[23] that even when no helper lipid was used, the pyridinium cationic lipids alone were able to transfect the NCI-H23 lung cancer cell line. The liposomes generated from pure cationic lipids were generally very polydisperse, and relatively unstable. Cholesterol at 1:1 molar ratio to cationic lipids proved to be the best formulation for this type of cationic lipids, irrespective of the structure of the linker or hydrophobic anchor. The average diameter of the corresponding liposomes remained around 110 nm (88-132 nm) and the small differences in size did not seem to affect significantly the transfection efficiency. The vesicles were stable at room temperature and no aggregation was observed. Halving the molar ratio of cholesterol to lipid generated a decrease in the average size of the cationic vesicles (e. g. from 132 nm to 89 nm for 3AMyr, from 113 to 103 nm for 3AOle, and from 95 nm to 88 nm for 5AMyr), which translated into a slight decrease in the transfection efficiency. These findings can be explained considering the differences between the cross-section areas of polar head ($A_p$) and hydrophobic anchor ($A_{np}$) for the cationic lipids (see FIG. 1) and cholesterol.[49-53] In the case of the former ones, $A_p$ is close or exceeds $A_{np}$ (considering also the hydration shell of bulky pyridinium polar head), while cholesterol has $A_{np} < A_p$, so vesicles of higher curvature can be generated with less cholesterol. However, smaller sizes did not translate into higher transfection efficiencies, since cholesterol plays an essential role in the fluidity of the liposomes and lipoplexes. In previous optimization studies we had also found that the 1:1 molar ratio to cationic lipids seems to be optimal for cholesterol-based liposomes since any further increase of this ratio makes these liposomes and lipoplexes less efficient.[23] On the other hand, DOPE was less effective than cholesterol, irrespective of the structure of cationic lipid, thus confirming the conclusion of our preliminary study[23] and also the conclusions of Massing et al.[22]. The same trend in terms of the influence of the helper lipid and its molar ratio was found for DOTAP, similarly to observations of other research groups.[12]

Influence of the Sonication Time

Figure 4:
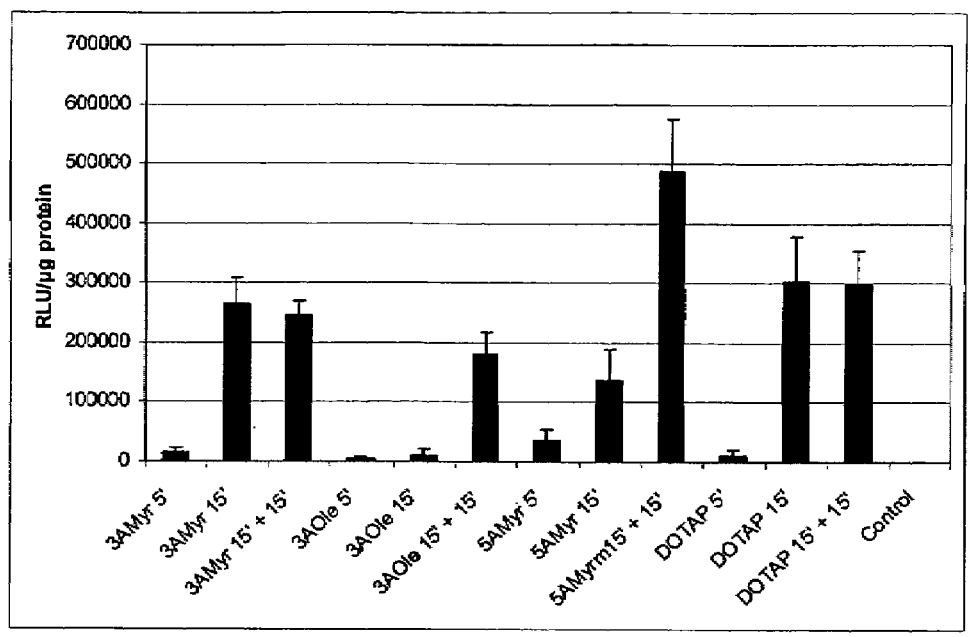

In order to check the best method for generating liposomes, we studied the influence of the sonication time on liposome size, coupled with a biological assessment of the transfection efficiency of the corresponding lipoplexes, and using the same DNA amount as in the previous studies presented above (FIG. 4).

The results showed that pyridinium cationic lipids required slightly more sonication time (usually twice 15 minutes with 15 minutes relaxation time in between) than DOTAP in order to form efficient liposomes. This can be attributed to the bulkier, less hydrophilic pyridinium polar head, as compared to the tetramethylammonium one, as well as to the less hydrophilic counterion ($PF_6^-$ versus $Cl^-$). The average diameter of the cationic liposomes after 5, 15 and 15+15 minutes of sonication were 366 nm, 130 nm and 138 nm for 3AMyr/Chol 1:1, 130 nm, 110 nm and 118 nm for 3AOle/Chol 1:1, 131 nm, 195 nm and 123 nm for 5AMyr/Chol 1:1 and 150 nm, 117 nm and 122 nm for DOTAP/Chol 1:1, respectively. However, the transfection trend remained the same, namely 5AMyr/Chol 1:1 was the most efficient liposomal preparation when optimally conditioned. Changing the hydration medium from PBS to 5% glucose[12] did not improve the transfection efficiency of the tested cationic lipids (data not shown).

Influence of the Counterion

Figure 5:
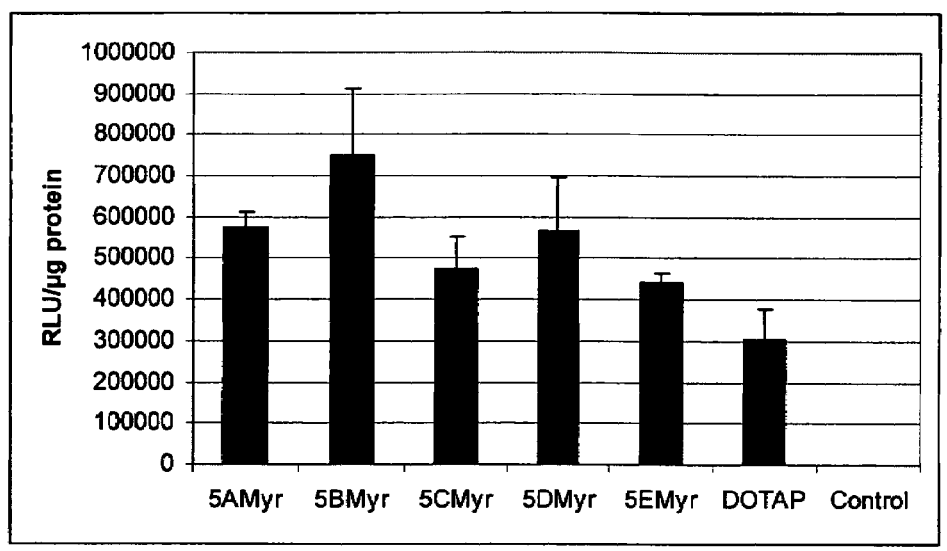
FIG. 5. Transfection of NCI-H23 lung cancer cells with lipids 5Myr bearing different counterions: $PF_6^-$ (A), $ClO_4^-$ (B), $BF_4^-$ (C), $Cl^-$ (D), $I^-$ (E), and with DOTAP ($Cl^-$). All the preparations were done with cholesterol at 1:1 molar ratio to the cationic lipid, hydrated with PBS and sonicated for two sequences of 15 minutes each. The resulted cationic liposomes were allowed to interact with the same amount of DNA to form the final lipoplexes.

Another important element in the structure of cationic lipids is the counterion of the positively charged polar head. It is known that counterions play an important role in cationic liposome properties, influencing the cationic lipid hydration shell and therefore the cross-section area of the polar head ($A_p$). Moreover, the interaction of cationic liposomes with DNA is driven not only by the electrostatic attraction between the positively charged lipid head groups and the negatively charged phosphate groups on the DNA, but also by the entropically-favoured release of the counterions of both DNA and cationic lipids.[7,27] The counterions also have a great impact on the intrinsic cytotoxicity of the cationic lipid. Consequently we investigated the influence of the counterion on the transfection efficiency using 5Myr/Chol 1:1 hydrated with PBS and sonicated for two sequences of 15 minutes each as the favored liposomal preparation. The lipids 5Myr bearing different anions such as hexafluorophosphate (5AMyr), perchlorate (5BMyr), tetrafluoroborate (5CMyr), chloride (5DMyr), and iodide (5EMyr) were synthesized according to Schemes 1 and 2. Data from Table 1 show that the critical temperature of the lipid is considerably influenced by the counterion, increasing in the order $BF_4^- < ClO_4^- < I^- < PF_6^- < Cl^-$. This is also valid for the corresponding mixtures with cholesterol at 1:1 molar ratio. However, the transfection efficiency of the liposomal preparations based on 5Myr with these counterions did not follow the same trend (FIG. 5).

One can observe that the perchlorate 5BMyr yielded the most efficient lipoplexes, followed by the hexafluorophosphate 5AMyr, chloride 5DMyr, tetrafluoroborate 5CMyr, and iodide 5EMyr.

Figure 6:
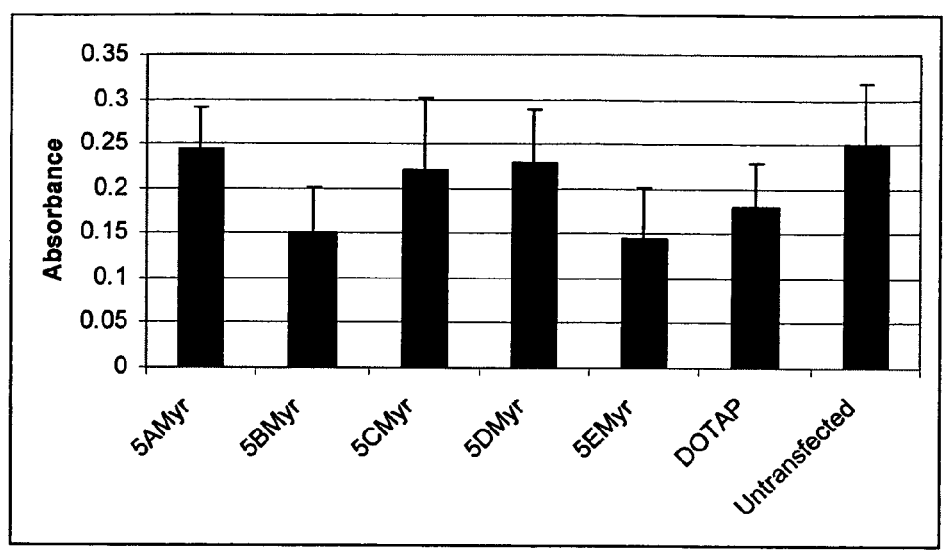
FIG. 6. Viability assay results for the cancer cell line NCI-H23 transfected with 5AMyr-5EMyr and DOTAP ($Cl^-$)-based lipoplexes. The other characteristics were the same as in the transfection experiment represented in FIG. 5.

In order to assess the cytotoxicity associated with every anion, a WST-1[28] viability assay was conducted in parallel. The results, summarized in FIG. 6, showed that the minimum cytotoxicity was obtained with the hexafluorophosphate 5AMyr, chloride 5DMyr and tetrafluoroborate 5CMyr whereas the perchlorate 5BMyr and iodide 5EMyr were more cytotoxic. We emphasize that the optimum effect transfection/cytotoxicity is attained with hexafluorophosphate and chloride, and that 5Myr conditioned with these anions surpassed DOTAP in transfection efficiency, simultaneously displaying a lower cytotoxic effect. The duration of cell exposure to lipoplexes generated from 5AMyr, and 5DMyr from one hour to three hours translates into higher transfection efficiencies without any visible cytotoxic effect (data not shown).

Influence of the Cell Line

Figure 7:
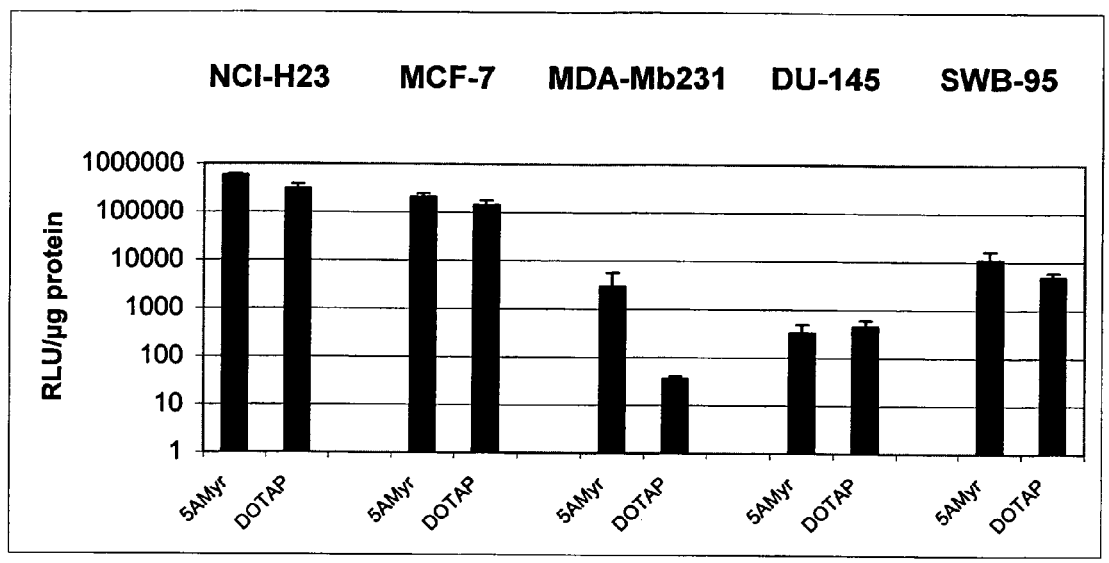
FIG. 7. Transfection efficiency of optimized 5AMyr-based lipoplexes versus DOTAP-based lipoplexes on different tumor cell lines. Note: log scale. Values for 5AMyr and DOTAP were 576000; 303000 (NCI-H23; from FIG. 4), 206000; 143000 (MCF-7), 2950; 36 (MDA-Mb231), 327; 442 (DU-145), 10934; 4810 (SWB-95).

It is well known that specific cell types and cell lines may vary in their ability to be transfected. In addition to the NCI-H23 lung cancer cell line, we therefore tested our optimized formulation of 5AMyr/Chol 1:1 versus DOTAP/Chol 1:1 as reference on four other cell lines from tumors representing cancers of great importance to human health, as well as different tissues of origin: breast carcinomas MCF-7, MDA-Mb231, prostate carcinoma DU-145 and glioma SWB-95 (FIG. 7).

The results showed that transfection occurred on all cell types. Using 5AMyr/Chol 1:1 in NCI-H23 cells resulted in 1.5-2 times greater expression of luciferase than did DOTAP/Chol 1:1 (see FIG. 4). The above combination also performed better in MCF-7, MDA-Mb231, and SWB-95 cells (FIG. 7). The differences were statistically significant at p<0.05 or better in all cases. Actual values are given in the caption of FIG. 7. Interestingly, the glioma SWB-95, known as a cell line relatively hard to transfect, showed significant transfection. The breast carcinoma MDA-Mb231, as well as the prostate carcinoma DU-145 showed relatively modest levels of transfection with both 5AMyr/Chol and DOTAP/Chol. The high sensitivity of NCI-H23 lung carcinoma to pyridinium lipoplexes may be associated with the existence of a polyamine transporters that is particularly effective for pyridinium compounds.[23, 30] Normal cell lines are very hard to transfect in the same conditions with either 5AMyr/Chol or DOTAP/Chol due to a much lower metabolic and division activity than that of tumor cells. This fact is important for in vivo studies using apoptotic plasmids, where selective killing of tumor cells is essential.

These findings were confirmed by a different experiment using a plasmid expressing the gene for the enhanced green fluorescent protein (GFP). After transfection, the cultures were evaluated for expression of the gene by fluorescence microscopy. Examples of these transfected cells showed clearly the superiority of 5AMyr/Chol on DOTAP/.

Three series of new pyridinium cationic lipids bearing different linkers and hydrophobic anchors were synthesized using an original approach based on the high-yield reaction of pyrylium salts with aminodiols that allows the simultaneous generation of the polar head and linker in a single step.[23] A structure-activity relationship study was conducted for identifying the most effective structural parameters and their influence on transfection efficiency using the lung cancer cell line NCI-H23. The best transfection efficiencies were obtained with compounds having an aliphatic linker and myristoyl fatty chains, the compound 5AMyr being the most effective (about twice more effective than DOTAP). We identified cholesterol at a molar ratio of 1:1 as the optimum helper lipid for these pyridinium cationic lipids. Mention must be made that DOTAP/Chol 1:1 formulation was used successfully for in vivo experiments[31] and that this formulation was also evaluated in gene therapy on human subjects.[32]

We also studied the effect of the counterion on transfection and cytotoxicity and we found that 5Myr/Chol 1:1 was more effective and less cytotoxic than DOTAP/Chol 1:1 when hexafluorophosphate or chloride anions were used as counterions for the pyridinium polar head. Tests on other tumor cell lines using different plasmids showed that the transfection efficiency with pyridinium cationic lipids was cell-dependent, and that 5AMyr/Chol 1:1 performed better than DOTAP/Chol 1:1 on the majority of these cell lines. The most susceptible remained the lung carcinoma NCI-H23, and this fact may be linked to the existence in these cells of a polyamine transporter that is particularly effective for pyridinium compounds. This finding gives good hopes of using the new pyridinium cationic lipids as gene transfer agents in the treatment of lung cancer and cystic fibrosis.

Considering also the success of several studies using the pyridinium moiety in the generation of membrane-impermeant inhibitors and activators of carbonic anhydrase[33,34] (which confers isozyme selectivity) with applications as anticancer agents,[35] this study demonstrates once again the usefulness of the pyridinium group as a versatile moiety in drug targeting.[36]

General. Melting points for the diols and the phase transition temperature $T_c$ for the cationic lipids were determined by differential scanning calorimetry (DSC), using a TA-Instruments Q100 DSC, and a heating rate of 5° C./minute. The IR spectra were recorded on a Nicolet Avatar 360 FTIR spectrophotometer in the range 650-4000 cm$^{-1}$ using a ZnSe—attenuated total reflectance (ATR) accessory. The compounds were solved in a small amount of solvent (MeOH for the diols, CHCl$_3$ for the lipids), and the resulted solutions were left to evaporate to dryness on the surface of the ZnSe crystals of the ATR accessory. The NMR spectra were recorded at ≈303 K with a Varian Inova spectrometer equipped with a 5 mm indirect detection probe, operating at 500 MHz for $^1$H-NMR and at 125 MHz for $^{13}$C-NMR. Chemical shifts are reported as δ values, using TMS as internal standard for proton spectra and the solvent resonance for carbon spectra. Assignments were made based on signal intensity, selective decoupling, COSY ($^1$H-$^1$H) and HETCOR ($^1$H-$^{13}$C) sequences. Elemental analyses were performed by combustion, using a Perkin Elmer 2400 Series II CHNS analyser.

Racemic 3-amino-1,2-propanediol, 2-amino-1,3-propanediol, triethylamine, acetic anhydride, acetic acid, acyl chlorides and other solvents were from Acros. TLC was performed on silicagel 60-F$_{254}$ plates (Merck), eluted with MeOH:CHCl$_3$ 20:80 (v/v). The pyrylium salts were prepared according to the literature.[19,37,38] CAUTION: Since perchlorates may explode when they are heated or upon impact in dry form, they should be stored moist with water.

General Procedure for the Preparation of the Pyridinium Diols 2, 4 and 6:

The aminodiol (10 mmoles) was dissolved by stirring in anhydrous ethanol (30 mL). Next, the corresponding pyrylium salt (12 mmol of hexafluorophosphate, perchlorate, tetrafluoroborate) was added, followed immediately by the addition of 12 mmol of triethylamine. In the case of dopamine, commercially available as hydrochloride, the quantity of triethylamine was doubled. The resulted mixture was refluxed for 15 minutes, then glacial acetic acid (25-30 mmol) was added and the reflux was continued for 1-3 hours (TLC control). After this period, concentrated aqueous ammonia (2 mL) was added and the mixture was heated for 5 minutes in order to convert any unreacted pyrylium salt into the corresponding pyridine, which is soluble in diethyl ether. The final solution was cooled and poured under stirring into anhydrous diethyl ether (200-300 mL). In the case of aliphatic aminodiols the resulting insoluble heavier oily layer was separated and washed with two additional portions (20 mL each) of diethyl ether. After a final separation, the oily layer was taken in a few milliliters of hot isopropyl alcohol, treated with charcoal, filtered, and allowed to cool slowly when crystallization occurred. In the case of dopamine the precipitated product was filtered, dried, and washed with water to eliminate the ammonium salts. Yields were in the range of 50-85%. The products were recrystallized from methanol or isopropanol.

General Procedure for the Preparation of the Pyridinium Lipids 3, 5 and 7:

The pyridinium diol 2, 4 or 6 (2 mmol) was dissolved by stirring in 15-30 mL of anhydrous acetonitrile. Triethylamine (0.56 mL, 4 mmol) was added, followed by dropwise addition of acid chloride RCOCl (4.4 mmol) when the color became yellow, and triethylamine hydrochloride started to precipitate. The suspension was stirred for 15 minutes at room temperature and then refluxed for another 3-5 hours. The solvent was evaporated (rotavapor) under reduced pressure, and the residue was extracted with 15 mL of distilled water and 15 mL of chloroform. The aqueous layer was separated, extracted with 15 mL of chloroform, and discarded. The combined chloroform extracts were shaken with 15 mL of distilled water, dried over sodium sulfate, and evaporated under reduced pressure. Final purification was effected by flash chromatography on silica gel 60 (40-60 µM) with a solvent mixture of chloroform and methanol (80:20 v/v), followed by recrystallization form ethanol.

Anion Exchange Procedure for Obtaining the Pyridinium Diol 4D

The pyridinium propanediol hexafluorophosphate 4A (0.68 g, 2 mmol) was dissolved under gentle heating in 1 mL of distilled water and treated with a warm solution obtained by dissolving 0.42 g cesium chloride (2.5 mmol) in 1 mL of distilled water. Precipitation of cesium hexafluorophosphate occurred instantaneously and was finalized by slowly cooling the suspension at room temperature and then to 0° C. The precipitate was filtered off and the resulted solution evaporated to dryness to yield the crude pyridinium chloride, which was used directly into the next step.

Anion Exchange Procedure for Obtaining the Pyridinium Lipid 5EMyr

An amount of 10 g DOWEX anion exchange resin 1X8 (in chloride form) was suspended in bidistilled water and allowed to completely swell overnight. The next day the resin was packed in a small column and treated with a solution of 25 g potassium iodide in 80 mL of bidistilled water. The resin gradually turned yellow when eluted due to iodide binding. Then the resin was washed with distilled water until no halide anions were detected in the eluted fractions (AgNO$_3$ test).

Then 60 mL 95% EtOH was added in order to change the polarity of the medium, followed by the sample (5Dmyr, 70 mg), dissolved in 3 mL EtOH 95%. Isocratic elution with 95% EtOH afforded the desired 5Emyr, which was concentrated and recrystallized from absolute ethanol. Yield 53 mg (69%).

The present invention describes a new class of cationic lipids with a positively charged substituted pyridinium ring, which is synthesized from a pyrylium salt and a primary amine (an amino-dihydroxypropane), as shown in Chart 1. The pyrylium salt 1 can be easily obtained from inexpensive starting materials in good yield, with various substituents R in positions 2 and 6 (α-positions) depending on the nature of the anhydride. The substituent in position 4 (γ-position) indicated in Chart 1 is a methyl group originating in the alkene (isobutene under the form of its precursor, tertiary-butanol). An alkene is the intermediate in the diacylation leading to pyrylium salts, a reaction discovered by Balaban and Nenitzescu [11]. If one starts from another alkene than isobutene, for instance α-methylstyrene, one obtains a γ-phenyl-substituted pyrylium salt.

The anion X$^-$ originates in the acid used in the diacylation, and it can also be varied, e.g. tetrafluoroborate [12], trifluoromethanesulfonate [13], sulfoacetate [14], or hexafluorophosphate. Reviews on pyrylium salts are available, including two in book form [15-18].

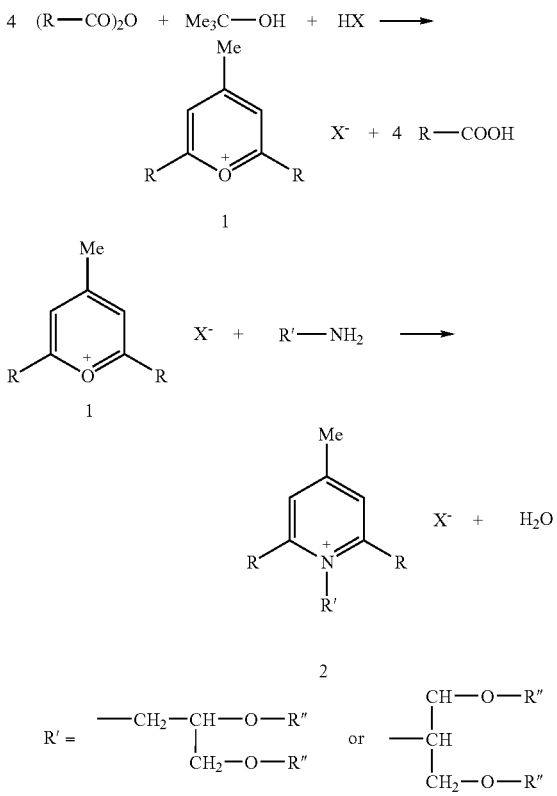

Chart 1

In addition to pyrylium salts with symmetrical structure (i.e. with identical α-substituents such as 2,4,6-trimethylpyrylium, 4-methyl-2,6-dialkylpyrylium or 4-methyl-2,6-diphenylpyrylium salts, prepared as shown in Chart 1), one can start with pyrylium salts obtained by other synthetic approaches. Thus, monoacylation of mesityl oxide yields 2,4-dimethyl-6-alkylpyrylium salts. 2,4,6-Triphenylpyrylium salts can be prepared from two moles of chalcone and one mole of acetophenone in a one-pot acid-catalyzed condensation and hydrogen transfer reaction [19].

The conversion of pyrylium salts into pyridinium salts takes place in high yield under the nucleophilic attack of a primary amine R'—NH$_2$ [20-22]. Compounds with two or three primary amino groups react with pyrylium salts forming bis- and tris-pyridinium salts, respectively [23,24]. When the R group is a long-chain alkyl [20,25] or aralkyl group [26], one obtains surface-active agents. If, however, two long-chain alkyl or alkenyl groups are present, then bilayer formation becomes possible. Ideally, if the R'' groups contained in the primary amine (as indicated at the bottom of Chart 1) would be long-chain acyl, alkyl or alkenyl groups, this would lead directly to the desired lipofectins. However, such diesters or diethers of dihydroxypropylamine are difficult to obtain, therefore one performs a two-step reaction, as indicated in Chart 2. In this Chart, for simplicity, the group R in the pyrylium salt 1 is assumed to be methyl, and only esterification is taken into account (etherification by means of a Williamson synthesis is also a viable alternative, as shown below). The pyrylium salt is reacted first with an aminodihydroxyalkane to yield a pyridinium salt, and then this is esterified with two moles of a fatty acid chloride R''—COCl in the presence of a tertiary base. The fatty acid chloride is a derivative of a saturated straight-chain monocarboxylic acid with 14-18 carbon atoms, or of an unsaturated one such as oleic acid. Anhydrides may also replace acid chlorides. One can use either 1-amino-2,3-dihydroxypropane to prepare an N-(2,3-dihydroxy-1-propyl)-pyridinium salt 3 and then its diester 4, or 2-amino-1,3-dihydroxypropane (serinol) for obtaining an N-(1,3-dihydroxy-2-propyl)-pyridinium salt 5 and then its diester 6. Thiol groups may replace hydroxy groups in the aminodihydroxyalkane For simplification, we have not indicated on the formulas that it is also possible to obtain mixed esters by reacting the N-dihydroxypropylpyridinium salts first with one mole of an acid chloride and then with one mole of a different acid chloride. The pyridinium salt 5 cannot lead to mixtures of isomers because it has equivalent hydroxy groups, but in principle compound 3 can; however, this is unlikely because in $S_N2$ nucleophilic substitutions primary alcoholic groups react faster than secondary ones.

The chiral carbon atom of compounds 3 and 4 gives rise to diastereotopic protons of both methylene groups, as evidenced by the $^1$H-NMR spectra. On the other hand, steric hindrance and the small R—N bond distance of pyridinium salts lead to restricted rotation manifested in the chemical shift non-equivalence of methyl groups in 5 and 6 at room temperature. At higher temperatures, coalescence of NMR peaks was observed.

Chart 2

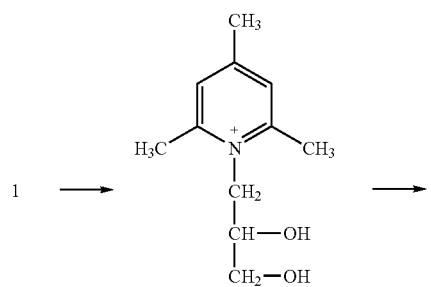

3

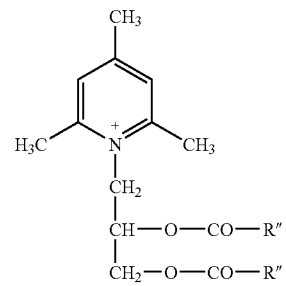

4

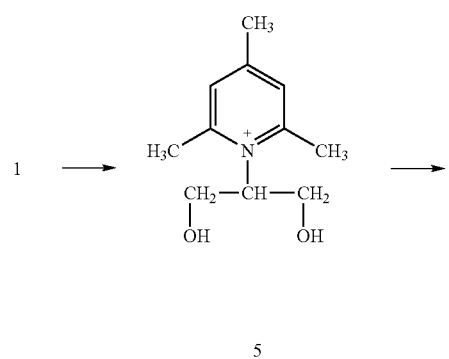

5

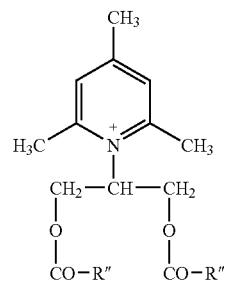

6

Instead of double esterification, the pyridinium diols 3 and 5 may be doubly etherified by tosylation followed by treatment with a long-chain alkoxide (e.g. from hexadecanol and sodium tert-butoxide), resulting in a pyridinium lipid with two long-chain alkoxy groups instead of the carbalkoxy groups of 4 and 6.

Finally, on replacing the pyrylium salt 1 by a styrylpyrylium salt 7 obtained as described in an earlier paper [27] and proceeding as described for the reaction with an aminopropanediol followed by esterification or etherification, one obtains colored, fluorescent cationic lipids (Chart 3). When R=H or Alk, salts 7 in Chart 3 and the corresponding cytofectins obtained from them are yellow; when R=OMe or OEt, they are orange-red, and when R=NMe$_2$ or NEt$_2$ they are blue.

Chart 3

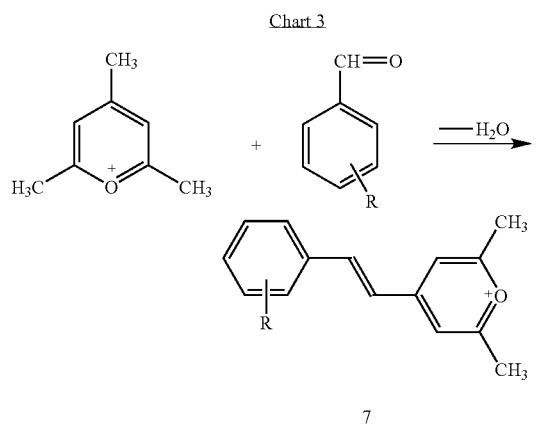

The present invention describes a new approach for obtaining cytofectins with a pyridinium ring starting from pyrylium salts. Advantages of the present method are: low cost of starting materials, convenient yields, easy purification, and a wide range of available structures by variation of the pyrylium cation, its anion, the aminodihydroxyalkane, and esterification/etherification reagents. In addition, when using a styrylpyrylium salt, one obtains colored and fluorescent cytofectins.

General Procedure for the Preparation of N-pyridinium-propanediols 3 and 5

An amount of 10 mmoles of commercial aminopropanediol was dissolved under stirring in 30 mL of anhydrous ethanol (when using commercial aminopropanediol hydrochloride, 10 mmoles of freshly cut sodium was first refluxed with the ethanol for yielding sodium ethoxide, and then the hydrochloride, 10 mmol, was added, the solution was stirred for 15 minutes and filtered for separating the resulted sodium chloride). Next, 12 mmoles of the corresponding pyrylium salt (chloride, tetrafluoroborate, or hexafluorophosphate [12-15]) were added, followed immediately by the addition of 12 mmoles of triethylamine. The resulted homogeneous mixture was heated to reflux for 15 minutes, then 25 mmoles of glacial acetic acid were added and the reflux was continued for 1-3 hours more (TLC control). After this period, 2 mL of concentrated aqueous ammonia were added and the mixture was heated for another 5 minutes in order to convert any unreacted pyrylium salt into the corresponding pyridine which is soluble in diethyl ether. The final solution was cooled and poured, under stirring, into anhydrous diethyl ether (200-300 mL). The resulting insoluble heavier oily layer was separated and washed with two additional portions (20 mL each) of diethyl ether. After a final separation, the oily layer was taken in a few milliliters of hot isopropyl alcohol, treated with charcoal, filtered, and allowed to cool slowly when crystallization occurred; if not, the resulted viscous oil was separated from the mother liquor, redissolved in the minimum amount of hot methanol or isopropanol, and the concentrated solution was allowed to cool when crystallization occurred. Yields were in the range of 45-90%. The products were recrystallized from methanol or isopropanol.

1-(2,3-Dihydroxypropyl)-2,4,6-trimethylpyridinium tetrafluoroborate: m.p. 96-97° C.

General Procedure for the Preparation of N-pyridiniumpropanediol Esters 4 and 6

The N-dihydroxypropylpyridinium salt (3 or 5) (500 mg, 1.69 mmol) was dissolved under stirring in 10 mL anhydrous acetonitrile. Triethylamine (0.47 mL, 3.38 mmol) was added, followed by dropwise addition of 3.38 mmol acid chloride R″—COCl when the color becomes yellow, and triethylamine hydrochloride starts to precipitate. After stirring at room temperature for 3 hours, the solution was refluxed for 2 hours. The solvent was evaporated (rotavapor) under reduced pressure, and the residue was extracted with 10 mL distilled water and 10 mL chloroform. The aqueous layer was separated, extracted with 10 mL chloroform, and discarded. The combined chloroform extracts were shaken with 10 mL distilled water, dried over sodium sulfate, and evaporated under reduced pressure. Final purification is effected by column chromatography on silica gel 60 with a solvent mixture of chloroform and methanol (80:20 v/v), followed by recrystallization form acetonitrile for chlorides, and hexafluorophosphates, and from n-hexane for tetrafluoroborates.

1-(2,3-Dipamitoyloxypropyl)-2,4,6-trimethylpyridinium tetrafluoroborate $T_c$: 100° C.;

1-(2,3-Distearoyloxypropyl)-2,4,6-trimethylpyridinium tetrafluoroborate $T_c$: 103° C.;

1-(2,3-Dioleoyloxypropyl)-2,4,6-trimethylpyridinium tetrafluoroborate $T_c$: 52° C.

1-(1,3-Dipamitoyloxypropane-2-yl)-2,4,6-trimethylpyridinium tetrafluoroborate: $T_c$: 70°;

1-(1,3-Distearoyloxypropane-2yl)-2,4,6-trimethylpyridinium tetrafluoroborate: $T_c$: 73°;

1-(1,3-Dioleoyloxypropane-2-yl)-2,4,6-trimethylpyridinium tetrafluoroborate: $T_c$: 43° C.;

Preparation of Fluorescent Cationic Lipids

Two methods were employed. The first one repeated the procedure outlined above but the 2,4,6-trimethyl-pyrylium and -pyridinium rings were replaced by 2,4,6-triphenyl-substituted congeners, yielding fluorescent esters or ethers of 2,4,6-triphenylpyridinium-propanediols.

The second method started with 2,4,6-trimethylpyrylium, 2,6-di-tert-butyl-4-methylpyrylium or 2,6-diisopropyl-4-methylpyrylium salts (tetrafluoroborate, hexafluorophosphate, chloride) that were condensed with para-substituted benzaldehyde derivatives. The resulting products (7 when starting with 2,4,6-trimethylpyrylium) have characteristics presented in Table 2. Then these were further converted into fluorescent styryl-substituted pyridinium-propanediols and the corresponding esters or ethers.

TABLE 2

Data for 4-styryl-substituted 2,4,6-trimethylpyrylium salts

| para-Substituent | Anion | M.p. | Formula | λmax (nm) |
|---|---|---|---|---|
| 4-OMe | $BF_4$ | 249 | $C_{22}H_{29}BF_4O_2$ | 434 |
| 2-OEt | $BF_4$ | 201 | $C_{23}H_{31}BF_4O_2$ | 424 |
| 4-NMe$_2$ | $PF_6$ | 177 | $C_{23}H_{32}F_6NOP$ | 569, *607 |
| 4-NEt$_2$ | $BF_4$ | 188 | $C_{25}H_{36}BF_4NO$ | 579, *620 |

Preparation of Liposomes

Dioleoylphosphatidylethanolamine (DOPE), cholesterol (CHOL), N-(2,3-dioleoyloxypropyl)-N,N,N-trimethylammonium chloride (DOTAP) were commercial products. The purity of the lipids was checked by thin layer chromatography and also by differential scanning calorimetry (DSC), which was also used for determining the critical temperature $T_c$. For the preparation of the liposomes a protocol optimized for this type of compounds was adopted as follows. The cationic lipid (with or without helper lipid) was dissolved in chloroform/methanol (2/1, v/v) to reach a final concentration of 1 mM for the charged species. From this stock solution 50 μL were aliquoted in a 1 mL tube and the solvent was evaporated in a SpeedVac evaporator, under vacuum, for 1 h. The dried lipid film was prepared by removing the traces of organic solvent in a dessicator, over Drierite®, under vacuum, overnight. The film was hydrated with 500 μL sterile phosphate buffer saline (PBS) the tube was purged with sterile $N_2$, and vortexed for 1 minute. The liposomes were generated by sonicating the tube in a water bath sonicator for 5-30 minutes at 62° C. and at 37° C. for DOTAP. After sonication the preparations were allowed to reach room temperature.

Preparation of Lipoplexes

Two plasmids were used in this study: the first one was pGL3 (Promega, Madison, Wisc.), encoding a firefly luciferase gene. The second one was encoding a green fluorescent protein (GFP). Each plasmid was amplified in *Escherichia coli* and purified.

For generating the lipoplexes, 1.4-2.8 μL plasmid DNA solution (0.5 μg/μL) was diluted with 100 μL Optimem®. A liposome solution was prepared separately by diluting the initial liposomal stock solution (0.1 mM in cationic lipid) with Optimem® in specified proportions, to reach a final volume of 50 μL. Over this liposome solution 50 μL of the DNA stock solution was added, the tube was incubated for 30 minutes at room temperature and then the content diluted with 500 μL Optimem® (final volume of the lipoplex stock solution: 600 μL).

Cell Transfection

The lipoplexes was tested for their transfection properties over five different cancer cell lines—breast carcinoma (MCF-7 and MDA-Mb231), lung carcinoma (NCI-H23), prostate carcinoma (DU-145) and brain carcinoma (SWB-95). The cells were maintained in 10% fetal bovine serum (FBS)—enriched RPMI 1640 at 37° C. and 5% $CO_2$ in a humidified atmosphere. Twenty-four hours prior to transfection the cells were transferred in 96-wells microtiter plate at a density of 20,000 cells/well. Each well received 100 μL medium and the plate was incubated in the same conditions. All experiments were done in triplicate or quadruplicate.

Immediately before transfection the medium was removed from each well and the cells were briefly washed with 200 μL sterile PBS. After removal of the PBS each well received 100 μL lipoplex stock solution and the plate was placed in the incubator for 1 hour. Then, 100 μL medium was added to each well and the plate was incubated for 24 hours.

Luciferase and Protein Assay

Next day after transfection the medium was aspirated and the wells were washed briefly with 200 μL PBS. After removal of PBS the cells were lysed by adding 100 μL 1× reporter lysis buffer to each well and incubating the plate at 37° C. for 10 minutes. The cell suspension was collected and used for luciferase and protein assays.

For the luciferase assay, 20 μL of cell lysate was aliquoted in a test tube and assessed directly using a luciferase assay kit from Promega by means of a luminometer.

The protein content was quantified using a bicinchoninic acid (BCA) assay. The BCA assay was prepared as specified in manufacturer's instructions; 40 μL of cell lysate were treated with 1 mL of BCA reagent in an acryl vial and the solution was incubated 1 h at 37° C. The protein content was then read at 562 nm by means of an UV-VIS Spectrophotometer. The luciferase activity was normalized for protein content and expressed as RLU/μg of protein.

Cell Culture Results

Results for two cell lines (MCF-7 and NCI-H23) are presented in FIGS. 1 and 2, respectively, using cholesterol as helper lipid in molar ratio 1:1. Compounds 1-5 in these figures are lauric, myristic, palmitic, stearic, and oleic esters of 1-(2,3-dihydroxypropyl)-2,4,6-trimethylpyridinium hexafluorophosphate, respectively; the next compounds (6-10) in these figures are esters of 1-(1,3-dihydroxypropyl)-2,4,6-trimethylpyridinium hexafluorophosphate with lauric, myristic, palmitic, stearic, and oleic acids, respectively. It can be seen that MCF-7 cells are less easy to transfect than lung human cancer cells NCI-H23. Among our esters, those with myristic and oleic acids gave the best results. With the same protocol, DOTAP has a transfection efficiency that is only a fraction (20-50%) of the best results with our compounds on the same cell lines.

Cationic lipids are a promising alternative to viral vectors for gene therapy, allowing the delivery of larger plasmids without immunogenicity, despite their lower transfection efficiency. Among them, heterocyclic systems with imidazolium or pyridinium polar head groups have definite advantages such as the excellent transfection profiles and low cytotoxicity.

Our approach for synthesizing heterocyclic cationic lipids differs from those previously described because we synthesize a pyridinium ring from simple starting materials. First a pyrylium salt is formed via diacylation of alkenes. The pyrylium salt is then converted by primary amines into pyridinium salts. Appropriate choice of the primary amine allows the attachment of two hydrophobic chains yielding compounds 21A and 25A (with various chain lengths derived from palmitic, stearic and oleic acids). The same strategy allowed the preparation of lipophilic derivatives 21B, 25B useful as strongly fluorescent markers for the study of the properties of biological membranes.

Preliminary tests with some of the compounds 21A and 25A, on several cell lines, showed comparable transfection efficiencies and lower cytotoxicity than those obtained with standard commercial transfection agents.

Notation in formulas 17 through 25: A or B denote R=Me or Ph, respectively; a or b denote $ClO_4$ or $BF_4$ anions, respectively; P, S, or O denote palmitoyl, stearoyl, or oleoyl residues, respectively.

In the last decade gene therapy emerged as a revolutionary approach to treat diseases at the level where they are generated: the living cell.[1-3] When the cellular machinery is impaired due to a deficient gene, a functional gene incorporated into an appropriate vector is delivered to the affected cells/tissues. After internalization, the DNA is transferred to the nucleus where the gene is integrated into the host genome. After transcription, it is translated into the proteins needed to correct the cellular imbalance. From this view point gene therapy can be considered as a new way to deliver proteins into living cells.

The efficiency of the overall process is critical for achieving a therapeutic effect.[4] Viral vectors have been most frequently employed because they have a high efficiency,[5, 6] but they possess several major disadvantages such as immunogenicity, permanent integration of the foreign plasmid into the host's DNA, difficulties associated with GMP production or storage, and a limited size of the plasmid that can be inserted into the virion.[1-3]

Cationic lipids are a promising non-viral alternative, having low immunogenicity and cytotoxicity; they can involve plasmids with practically unlimited size, and they can be easily manufactured and stored in bulk quantities under GMP-compliant norms.[7-11] They are amphiphilic molecules that contain a polar (cationic) head linked via a spacer to a hydrophobic tail. When a certain concentration is reached, they can self-assemble, via cooperative hydrophobic intermolecular binding, forming cationic liposomes. In this form, cationic lipids can efficiently bind and compact DNA molecules by electrostatic association between the positively charged polar heads of the lipids and the negatively charged phosphate groups of the DNA, forming cationic lipid—DNA complexes (lipoplexes[12]).[13-15] The genetic material is protected from the action of nucleases and is thus able to reach the desired target cells. Similarly, cationic polymers can also associate and compact DNA, forming another type of chemical transfection systems—polyplexes.[12, 16]

The main problem associated with the therapeutic use of non-viral transfection systems is their lower efficiency, which amounts to a few percent from that achieved by viral vectors. Consequently, substantial efforts have been devoted to understanding these physiological barriers, their correlation with the chemical structure and physico-chemical properties of the lipoplexes, and the ways to overcome them.[7, 10] Despite the fact that a fairly large variety of commercial cationic lipid-based transfection systems are available nowadays (formulas 1-7), basic characteristics, such as in vivo efficiency and intrinsic cytotoxicity, remain to be improved.

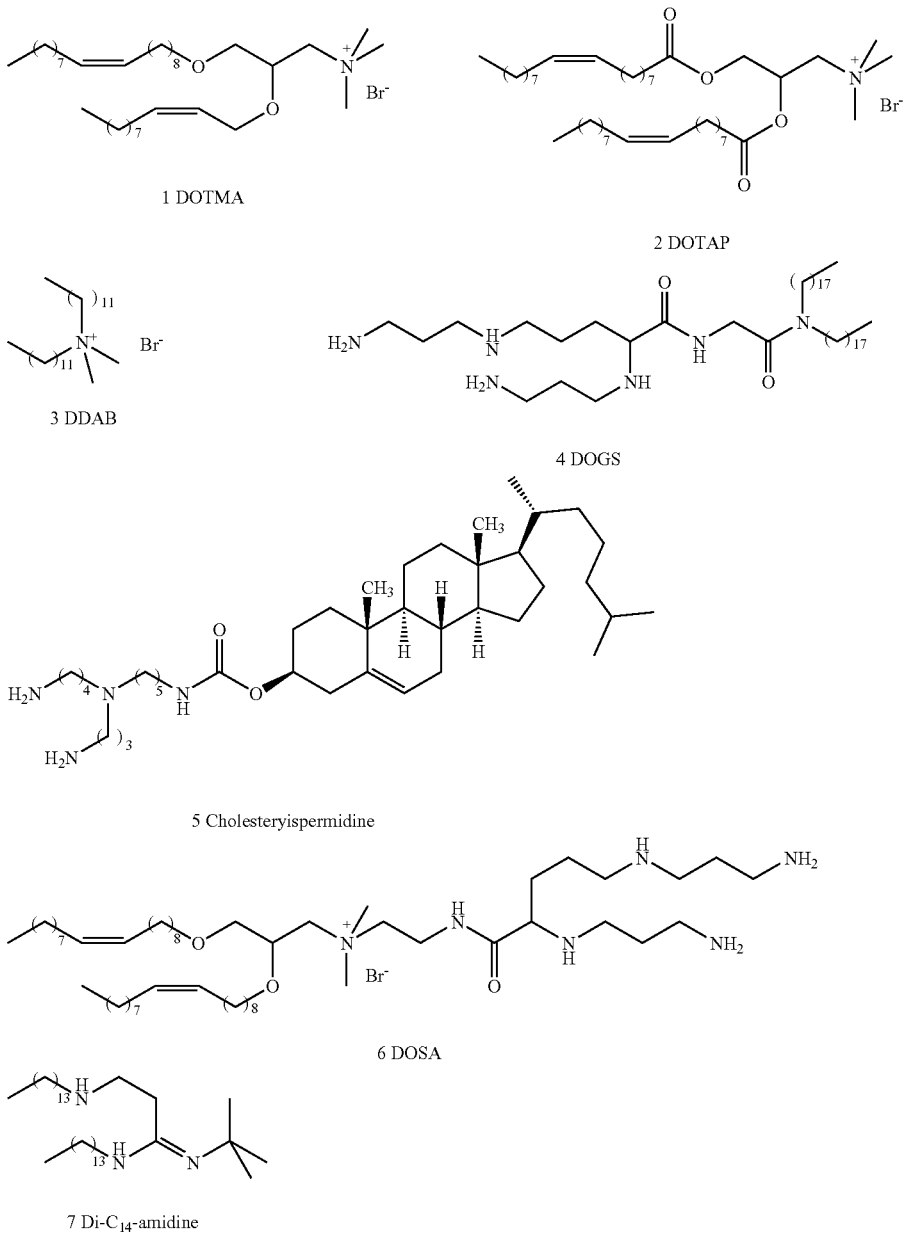

Only very few cytofectins with the positive charge on an aromatic heterocyclic ring have been described so far,[7, 8, 17-19] and practically all of them are either pro-cationic (i. e. amines that become protonated at the physiological pH), or are prepared via the quaternization of a preformed neutral nitrogen-containing aromatic ring, often followed by exchange of the anion (formulas 8-16). It is known that alkyltrimethylammonium cations can be cleaved because they may undergo a Hoffman degradation yielding an alkene and trimethylamine, but such a reaction is unlikely when the positively charged nitrogen atom is in a heterocyclic ring. Furthermore, positively charged aromatic heterocycles have planar rings with delocalized charge, a fact that can have a major impact on physico-chemical properties such as lipid hydration, supramolecular assembly, interaction with nucleosomes, etc. [7, 8] In this context, Engbert's group reported recently the cationic lipids 11-16, based on pyridinium polar heads.[18-20] Best results were obtained with oleyl and stearyl hydrophobic chains: the corresponding amphiphiles exhibited higher transfection efficiencies and a reduced cytotoxicity when compared with classical transfection systems such as 2,3-dioleoyloxypropyl-1-trimethylammonium bromide (DOTMA, 1). Insights regarding the mechanism of action of this class of compounds as well as a structure-activity relationship study have been recently disclosed.[21]

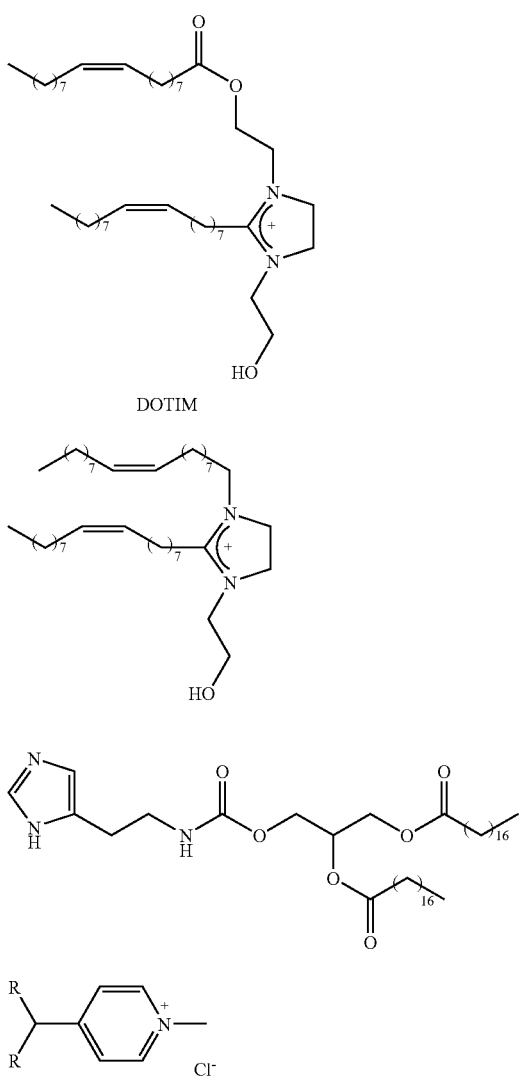

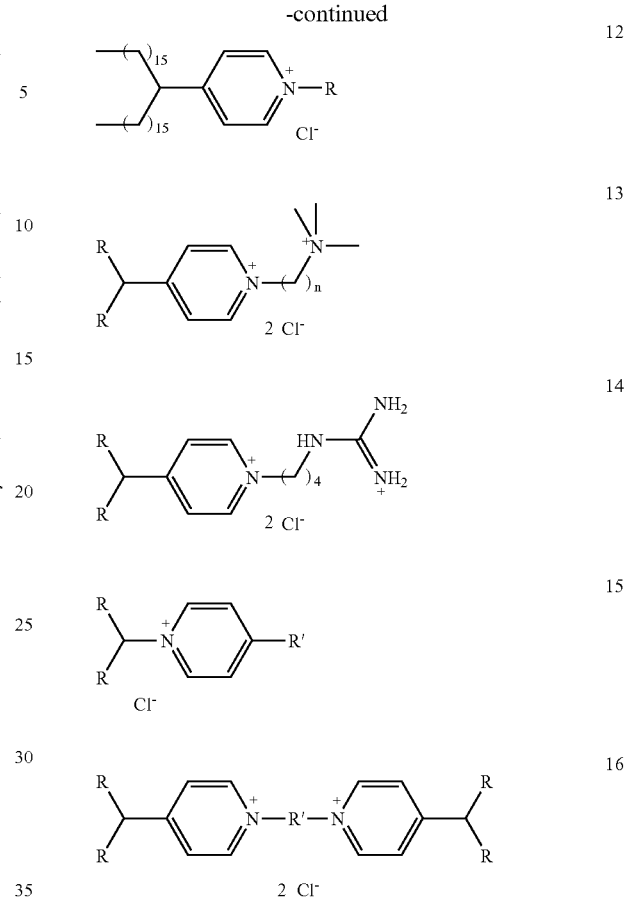

We report here new pyridinium cationic lipids obtained via a novel approach. Instead of starting from a neutral nitrogen-containing heterocyclic ring and quaternizing it with an alkylating agent, we have used a high-yield procedure to generate simultaneously the heterocyclic ring and the positively charged nitrogen atom, via pyrylium salts (17). A simple approach for obtaining pyrylium salts consists in the reaction of isobutene (generated in situ for t-butanol) with an excess of acylating agent (the diacylation of alkenes has been called the Balaban-Nenitzescu-Praill reaction).[22] Pyrylium salts react with primary amines (18 or 22) yielding pyridinium salts with high yields.[23, 24] Compounds 21a-c and 25a-c were obtained,[25] using different hydrophobic anchors connected by ester linkages, as shown below. This structure has therefore a polar head and a forked hydrophobic tail. Additionally, the pyridinium propanediols 19 and 23, as well as their acetate derivatives (compounds 20 and 24) were extensively studied in respect to their NMR spectra.

2. Results and Discussion 2.1 Synthesis and NMR Structural Assignments

In the first step the key diol intermediates 19 and 23 were synthesized from the corresponding aminopropanediols and trisubstituted pyrylium salts (Schemes 1 and 2). 2,4,6-Trimethylpyrylium and triphenylpyrylium salts (perchlorate or fluoroborate) [23, 24, 26] were prepared according to the literature.[27, 28]

Scheme 1
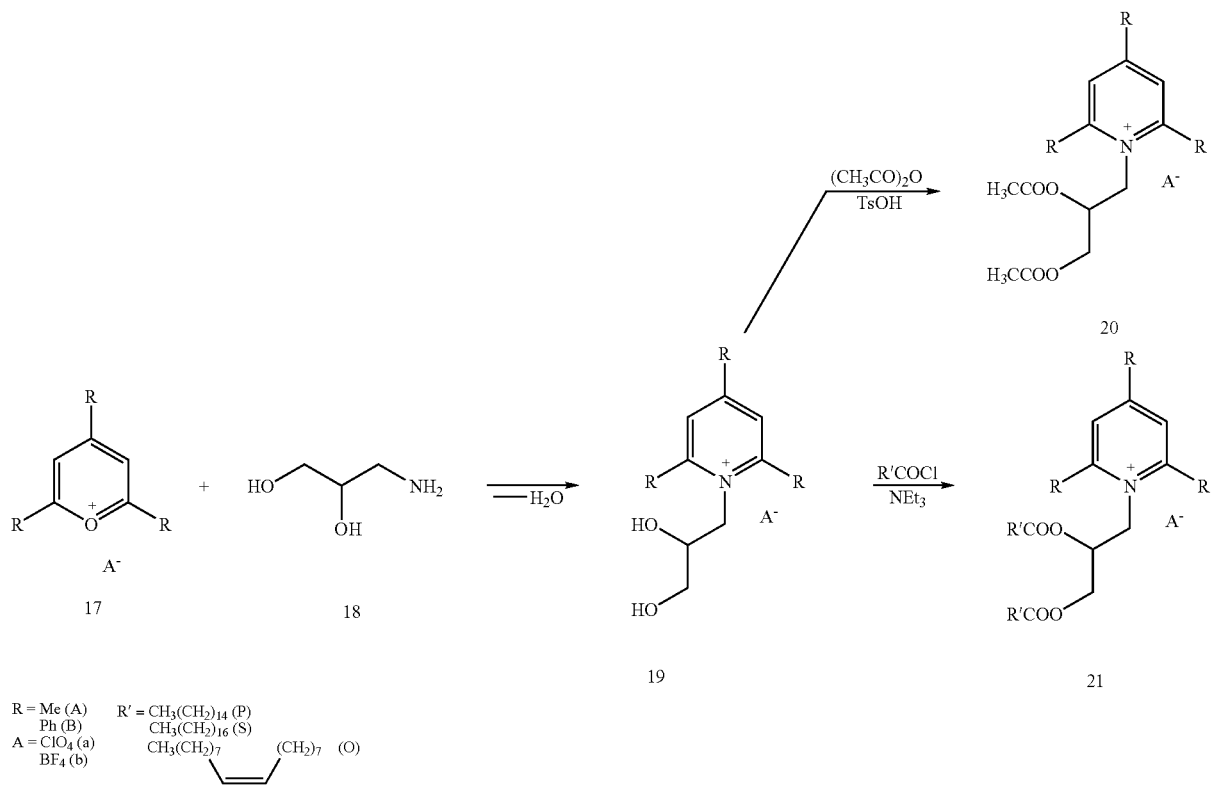
Scheme 2
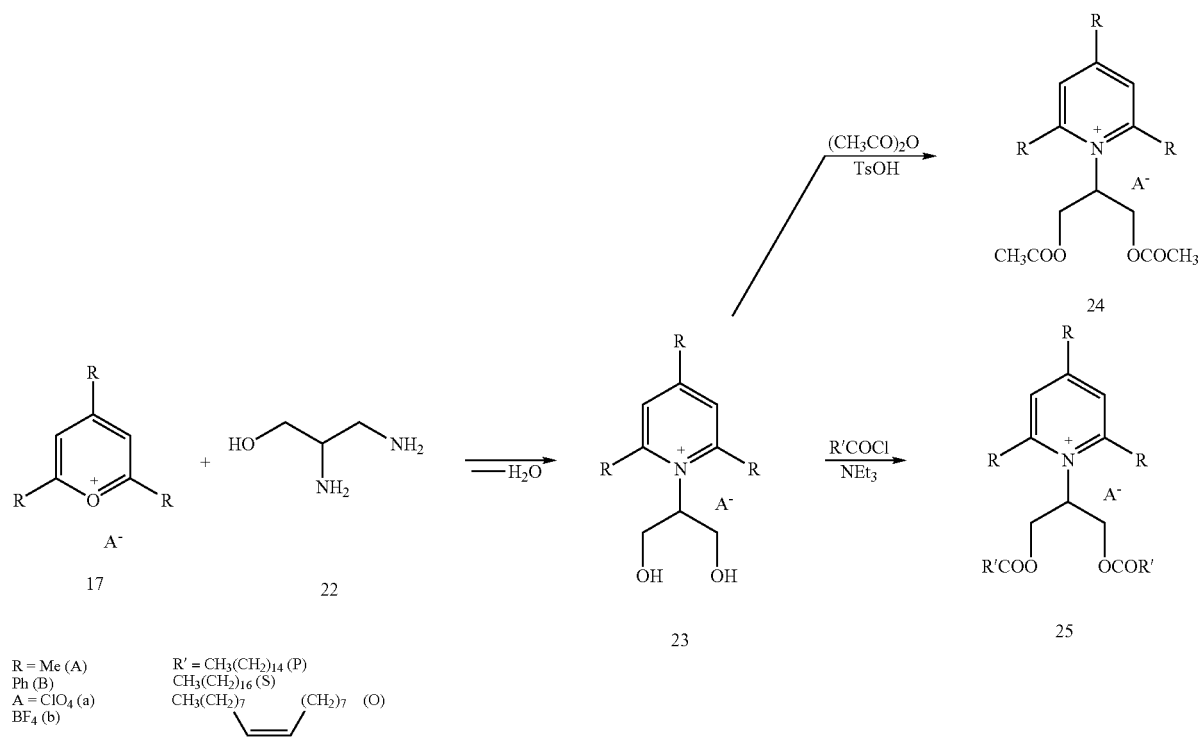

Despite different attempts, not all these intermediates could be obtained in crystalline form, remaining as viscous liquids. Interestingly, the behavior of the two types of pyridinium propanediols was different: in the series derived from 1-amino-2,3-propanediol only the trimethylpyridinium salts 19A crystallized, while in the series derived from 2-amino-1,3-propanediol (serinol) only the triphenylderivatives 23B were obtained in a crystalline form. The influence of the pyridinium rotor on the dihydroxypropyl backbone, as well as the association of the two hydroxymethylene groups by intramolecular and intermolecular hydrogen bonds was investigated in detail by means of NMR spectroscopy.

Data from tables 2 and 4 show that rotation of the substituted pyridinium ring around the Cl—N bond is partially restricted: both the $^{13}$C-NMR signals of α-quaternary carbon atoms and the α-methyl groups are broadened, and this feature is maintained in different deuterated solvents with different polarities. The existence of different "frozen" conformations can be also seen in the pattern of the pyridinium β-carbon signal, which appears with different multiplicities. Moreover, dynamic NMR spectrometry on the 1-pyridinium-2,3-propanediol 19Aa showed that when the temperature is raised all these signals sharpened; the coalescence temperature was found at about 318 K (45° C). This temperature corresponds to a rotational barrier of about 17-20 kcal/mol, in agreement with previous findings.[29, 30] The dynamic $^1$H-NMR and the use of trifluoroacetic acid as catalyst for accelerating proton exchange also evidenced the existence of an intramolecular hydrogen bond in this case. Because the pyridinium ring constitutes the polar head in the structure of the new cationic lipids, we further investigated its steric requirements by preparing the corresponding acetates, which are compounds with structures related to common designs of transfection vectors. The acetates were readily available via acetylation of diols 19 and 23 with acetic anhydride. The NMR data for all these compounds are summarized in tables 3 and 4. For acetates 20 or 24 the rotation of the pyridinium ring was found to be less restricted when compared to the parent diols.

A general feature in the $^1$H-NMR spectra of compounds 19 and 20 (derived from a 2,3-disubstituted backbone) is the larger geminal coupling constant $^2$J between the diastereotopic N—CH$_2$ protons (14.1-15.8 Hz) than between the diastereotopic O—CH$_2$ protons (11.0-12.3 Hz). This effect is better explained by the vicinity of π-electrons for the N—CH$_2$ protons, rather than by differences in bond angles or electronegativities of adjacent groups. Also, the large difference in the vicinal coupling constants between H—C2 and the two N—CH$_2$ protons (one $^3$J value of 2.7-4.8 Hz, and another of 8.8-9.8 Hz) is also due to the proximity of the aromatic ring. By contrast, the largest $^3$J values between H—C2 and the two O—CH$_2$ protons (4.0-6.7 Hz) are practically equal. Raising the temperature from 20° to 70° did not change these coupling constants; therefore one can exclude any effect of restricted rotations.

In the case of compounds 23 and 24 (derived from a 1,3-disubstituted backbone) the restricted rotation of the pyridinium ring generates the magnetic non-equivalence of the two constitutionally equivalent CH$_2$ groups. The differences between the geminal coupling constants of the enantiotopic CH$_2$ protons are reduced; these values appear in the range of 11.5-14.6 Hz. The vicinal coupling constants between H—C2 and the two groups of CH$_2$ protons are also different. The two α-methyl groups as well as the pyridinium β-protons are also magnetically non-equivalent; these facts are confirmed by the $^{13}$C-NMR spectra.

In the final step of the synthesis of the novel cationic lipids the diols 19 and 23 were condensed with palmitoyl, stearoyl, or oleoyl chloride in acetonitrile in the presence of the stoichiometric amount of triethylamine, similarly to the synthesis of N-[1-(2,3-dioleoyloxy)propyl]-N,N,N-trimethylammonium (DOTAP, 2).[31] The crude products were purified via flash chromatography to yield the final products 21 and 25 in pure form. The cationic lipids were extensively characterized by standard analytical and spectroscopic methods that confirmed the structures (see Tables 5, 6 and the experimental section). Mention must be made that owing to the perchlorate and tetrafluoroborate counterions, known to affect the process of combustion, the elemental analyses were done for nitrogen only. The transition temperatures ($T_c$) of the lipids were determined by differential scanning calorimetry (DSC).

The NMR spectra of cationic lipids are similar to the NMR spectra of corresponding acetates. From the $^1$H-NMR spectra of the oleoyl derivatives where no trans coupling constant was observed in the 5.5 ppm alkenic proton range, we infer that no cis-trans isomerization has taken place during the reaction.

Along with the 2,4,6-trimethylpyridinium derivatives, we obtained two 2,4,6-triphenyl-substituted pyridinium lipids by the same synthetic strategy (see experimental section for characterization). The presence of the 2,4,6-triphenylpyridinium moiety, which has a strong UV fluorescence and a more pronounced lipophilic character, generates the possibility to use these compounds as markers for bio-membrane studies.

2.2. Biological Assays

Transfection experiments were carried out in vitro on HeLa cells (human carcinoma cell line ATCC No. CCL-2), using a pGL3-Control plasmid (Promega, Madison, Wisc.), which encodes the firefly luciferase reporter. The structurally related and commercially available DOTAP (2) mentioned earlier was chosen as reference.

Figure 8:
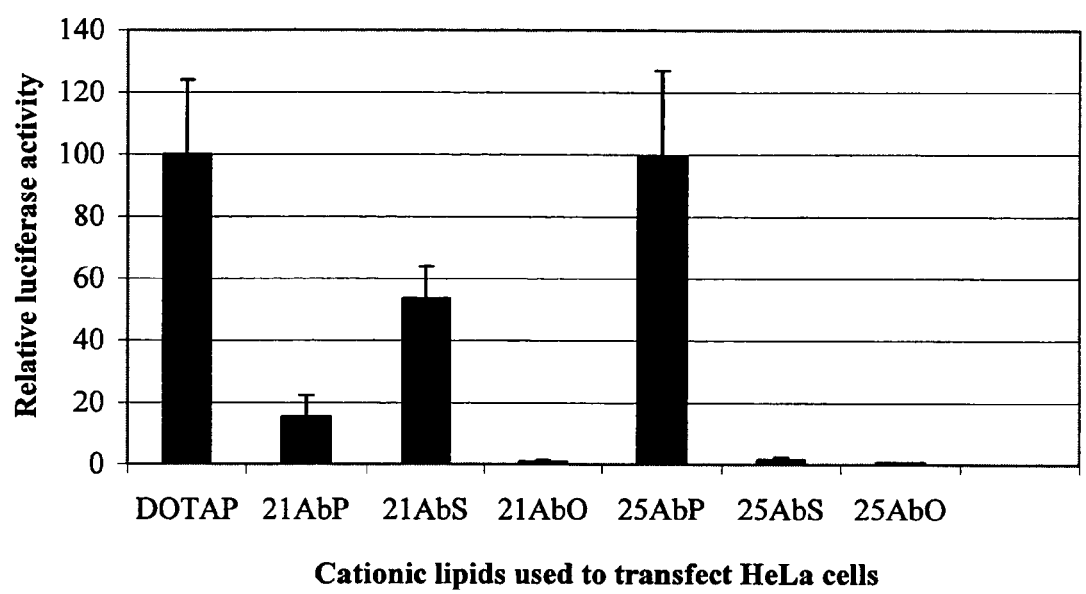
FIG. 8. Transfection efficiency of pyridinium tetrafluoroborate lipids 21Ab and 25Ab.

Good transfection efficiencies were obtained in the case of tetrafluoroborates 21 Ab and 25 Ab (FIG. 8). The perchlorates were practically devoid of any detectable biological effect in these specific assays. This fact might be due to inhibition of sulfation of proteoglycans as reported in the literature for the chlorate anion.[32] Compound 25AbP showed transfection efficiency comparable with that of DOTAP.

A very important parameter of the transfection assays is the cytotoxicity of the cationic vectors. Interestingly, the new cationic lipids exhibited a reduced cytotoxicity (20-50%) as compared with the DOTAP reference (60-75%). This finding agrees with the results of Engbert's group[18, 19] regarding the reduced cytotoxicity of pyridinium cationic lipids.

Two series of substituted pyridinium cationic lipids were synthesized via pyrylium precursors and long-chain fatty acid derivatives, and extensively characterized: 1-(2,3-diacyloxypropane-1-yl)-2,4,6-trimethylpyridinium and 1-(1,3-diacyloxypropane-2-yl)-2,4,6-trimethylpyridinium salts. The related acetates, derived from the same key diol intermediates, were also synthesized. A detailed NMR study, including dynamic NMR spectroscopy, was performed on all these compounds, for elucidating their structural particularities.

Biological assessment of the novel lipids showed transfection efficiencies that reached the level of commercial lipidic vectors but were less cytotoxic. Also, this strategy will allow the preparation of fluorescent lipids with possible application as membrane markers, as will be shown in a future paper.

Materials and Methods. Melting points for the diols, acetates and ketals were determined on a Boetius heating plate microscope and are uncorrected. For the cationic lipids 21 and 25 the phase transition temperature $T_c$ was determined by differential scanning calorimetry (DSC), using a TA-Instruments Q100 DSC, and a heating rate of 5° C./minute. The IR spectra were recorded on a Nicolet Avatar 360 FTIR spectrophotometer, in the range 650-4000 cm$^{-1}$, using a ZnSe—attenuated total reflectance (ATR) accessory. The compounds were solved in a small amount of solvent (MeOH for the diols, CHCl$_3$ for the esters), the resulted solutions being left to evaporate to dryness on the surface of the ZnSe crystals of the ATR accessory. This technique was imposed by the poor results obtained in transmission mode for some of the compounds, due to the lack of crystallization, hygroscopicity and other problems related with working with KBr pellets. The NMR spectra were recorded at ≈303 K with a Varian Gemini 300BB spectrometer operating at 300 MHz for $^1$H and at 75 MHz for $^{13}$C. Chemical shifts are reported as δ values, using TMS as internal standard for proton spectra and the solvent resonance for carbon spectra: 77.00 ppm in CDCl$_3$, 39.50 ppm in DMSO-d$_6$, the line from 123.50 ppm in pyridine-d$_5$, 62.80 ppm in nitromethane-d$_3$, 30.10 ppm in dimethylformamide-d$_7$. Assignments were made based on signal intensity, selective decoupling and COSY ($^1$H-$^1$H) and HETCOR ($^1$H-$^{13}$C) sequences. Nitrogen elemental analysis was performed by combustion, mixing the samples with small amounts of quartz sand.

Racemic 3-amino-1,2-propanediol was from Fluka, racemic 2-amino-1,3-propanediol hydrochloride was from Aldrich; triethylamine, acetic anhydride, acetic acid, acyl chlorides and other solvents were from Acros, Aldrich, Fluka and/or Merck. TLC was performed on silicagel 60-F$_{254}$ plates (from Merck), eluted with MeOH:CHCl$_3$ 20:80 (v/v). The pyrylium salts were prepared according to the literature.[23, 24] CAUTION: Since perchlorates may explode when they are heated or hit in dry form, they should be stored moist with water.

HeLa cell line was obtained from ATCC, MD. The plasmid pGL3-control, encoding a firefly luciferase reporter was from Promega (Madison, Wisc.). As transfection reference we used N-[1-(2,3-dioleoyloxy)propyl]-N,N,N-trimethylammonium methylsulfate (DOTAP), obtained from Roche Molecular Biochemicals (Indianapolis, Ind.). The BCA protein assay kit was from Pierce (Rockford, Ill.).

General Procedure for the Preparation of the Pyridinium Diols 19 and 23:

An amount of 10 mmoles of aminopropanediol was dissolved under stirring in 30 mL of anhydrous ethanol. When using the aminopropanediol hydrochloride, 10 mmol of freshly cut sodium was first stirred with the ethanol for yielding sodium ethoxide, the hydrochloride (10 mmol) was added in the resulted ethoxide solution, stirred for 15 minutes and filtered for separating the resulted sodium chloride. Next, the corresponding pyrylium salt (12 mmol of perchlorate, tetrafluoroborate) was added, followed immediately by the addition of 12 mmol of triethylamine. The resulted homogenous mixture was heated to reflux for 15 minutes, then 25 mmol of glacial acetic acid were added and the reflux was continued for 1-3 hours (TLC control). After this period, concentrated aqueous ammonia (2 mL) was added and the mixture was heated for 5 min in order to convert any unreacted pyrylium salt into the corresponding pyridine, which is soluble in diethyl ether. The final solution was cooled and poured under stirring into anhydrous diethyl ether (200-300 mL). The resulting insoluble heavier oily layer was separated and washed with two additional portions (20 mL each) of diethyl ether. After a final separation, the oily layer was taken in a few milliliters of hot isopropyl alcohol, treated with charcoal, filtered and allowed to cool slowly when crystallization occurred; if not, the resulted viscous oil was separated from the mother liquor, redissolved in the minimum amount of hot methanol or isopropanol, and the concentrated solution was allowed to cool. Sometimes, crystallization occurred only after a longer time, even in case of very pure compounds (but some of them could never be obtained in crystalline form). Yields were in the range of 50-80%. The products were recrystallized from methanol or isopropanol.

General Procedure for the Preparation of the Pyridinium Diacetates 20 and 24:

The N-(propanediol)-pyridinium salts 19 or 23 (5 mmol) was treated with 15 mL of acetic anhydride and a small amount of solid 4-toluenesulfonic acid. The mixture was heated to reflux for 10-30 minutes (TLC control), then allowed to cool and poured into 100 mL of anhydrous diethyl ether, when the desired product crystallized. If not, the oily product was washed with two additional portions (10 mL each) of diethyl ether, decanted, dissolved in the minimum amount of hot methanol or isopropanol, treated with charcoal, filtered and allowed to cool slowly when crystallization occurred. Yields varied from 55 to 88%. The products were recrystallized from methanol or isopropanol.

General Procedure for the Preparation of the Pyridinium Lipids 21 and 25:

The N-(propanediol)-pyridinium salts 19 or 23 (2 mmol) was dissolved under stirring in 15 mL anhydrous acetonitrile. Triethylamine (0.56 mL, 4 mmol) was added, followed by dropwise addition of acid chloride R'COCl (4.4 mmol) when the color became yellow, and triethylamine hydrochloride started to precipitate. After stirring at room temperature for 3 hours, the solution was refluxed for another 2 hours. The solvent was evaporated (rotavapor) under reduced pressure, and the residue was extracted with 15 mL of distilled water and 15 mL of chloroform. The aqueous layer was separated, extracted with 15 mL of chloroform, and discarded. The combined chloroform extracts were shaken with 15 mL of distilled water, dried over sodium sulfate, and evaporated under reduced pressure. Final purification was effected by flash chromatography on silica gel 60 (40-60 μM) with a solvent mixture of chloroform and methanol (80:20 v/v), followed by recrystallization form acetonitrile for perchlorates and hexafluorophosphates, or from n-hexane for tetrafluoroborates.

1-(2,3-Dihydroxypropyl)-2,4,6-trimethylpyridinium perchlorate 19Aa: m.p. 121-122° C.; NMR: see tables 1-4; IR (thin film on ZnSe ATR crystal), cm$^{-1}$: 1080 (ClO$_4^-$), 1480, 1577, 1640, 2927, 3484; Anal.: found N, 4.80%; calculated for C$_{11}$H$_{18}$NO$_2^+$ ClO$_4^-$ (FW=295.72): N, 4.74%.

1-(2,3-Dihydroxypropyl)-2,4,6-trimethylpyridinium tetrafluoroborate 19Ab: m.p. 96-97° C.; NMR: see tables 3 and 4; IR (cm$^{-1}$): 998, 1041, 1083, 1481, 1577, 1640, 2936, 3533; Anal.: found N, 5.05%; calculated for C$_{11}$H$_{18}$NO$_2^+$ BF$_4^-$ (FW=283.07): N, 4.95%.

1-(2,3-Dihydroxypropyl)-2,4,6-triphenylpyridinium perchlorate 19Ba: NMR: see tables 3 and 4; IR (cm$^{-1}$): 702, 767, 891, 1061 (ClO$_4^-$), 1562, 1599, 1618, 2936, 3476; Anal.: found N, 3.25%; calculated for C$_{26}$H$_{24}$NO$_2^+$ ClO$_4^-$ (FW=481.92): N, 2.91%.

1-(2,3-Dihydroxypropyl)-2,4,6-triphenylpyridinium tetrafluoroborate 19Bb: NMR: see tables 3 and 4; IR (cm$^{-1}$): 701, 767, 891, 1046, 1495, 1562, 1599, 1619, 2929, 3528; Anal.: found N, 3.32%; calculated for C$_{26}$H$_{24}$NO$_2^+$ BF$_4^-$ (FW=469.28): N, 2.98%.

1-(2,3-Diacetoxypropyl)-2,4,6-trimethylpyridinium perchlorate 20Aa: mp 128-129° C.; NMR: see tables 3 and 4; IR (cm$^{-1}$): 1084 (CiO$_4^-$), 1371, 1577, 1640, 1743, 2948; Anal.: found N, 3.74%; calculated for C$_{15}$H$_{22}$NO$_4^+$ ClO$_4^-$ (FW=379.79): N, 3.69%.

1-(2,3-Diacetoxypropyl)-2,4,6-trimethylpyridinium tetrafluoroborate 20Ab: mp 119-120° C.; NMR: see tables 3 and 4; IR (cm$^{-1}$): 1026, 1035, 1061, 1216, 1577, 1641, 1743, 2993; Anal.: found N, 3.80%; calculated for C$_{15}$H$_{22}$NO$_4^+$ BF$_4^-$ (FW=367.14): N, 3.81%.

1-(2,3-Diacetoxypropyl)-2,4,6-triphenylpyridinium perchlorate 20Ba: NMR: see tables 3 and 4; IR (cm$^{-1}$): 704, 749, 892, 1090 (ClO$_4^-$), 1215, 1561, 1599, 1620, 1745; Anal.: found N, 2.82%; calculated for C$_{30}$H$_{28}$NO$_4^+$ ClO$_4^-$ (FW=566.00): N, 2.47%.

1-(2,3-Diacetoxypropyl)-2,4,6-triphenylpyridinium tetrafluoroborate 20Bb: NMR: see tables 3 and 4; IR (cm$^{-1}$): 700, 766, 891, 1042, 1224, 1495, 1561, 1599, 1620, 1737; Anal.: found N, 2.78%; calculated for C$_{30}$H$_{28}$NO$_4^+$ BF$_4^-$ (FW=553.35): N, 2.53%.

1-(2,3-Dipamitoyloxypropyl)-2,4,6-trimethylpyridinium perchlorate 21AaP: T$_c$: 106° C.; NMR: see tables 5 and 6; IR (cm$^{-1}$): 1085 (CiO$_4^-$), 1370, 1577, 1643, 1745, 2860, 2930; Anal.: found N, 1.68%; calculated for C$_{43}$H$_{78}$NO$_4^+$ ClO$_4^-$ (FW=772.53): N, 1.81%.

1-(2,3-Distearoyloxypropyl)-2,4,6-trimethylpyridinium perchlorate 21AaS: T$_c$: 110° C.; NMR: see tables 5 and 6; IR (cm$^{-1}$): 1084 (ClO$_4^-$), 1371, 1578, 1642, 1744, 2861, 2938; Anal.: found N, 1.50%; calculated for C$_{47}$H$_{86}$NO$_4^+$ ClO$_4^-$ (FW=828.64): N, 1.69%.

1-(2,3-Dioleoyloxypropyl)-2,4,6-trimethylpyridinium perchlorate 21AaO: T$_c$: 57° C.; NMR: see tables 5 and 6; IR (cm$^{-1}$): 1084 (ClO$_4^-$), 1370, 1578, 1640, 1664, 1743, 2850, 2938, 3024; Anal.: found N, 1.38%; calculated for C$_{47}$H$_{82}$NO$_4^+$ ClO$_4^-$ (FW=824.61): N, 1.70%.

1-(2,3-Dipamitoyloxypropyl)-2,4,6-trimethylpyridinium tetrafluoroborate 21AbP: T$_c$: 100° C.; NMR: see tables 5 and 6; IR (cm$^{-1}$): 1026, 1035, 1061, 1216, 1578, 1643, 1743, 2860, 2940; Anal.: found N, 1.75%; calculated for C$_{43}$H$_{78}$NO$_4^+$ BF$_4^-$ (FW=759.89): N, 1.84%.

1-(2,3-Distearoyloxypropyl)-2,4,6-trimethylpyridinium tetrafluoroborate 21AbS: T$_c$: 103° C.; NMR: see tables 5 and 6; IR (cm$^{-1}$): 1025, 1034, 1064, 1216, 1577, 1643, 1743, 2860, 2943; Anal.: found N, 1.58%; calculated for C$_{47}$H$_{86}$NO$_4^+$ BF$_4^-$ (FW=815.99): N, 1.72%.

1-(2,3-Dioleoyloxypropyl)-2,4,6-trimethylpyridinium tetrafluoroborate 21AbO: T$_c$: 52° C.; NMR: see tables 5 and 6; IR (cm$^{-1}$): 1084, 1371, 1577, 1640, 1666, 1743, 2864, 2948; 3024 Anal.: found N, 1.50%; calculated for C$_{47}$H$_{82}$NO$_4^+$ BF$_4^-$ (FW=811.96): N, 1.73%.

1-(2,3-Dipalmitoyloxypropyl)-2,4,6-triphenylpyridinium perchlorate 21BaP. T$_c$: 134° C.; $^1$H-NMR (CDCl$_3$), δ, ppm: 7.91 (s, 2H, Hβ pyridinium) 7.79 (m, J=1.5, 8.1 Hz, 2H: Hα from phenylα), 7.5-7.7 (m, 13H: H from phenyl groups), 5.03 (m, J=4.7, 12.2 Hz, 3H: CH$_2$—N+CH), 3.77 (dd, J=3.9, 12.2 Hz, 1H: H$_A$ from CH$_2$—O), 3.45 (dd, J=3.9, 12.2 Hz, 1H: H$_B$ from CH$_2$—O), 2.30 (t, J=7.5 Hz, 1H: H$_A$ from 2-COCH$_2$), 2.22 (dt, J=7.4, 7.4, 16.1 Hz, 1H: H$_A$ from 3-COCH$_2$), 2.08 (dt, J=7.4, 7.4, 16.1 Hz, 1H: H$_B$ from 3-COCH$_2$), 1.63 (qnt, J=7.4 Hz, 2H: 2-COCH$_2$CH$_2$), 1.42 (qnt, J=7.4 Hz, 2H: 3-COCH$_2$CH$_2$), 1.10-1.38 (m, 48H: 24 CH$_2$ from fatty chains), 0.88 (t, J=6.7, 6H: 2 CH$_3$ from fatty chains); $^{13}$C-NMR (CDCl$_3$), δ, ppm: 172.52 (2-CO), 172.47 (3-CO), 157.63 (Cγ pyridinium), 156.54 (2Cα pyridinium), 133.61, 132.67, 132.51, 131.36, 129.80, 129.58, 129.49, 128.12, 127.40 (all from phenylic substituents of pyridinium ring) 126.61 (2Cβ pyridinium), 68.88 (CH), 61.62 (O—CH$_2$), 54.45 (N—CH$_2$), 34.10, 33.93, 33.53, 31.90, 29.66, 29.57, 29.48, 29.42, 29.34, 29.23, 29.13, 29.03, 24.95, 24.62, 24.52, 22.67 (all from fatty chains), 14.09 (2CH$_3$ from fatty chains); IR (cm$^{-1}$): 722, 856, 930, 1098 (ClO$_4^-$), 1170, 1239, 1378, 1413, 1440, 1574, 1637, 1695, 2853, 2930, 2980, 3001; Anal.: found N, 1.60%; calculated for C$_{58}$H$_{84}$NO$_4^+$ ClO$_4^-$ (FW=958.74): N, 1.46%.

1-(1,3-Dihydroxypropane-2-yl)-2,4,6-trimethylpyridinium perchlorate 23Aa: NMR: see tables 3 and 4; IR (cm$^{-1}$): 1090 (ClO$_4^-$), 1481, 1574, 1640, 3490; Anal.: found N, 5.02%; calculated for C$_{11}$H$_{18}$NO$_2^+$ ClO$_4^-$ (FW=295.72): N, 4.74%.

1-(1,3-Dihydroxypropane-2-yl)-2,4,6-trimethylpyridinium tetrafluoroborate 23Ab: NMR: see tables 3 and 4; IR (cm$^{-1}$): 1036, 1055, 1224, 1572, 1635, 3483; Anal.: found N, 5.27%; calculated for C$_{11}$H$_{18}$NO$_2^+$ BF$_4^-$ (FW=283.07): N, 4.95%.

1-(1,3-Dihydroxypropane-2-yl)-2,4,6-triphenylpyridinium perchlorate 23Ba: m.p. 197-198° C.; NMR: see tables 3 and 4; IR (cm$^{-1}$): 702, 764, 891, 1100 (ClO$_4^-$), 1494, 1561, 1598, 1618, 3473; Anal.: found N, 3.14%; calculated for C$_{26}$H$_{24}$NO$_2^+$ ClO$_4^-$ (FW=481.92): N, 2.91%.

1-(1,3-Dihydroxypropane-2-yl)-2,4,6-triphenylpyridinium tetrafluoroborate 23Bb: m.p. 232-234° C.; NMR: see tables 3 and 4; IR (cm$^{-1}$): 702, 764, 890, 1493, 1561, 1598, 1618, 3232; Anal.: found N, 3.15%; calculated for C$_{26}$H$_{24}$NO$_2^+$ BF$_4^-$ (FW=469.28): N, 2.98%.

1-(1,3-Diacetoxypropane-2-yl)-2,4,6-trimethylpyridinium perchlorate 24Aa: mp 111-112° C.; NMR: see tables 3 and 4; IR (cm$^{-1}$): 1091 (ClO$_4^-$), 1223, 1572, 1638, 1743; Anal.: found N, 3.65%; calculated for C$_{15}$H$_{22}$NO$_4^+$ ClO$_4^-$ (FW=379.79): N, 3.69%.

1-(1,3-Diacetoxypropane-2-yl)-2,4,6-trimethylpyridinium tetrafluoroborate 24Ab: mp 110-111° C.; NMR: see tables 3 and 4; IR (cm$^{-1}$): 1034, 1055, 1222, 1573, 1637, 1743; Anal.: found N, 3.86%; calculated for C15H$_{22}$NO$_4^+$ BF$_4^-$ (FW=367.14): N, 3.81%.

1-(2,3-Diacetoxypropane-2-yl)-2,4,6-triphenylpyridinium perchlorate 24Ba: mp 201-202° C.; NMR: see tables 3 and 4; IR (cm$^{-1}$): 704, 766, 892, 1045, 1092 (ClO$_4^-$), 1220, 1494, 1562, 1598, 1620, 1746; Anal.: found N, 2.43%; calculated for C$_{30}$H$_{28}$NO$_4^+$ ClO$_4^-$ (FW=566.00): N, 2.47%.

1-(2,3-Diacetoxypropane-2-yl)-2,4,6-triphenylpyridinium tetrafluoroborate 24Bb: NMR: see tables 3 and 4; IR (cm$^{-1}$): 704, 765, 891, 1042, 1220, 1561, 1598, 1618, 1742; Anal.: found N, 2.84%; calculated for C$_{30}$H$_{28}$NO$_4^+$ BF$_4^-$ (FW=553.35): N, 2.53%.

1-(1,3-Dipamitoyloxypropane-2-yl)-2,4,6-trimethylpyridinium perchlorate 25AaP: T$_c$: 66° C.; NMR: see tables 5 and 6; IR (cm$^{-1}$): 1089 (ClO$_4^-$), 1374, 1580, 1640, 1747, 2863, 2931; Anal.: found N, 1.73%; calculated for C$_{43}$H$_{78}$NO$_4^+$ ClO$_4^-$ (FW=772.53): N, 1.81%.

1-(1,3-Distearoyloxypropane-2-yl)-2,4,6-trimethylpyridinium perchlorate 25AaS: T$_c$: 70° C.; NMR: see tables 5 and 6; IR (cm$^{-1}$): 1084 (ClO$_4^-$), 1375, 1580, 1640, 1747, 2860, 2940; Anal.: found N, 1.43%; calculated for C$_{47}$H$_{86}$NO$_4^+$ ClO$_4^-$ (FW=828.64): N, 1.69%.

1-(1,3-Dioleoyloxypropane-2-yl)-2,4,6-trimethylpyridinium perchlorate 25AaO: T$_c$: 48° C.; NMR: see tables 5 and 6; IR (cm$^{-1}$): 1088 (ClO$_4^-$), 1375, 1580, 1640, 1675, 1743, 2855, 2935, 3021; Anal.: found N, 1.41%; calculated for C$_{47}$H$_{82}$NO$_4^+$ ClO$_4^-$ (FW=824.61): N, 1.70%.

1-(1,3-Dipamitoyloxypropane-2-yl)-2,4,6-trimethylpyridinium tetrafluoroborate 25AbP: T$_c$: 70° C.; NMR: see tables 5 and 6; IR (cm$^{-1}$): 1025, 1039, 1061, 1217, 1578, 1640, 1745, 2863, 2940; Anal.: found N, 1.71%; calculated for C$_{43}$H$_{78}$NO$_4^+$ BF$_4^-$ (FW=759.89): N, 1.84%.

1-(1,3-Distearoyloxypropane-2yl)-2,4,6-trimethylpyridinium tetrafluoroborate 25AbS: $T_c$: 73° C.; NMR: see tables 5 and 6; IR (cm$^{-1}$): 1022, 1035, 1063, 1217, 1575, 1641, 1742, 2863, 2943; Anal.: found N, 1.42%; calculated for $C_{47}H_{86}NO_4^+$ $BF_4^-$ (FW=815.99): N, 1.72%.

1-(1,3-Dioleoyloxypropane-2-yl)-2,4,6-trimethylpyridinium tetrafluoroborate 25AbO: $T_c$: 43° C.; NMR: see tables 5 and 6; IR (cm$^{-1}$): 1082, 1370, 1574, 1640, 1665, 1740, 2862, 2948; 3025 Anal.: found N, 1.43%; calculated for $C_{47}H_{82}NO_4^+$ $BF_4^-$ (FW=811.96): N, 1.73%.

1-(1,3-Dipalmitoyloxypropane-2-yl)-2,4,6-triphenylpyridinium perchlorate 25BaP.: $T_c$: 125° C.; $^1$H-NMR (CDCl$_3$), δ, ppm: 7.90 (vbs, 2H: Hβ pyridinium); 7.78 (m, J=1.5, 8.1 Hz, 2H: Hα phenyls-α), 7.43-7.7 (m, 13H from phenyls), 5.30 (t, J=6.7 Hz, 1H: CH), 4.45 (dd, J=6.8, 12.2, 2H: 1-CH$_2$—O), 4.03 (dd, J=6.6, 12.2 Hz, 2H: 3-CH$_2$—O), 2.18 (dt, J=7.5 Hz, 2H: 1-COCH$_2$), 2.17 (t, J=7.5 Hz, 2H: 3-CO CH$_2$), 1.46 (qnt, J=7.4 Hz, 4H: 2 COCH$_2$CH$_2$), 1.15-1.36 (m, 48H: 24 CH$_2$ from fatty chains), 0.88 (t, J=6.7 Hz, 6H: 2CH$_3$ from fatty chains), $^{13}$C-NMR (CDCl$_3$), δ, ppm: 172.30 (2CO), 156.50 (broad, Cγ pyridinium), 156.32 (2Cα pyridinium), 133.47, 132.21, 131.34, 129.64, 129.44, 128.97, 128.93, 128.80, 128.39 (all from Ph substituents of pyridinium), 127.0 (very broad, Cβ pyridinium), 66.09 (CH), 62.59 (2 CH$_2$ propane), 42.64, 33.84, 33.49, 31.77, 29.54, 29.49, 29.45, 29.27, 29.21, 29.11, 29.03, 28.96, 28.86, 27.33, 24.66, 24.47, 23.74, 22.53 (all from CH$_2$ from fatty chains), 13.96 (2CH$_3$ from fatty chains); IR (thin film on ZnSe ATR crystal), cm$^{-1}$: 724, 874, 932, 1098 (ClO$_4^-$), 1173, 1242, 1384, 1415, 1443, 1567, 1642, 1690, 2850, 2932, 2980, 3010; Anal.: found N, 1.58%; calculated for $C_{58}H_{84}NO_4^+$ ClO$_4^-$ (FW=958.74): N, 1.46%.

Transfection Experiments

Assay Designed to Measure Transfection Efficiency

All of the pyridinium cationic lipids, along with the DOTAP reference, were tested in triplicate in two independent assays. The pyridinium cationic lipids containing tetrafluoroborate (BF$_4^-$) or perchlorate (ClO$_4^-$) anion were dissolved in ethanol/chloroform. The lipid solution was evaporated to dryness using a Speedvac rotary evaporating device, under vacuum. Traces of solvents were removed from the lipid film by keeping the vials under vacuum for another 3 hours. Ultrapure water was added to the dry lipid film, so that a final 1 μg/μL concentration could be reached, and the lipid film was allowed to hydrate overnight. The next day it was sonicated in an ultrasonic bath for 15 minutes in order to generate the liposomes. A solution containing 1.5 μg of DNA was prepared by mixing 0.8 μg of pGL3-Control plasmid DNA and 0.7 μg of sonicated salmon sperm DNA in cell culture medium. In a separate tube, 9 μL of liposome solution was diluted in 21 μL of cell culture medium and was added to the vial containing the DNA. After incubation for 20 minutes at room temperature, the lipoplex mixture was diluted in the cell culture medium to a final volume of 0.5 mL then added directly to a single 16 mm tissue culture dish containing approximately 7000 HeLa cells. After a 4 hour incubation at 37° C. in 5% CO$_2$, the lipid:DNA mixture was removed from the cells and replaced with fresh cell culture medium. Cells were harvested 28 hours post-transfection.

Procedure Used to Measure Luciferase Activity

Luciferase assays were conducted using reagents manufactured by Promega (Madison, Wisc.). Cell extracts were prepared by adding cell lysis buffer to each dish of HeLa cells. A dish of HeLa cells represented a sample. An aliquot from each sample was mixed with luciferin to measure luciferase activity in an Automat luminometer (EG&G Company, Gaithersburg, Md.). The total amount of protein present in each sample was used to normalize the luciferase activity. The normalized luciferase activity for each pyridinium cationic lipid was divided by the value for the DOTAP reference to calculate the relative luciferase activity.

Cytotoxicity Determinations

The determination of cytotoxicity was effected by counting under the microscope the number of dead cells post-transfection in three sets of experiments.

A further aspect of the present invention is a method of synthesizing pyridinium cationic lipids by reacting pyrylium salts with primary amines.

Described herein are pyridinium cationic lipids useful as transfection agents for gene therapy. The cationic lipids have the general formula I:

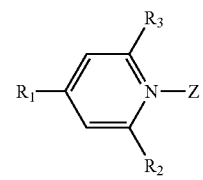

where $R_1$, $R_2$, $R_3$, and Z are as identified above. Also described herein is a method for synthesizing pyridinium cationic lipids by reacting a pyrylium salts with primary amines. The synthetic methods described herein comprise the reaction:

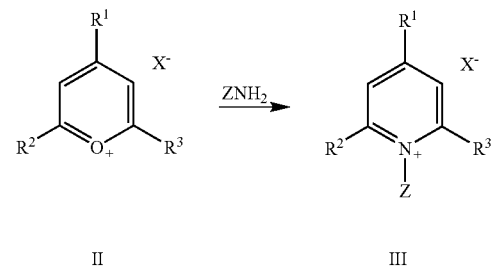

where II is a pyrylium and the product of the reaction III can undergo further chemical manipulation as described below to yield a cationic lipid of formula I.

Attachment Via an Aromatic Diphenolic Ring

A pyrylium salt obtained by diacylation of alkenes such as 2,4,6-trimethylpyrylium hexafluorophosphate, tetrafluoroborate, trifluoromethanesulfonate or halide (1) reacts with a primary aromatic dihydroxy-amine (2) such as dopamine (3-hydroxytyramine) (n=2 in the formulas below), to yield a pyridinium salt with two phenolic hydroxy groups (3) which can then be diacylated (R being a long-chain acyl group) or dialkylated (R=linear alkyl) to afford a cationic lipid (4).

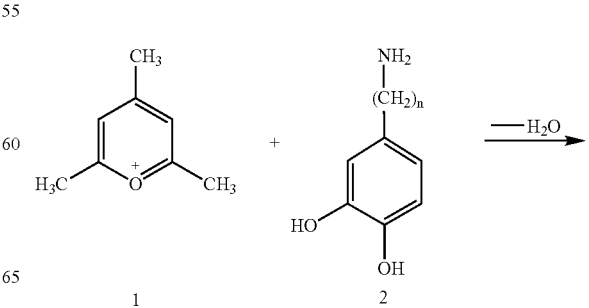

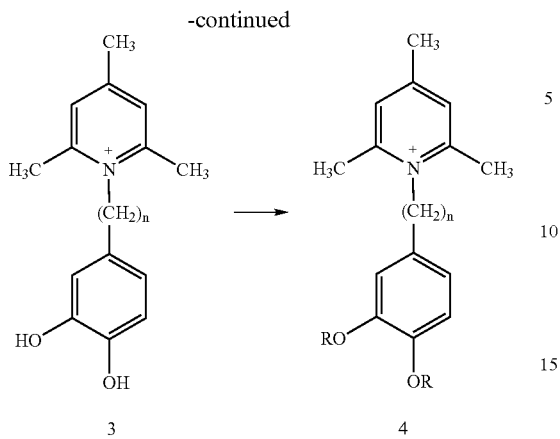

3,4-Dihydroxybenzylamine (2, n=1) in protic media is prone to splitting of the exocyclic C—N bond affording sym-collidine and a resonance-stabilized benzylic cation. 3,4-Dihydroxyaniline (2, n=0) is so readily oxidizable that it requires handling in an oxygen-free atmosphere.

Attachment Via a Tertiary Amino Group

A pyrylium salt such as 2,4,6-trimethylpyrylium hexafluorophosphate, tetrafluoroborate, trifluoromethanesulfonate or halide (1) reacts with a tertiary amine having two hydrophobic chains and also a primary amino group to yield a pyridinium salt 7 or 9 which are cationic lipids. The two hydrophobic chains can be linear alkyl groups as indicated in the bottom formulas (8 or 9, with n=2 and m=7 through 17). Alternatively, as indicated in the top formulas, one can form two hydrophobic chains by starting from N,N-dihydroxyethyl-ethylenediamine (5, m=n=2) and after the formation of the pyridinium salt 6 with two alcoholic groups, these groups may be acylated or alkylated with long linear chains having 8 to 18 carbon atoms yielding the cationic lipid 7 with ester or ether groups, respectively.

A pyridinium salt 9 can also be prepared from 1 with an equimolar amount of ethylenediamine, followed by dialkylating the resulting N-(2-aminoethyl)-2,4,6-trimethylpyridinium salt with two moles of a long-chain alkyl halide or tosylate. However, tertiary amines such as 8 with n=2 can be obtained by direct dialkylation of the corresponding diamine. In the case of N,N-dialkylhydrazines (8, n=0) the dialkylation of hydrazine also favors the N,N-dialkylhydrazine versus the N,N'-dialkylhydrazine. Unlike the compounds 7 or 9 with n=0 that become protonated at the tertiary amino group to dications at physiological pH values, the corresponding hydrazine derivatives (9, n=0) cannot become protonated.

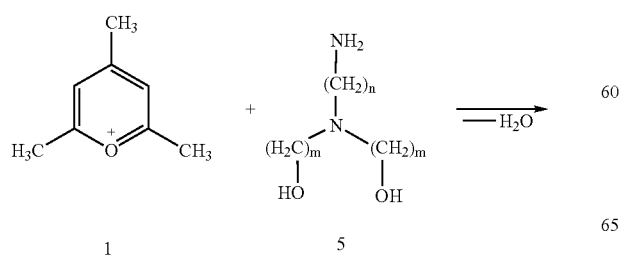

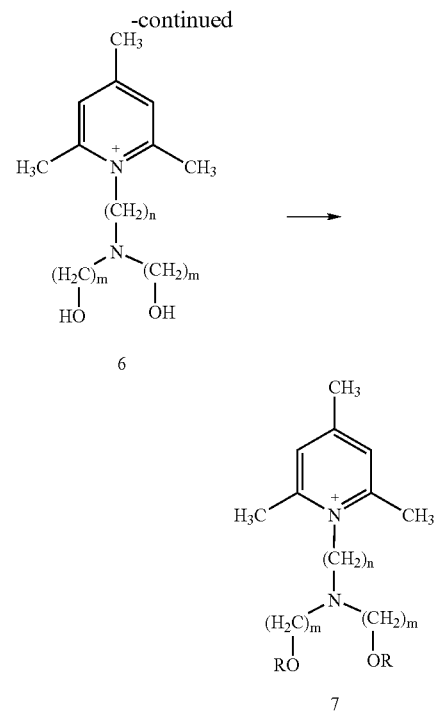

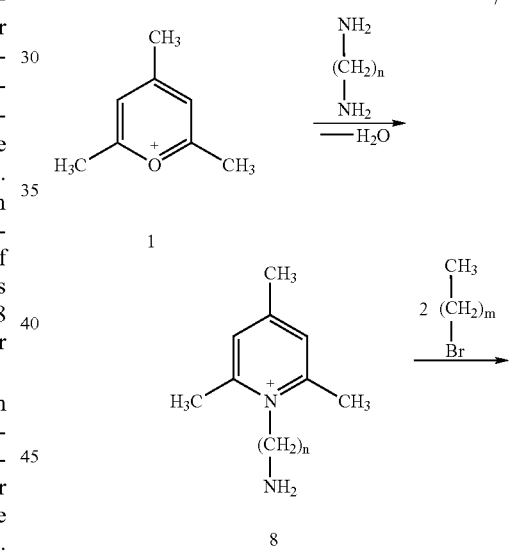

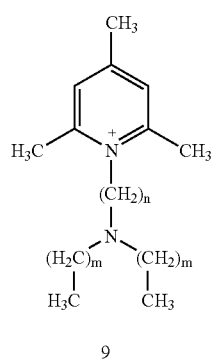

Attachment of Two (C-alkyl and N-alkyl) Linear Chains

A pyrylium salt 10 obtained by monoacylation of mesityl oxide such as 2-alkyl-4,6-dimethylpyrylium trifluoromethanesulfonate, hexafluorophosphate, tetrafluoroborate or halide having an alkyl group with n=9 through 17 reacts with an aliphatic primary amine 11 having a long alkyl chain (m=9 through 17) or with a para-substituted alkylaniline 13 with m=7 through 15 to yield cationic lipids 12 or 13.

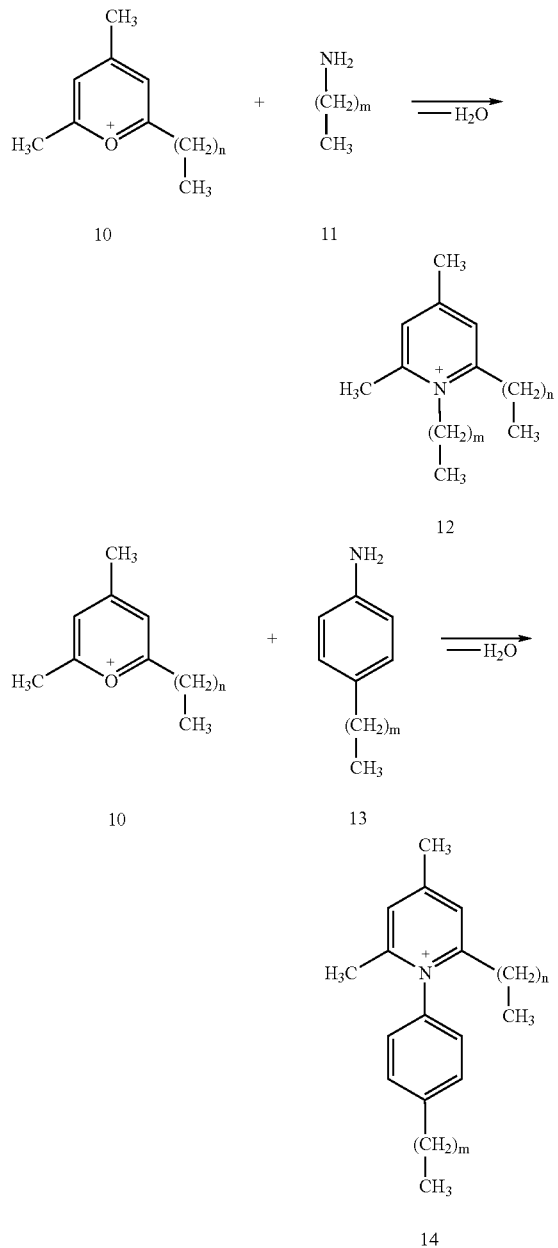

The primary amine may also contain a para-substituted aromatic ring with a long linear alkyl group and a benzylaminic or 2-aminoethyl group.

Attachment Via a Diamine

Two moles of a pyrylium salt 10 obtained by monoacylation of mesityl oxide such as 2-alkyl-4,6-dimethylpyrylium trifluoromethanesulfonate, hexafluorophosphate, tetrafluoroborate or halide having an alkyl group with n=9 through 17 reacts with one mole of an aliphatic primary diamine 15 (m=2 through 6) to yield a "gemini" dicationic lipid 16.

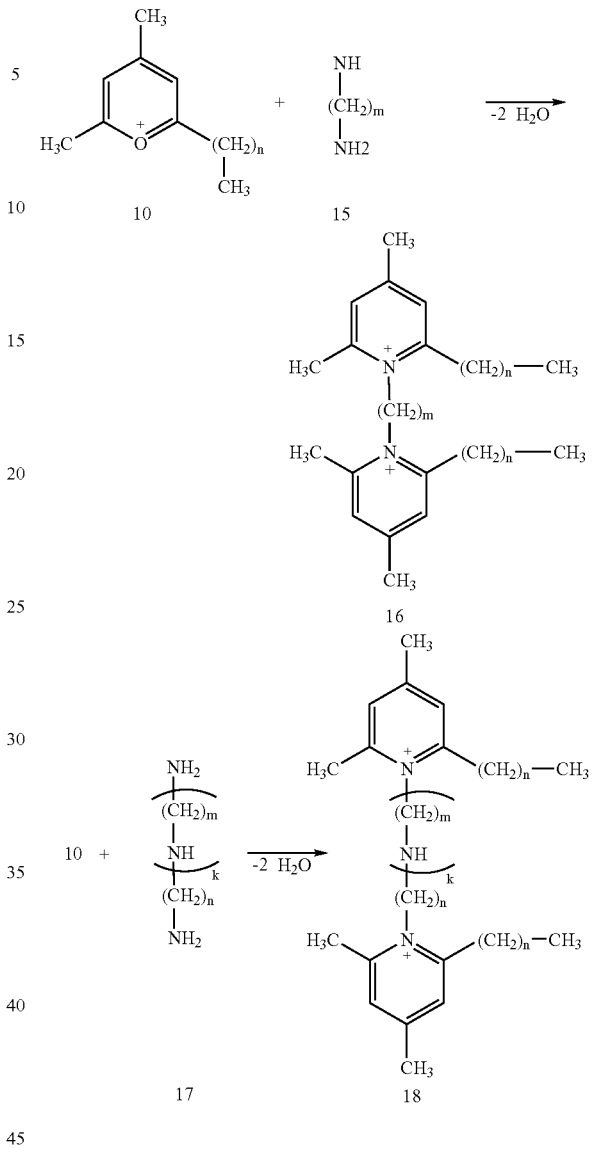

Figure 12:
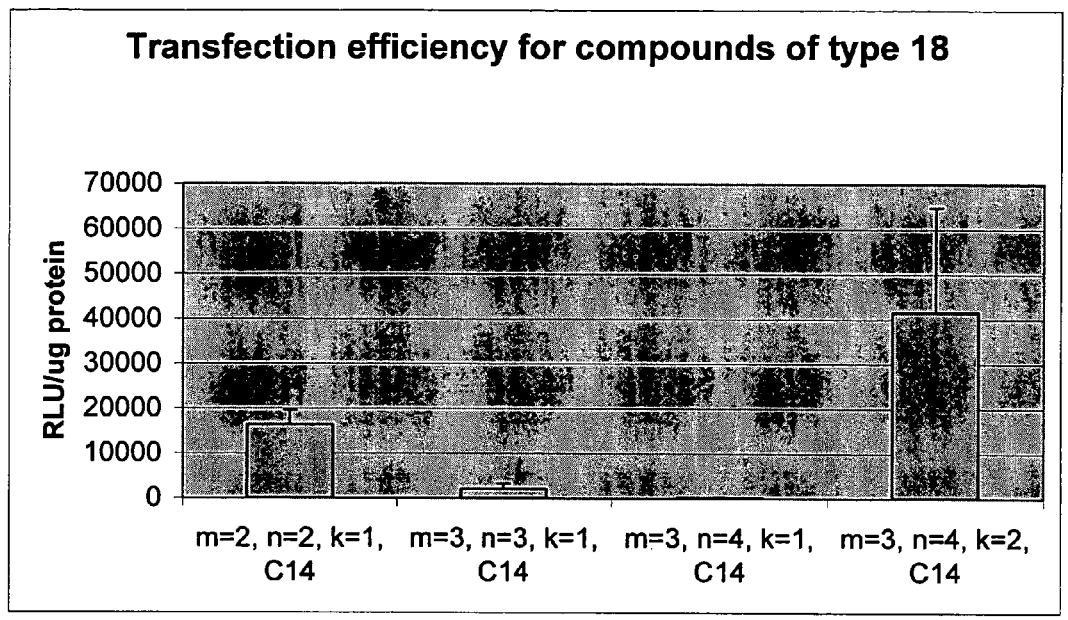
FIG. 12. Transfection data for polycationic lipids of type 18 (conditioned with cholesterol as co-lipid, at 1:1 molar ratio), on NCI-H23 tumor cell line.

If the diamine 17 has additional secondary amino groups such as in diethylene-triamine (m=n=2, k=1) or in spermidine (m=3, n=4, k=1), then a similar bis-pyridinium salt 18 results; in such cases the secondary amino groups become protonated at physiological pH values, and the resulting polycationic lipids compacts DNA efficiently (see FIG. 12). Similarly, 10 reacts with triethylene-tetramine (17, m=n=2, k=2) or with spermine (diamines that have two secondary amino groups).

Attachment Via Hydroxy-amines or Thiol-amines

A pyrylium salt 10 obtained by monoacylation of mesityl oxide such as 2-alkyl-4,6-dimethylpyrylium trifluoromethanesulfonate, hexafluorophosphate, tetrafluoroborate or halide having an alkyl group with n=9 through 17 reacts with an equimolar amount of a primary hydroxy-amine (X=O), thiol-amine (X=S), or diamine (X=NH), yields a pyridinium salt 19 (m=2-6).

When X=O or NH, this compound 19 can be acylated or alkylated with an acylating or alkylating agent RCOHal or RHal, respectively, having a linear chain with 6-12 carbon atoms; alternatively, the reaction of 19 (X=O or NH) with a dicarboxylic acid derivative having k=1-6 affords a different type of "gemini" product 21.

When X=S, the pyridinium salt 22 has two supplementary possibilities of yielding a product with two hydrophobic residues, in addition to those mentioned for 19. (i) The facile oxidation of thiols to disulfides can afford either a "gemini" symmetrical disulfide 24. Treatment of 22 with another thiol in the presence of mild oxidants affords a non-symmetrical disulfide 23 (in addition to symmetrical disulfidic by-products).

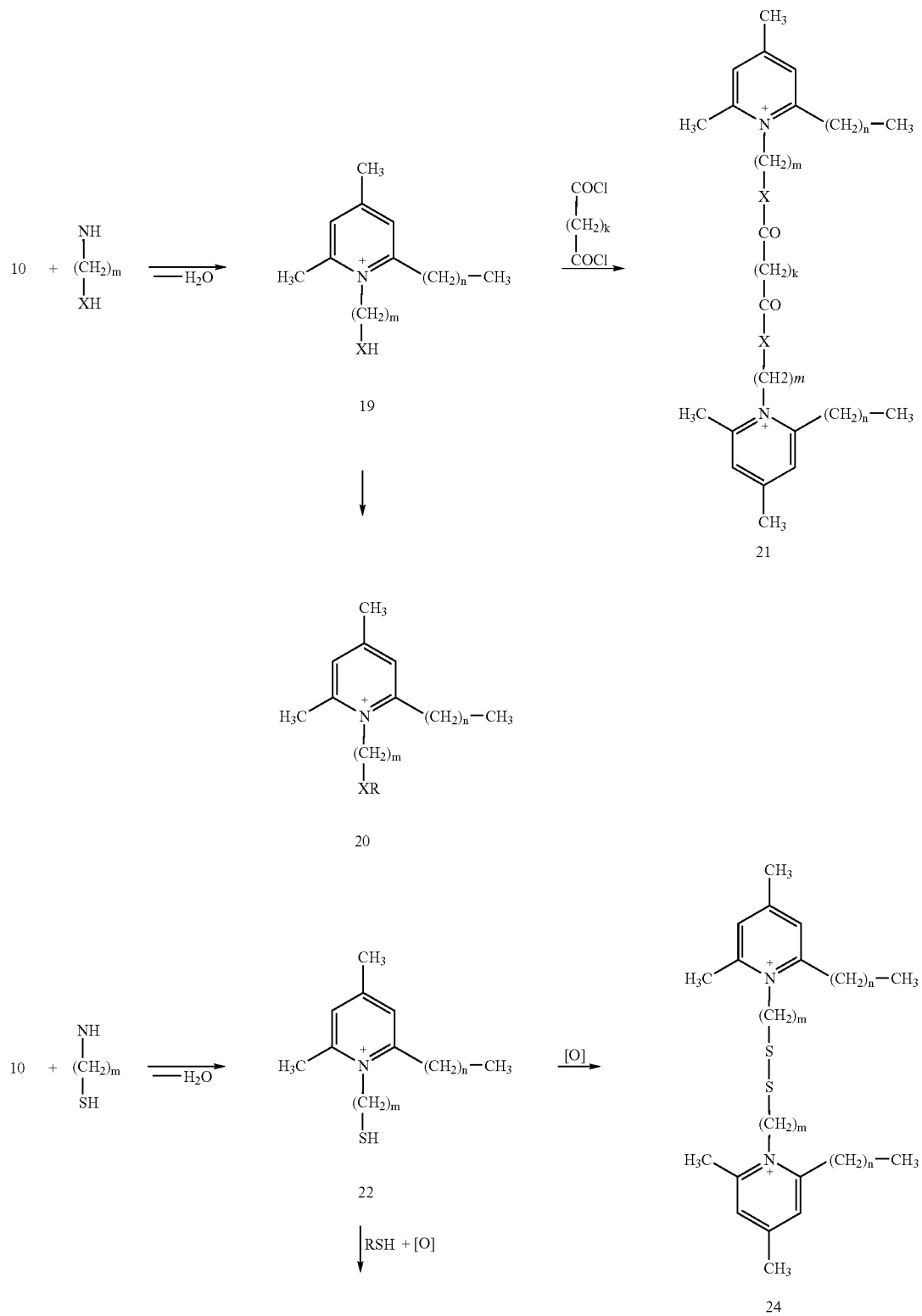

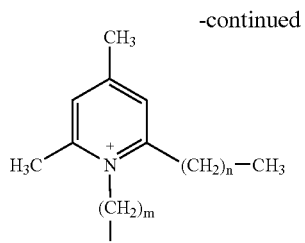

23

The following examples are included to demonstrate particular embodiments of the invention. Those of skill in the art should, in light of the present disclosure, appreciate that many changes can be made in the specific embodiments which are disclosed and still obtain a like or similar result without departing from the spirit and scope of the invention.

EXAMPLE 1

Synthesis of 1-(3,4-Bishexadecyloxyphenylethyl)-2,4,6-trimethyl)pyridinium hexafluorophosphate Step A. Synthesis of 1-(3,4-bishydroxyphenylethyl)-2,4,6-trimethyl)pyridinium hexafluorophosphate. (3, n=2).

3-Hydroxytyramine hydrochloride (2, n=2, 1.90 g, 10 mmol) of was suspended in 30 mL of anhydrous ethanol and treated with 2.68 g (10 mmol) of 2,4,6-trimethylpyrylium hexafluorophosphate (1) and 1.40 mL (10 mmol) of triethylamine. The dispersion was heated to reflux for 5 minutes, then 0.6 mL of acetic acid (10 mmol) was added and the reaction mixture was refluxed for another hour. Then, concentrated aqueous ammonia (0.5 mL) was added for converting any unreacted pyrylium salt into sym-collidine that is soluble in diethyl ether, and the reflux continued for another five minutes. After cooling, the mixture was poured into 200 mL anhydrous diethyl ether, the pale-cream colored solid was separated, washed with two portions (20 mL each) of diethyl ether, suspended in 5 mL of ethanol and filtered off. After drying, it was subsequently washed with water (2×10 mL) and recrystallized from methanol (25 mL) to give 2.52 g (yield 63%) of the title product (3, n=2).

Characterization: m.p. 218-220°. $^1$H-NMR (DMSO-d$_6$), δ, ppm: 8.89 (broad s, 2H: OH), 7.72 (s, 2H: Hβ-pyridinium), 6.67 (d, J=8.0 Hz, 1H: H-5, Ph), 6.60 (s, 1H: H-2, Ph), 6.47 (d, J=8.0 Hz, 1H: H-6, Ph), 4.54 (t, J=7.8 Hz, 2H: CH$_2$-Py$^+$), 2.95 (t, J=7.9 Hz, 2H: CH$_2$—Ph), 2.74 (s, 6H: CH$_3$ α-Py$^+$), 2.49 (s, 3H: CH$_3$ γ-Py$^+$); $^{13}$C-NMR (DMSO-d$_6$), δ, ppm: 157.8 (Cγ-pyridinium), 154.9 (2Cα-pyridinium), 146.0 (C-3, Ph), 145.1 (C-4, Ph), 128.8 (2Cβ-pyridinium), 127.8 (C-1, Ph), 120.2 (C-6, Ph), 117.0 (C-2, Ph), 116.5 (C-5, Ph), 53.7 (CH$_2$-Py$^+$), 33.4 (CH$_2$-Ph), 21.5 (CH$_3$ γ-pyridinium), 21.0 (2CH$_3$ α-pyridinium).

Step B. Acylation of 1-(3,4-bishydroxyphenylethyl)-2,4,6-trimethyl)pyridinium hexafluorophosphate with palmitoyl chloride (4, n=2, R=C$_{15}$H$_{31}$).

1-(3,4-Bishydroxyphenylethyl)-2,4,6-trimethylpyridinium hexafluorophosphate (1.21 g, 3 mmol) was suspended in 20 mL of anhydrous acetonitrile and treated under cooling with 1.83 mL (1.65 g, 6 mmol) of palmitoyl chloride and 0.84 mL (6 mmol) of triethylamine; after 5 minutes of stirring, the cooling bath was removed and the reaction mixture was heated to reflux for 3 h. After cooling, the solvent was evaporated in vacuum, and the residue was partitioned between 30 mL of chloroform and 20 mL of water. The aqueous layer was extracted with 30 mL of chloroform, and the combined chloroform layers were washed with 20 mL of water, separated, and dried on sodium sulfate. Evaporation to dryness yielded 2.4 g of crude compound that was purified by means of flash chromatography (silica gel 60, eluted with MeOH:CHCl$_3$ 20:80 v/v). The pure fractions were grouped, evaporated to dryness and the solid was recrystallized from acetonitrile to afford 1.2 g of pure compound, 4, n=2, R=C$_{15}$H$_{31}$ (yield 45%).

Characterization: m.p. 142.5° (determined by differential scanning calorimetry) $^1$H-NMR (CDCl$_3$), δ, ppm: 7.75 (s, 2H: Hβ-pyridinium), 7.15-7.25 (m, 3H: H2, H5, H-6, Ph), 4.65 (t, J=7.8 Hz, 2H: CH$_2$-Py$^+$), 3.16 (t, J=7.9 Hz, 2H: CH$_2$—Ph), 2.81 (s, 6H: CH$_3$ α-Py$^+$), 2.54 (s, 3H: CH$_3$ γ-Py$^+$), 2.18 (t, J=7.4 Hz, 4H: 2 CH$_2$CO), 1.62 (q, 4H: 2 CH$_2$CH$_2$CO), 1.08-1.20 (m, 24H: 12 CH$_2$ from fatty chains), 0.87 (t, J=6.7 Hz, 6H: 2CH$_3$ from fatty chains); $^{13}$C-NMR (CDCl$_3$), δ, ppm: 171.0 (2 C=O), 157.9 (Cγ-pyridinium), 155.1 (2Cα-pyridinium), 142.5 (C-3, Ph), 141.7 (C-4, Ph), 135.8 (C-1, Ph), 128.9 (2Cβ-pyridinium), 127.8 (C-6, Ph), 125.0 (C-2, Ph), 124.4 (C-5, Ph), 52.9 (CH$_2$-Py$^+$), 33.8 (CH$_2$—Ph), 32.9, 31.9, 29.9, 29.2, 25.0, 22.9 (all from fatty chains), 21.5 (CH$_3$ γ-pyridinium), 21.0 (2CH$_3$ α-pyridinium), 14.7 (2C: 2 CH$_3$ from fatty chains).

EXAMPLE 2

Synthesis of 1-(bis(hexadecyl)aminoethyl)-2,4,6-trimethylpyridinium hexafluorophosphate (9, m=15, n=2)

Step A. Synthesis of 1-(aminoethyl)-2,4,6-trimethylpyridinium hexafluorophosphate (8, n=2).

Ethylenediamine (6.0 g, 100 mmol) was dissolved in 30 mL of chloroform and treated under stirring with 2.68 g (10 mmol) of 2,4,6-trimethylpyrylium hexafluorophosphate. The solution was refluxed for 1 h, evaporated to ⅓ of the initial volume, cooled and poured into 100 mL of diethyl ether under stirring. The precipitated oily liquid was separated, washed with another two portions (20 mL each) of diethyl ether, and taken into 5 mL of hot ethanol. On cooling overnight the product crystallized and was filtered off, washed with cold ethanol and dried to yield 2.40 g of 8 (78%). TLC (MeOH: CHCl$_3$ 20:80 v/v) showed a high purity and it was used directly in the next step.

Step B. Alkylation of 1-(aminoethyl)-2,4,6-trimethylpyridinium hexafluorophosphate with hexadecyl bromide.

1-(Aminoethyl)-2,4,6-trimethylpyridinium hexafluorophosphate (8, n=2, 1.0 g, 3.2 mmol) was stirred with 4.9 g (16.0 mmol) hexadecyl bromide at 90° C. for 24 hours. The resulted brown solid was partitioned between 30 mL of chloroform and 20 mL of 10% aqueous sodium carbonate. The aqueous layer was extracted with 30 mL chloroform and the combined chloroform layers were washed with 20 mL of saturated aqueous sodium sulfate solution, separated, and dried on anhydrous sodium sulfate. Evaporation to dryness yielded 1.8 grams of crude compound (9, m=15, n=2) that was purified by means of flash chromatography (silica gel 60, eluted with MeOH:CHCl$_3$ 20:80 v/v). The pure fractions (monitored by TLC) were combined, evaporated to dryness, and the solid was recrystallized from acetonitrile to afford 0.4 g of pure compound (9, m=15, n=2). The yield was 16%.

Characterization: m.p. 64° (determined by differential scanning calorimetry) $^1$H-NMR (CDCl$_3$), δ, ppm: 7.45 (s, 2H: Hβ-pyridinium), 4.55 (t, J=5.4 Hz, 2H: CH$_2$-Py$^+$), 2.84 (s, 6H: CH$_3$ α-Py$^+$), 2.79 (t, J=5.8 Hz, 2H: CH$_2$—N(C16)$_2$), 2.54 (s, 3H: CH$_3$ γ-Py$^+$), 2.38 (t, J=6.6 Hz, 4H: 2 CH$_2$N), 1.10-1.43 (m, 28H: 14 CH$_2$ from fatty chains), 0.88 (t, J=6.5 Hz, 6H: 2CH$_3$ from fatty chains); $^{13}$C-NMR (CDCl$_3$), δ, ppm: 157.5 (Cγ-pyridinium), 154.8 (2Cα-pyridinium), 128.4 (2Cβ-pyridinium), 54.5 (CH$_2$-Py$^+$), 53.3 (CH$_2$CH$_2$-Py+), 51.8 (2CH$_2$—N from fatty chains), 31.9, 29.6, 29.3, 27.2, 26.9, 22.6 (all from fatty chains), 21.4 (2CH$_3$ α-pyridinium), 21.3 (CH$_3$ γ-pyridinium), 14.0 (2C: 2 CH$_3$ from fatty chains).

EXAMPLE 3

Synthesis of 2,4-dimethyl-1,6-ditetradecylpyridinium hexafluorophosphate (12, m=n=13)

Step A. Synthesis of 2,4-dimethyl-6-tetradecylpyrylium hexafluorophosphate (10, n=13).

n-Pentadecanoic acid (24.3 g, 0.1 mol) was refluxed with 45 mL of thionyl chloride for 90 minutes. The thionyl chloride in excess was evaporated under reduced pressure, 20 mL of hexane was added and then evaporated under reduced pressure to remove the traces of any remaining thionyl chloride. Anhydrous aluminum chloride (13.5 g, 0.1 mol) was added to the crude pentadecanoyl chloride under stirring and external cooling. The mixture became homogeneous in about 10 minutes. Then 12 mL (0.15 mmol) of mesityl oxide was added dropwise, and the reaction mixture was stirred at room temperature for 12 h. The resulting dark viscous mass was hydrolyzed by carefully adding 50 mL of ice-cold 5% hydrochloric acid and 50 mL of diethyl ether, with external cooling (ice bath). The ethereal layer was separated and extracted another time with 20 mL of diluted hydrochloric acid, then discarded. The combined aqueous solutions. were extracted with 20 mL of diethyl ether, separated and treated with 15 mL of hexafluorophosphoric acid, when the crude pyrylium hexafluorophosphate (10, n=13) separated as a brown oil. After extraction with chloroform, separation, drying on anhydrous sodium sulfate and evaporation of the solvent, 25.9 g of crude compound were obtained. It was recrystallized twice from ethanol to afford 11.2 g (yield 25%) of pure pyrylium hexafluorophosphate (10, n=13).

Characterization: m.p. 85° (determined by differential scanning calorimetry) $^1$H-NMR (CDCl$_3$), δ, ppm: 7.70 (s, 1H: H-3, pyrylium), 7.61 (s, 1H: H-5, pyrylium), 3.06 (t, J=7.9 Hz, 2H: Cα-CH$_2$), 2.86 (s, 3H: CH$_3$ γ-pyrylium), 2.69 (s, 3H: CH$_3$ α-pyrylium), 1.81 (q, J=7.6 Hz, 2H: Cα-CH$_2$CH$_2$), 1.40 (q, J=7.6 Hz, 2H: Cα-CH$_2$CH$_2$CH$_2$), 1.25 (m, 20H: 10 CH$_2$ from fatty chain), 0.87 (t, J=6.7 Hz, 3H: CH$_3$ from fatty chain); $^{13}$C-NMR (CDCl$_3$), δ, ppm: 180.9 (C-6, pyrylium), 177.7 (C-4, pyrylium), 174.7 (C-2, pyrylium), 123.8 (C-3, pyrylium), 122.5 (C-5, pyrylium), 34.7 (Cα-CH$_2$—), 31.8, 29.64, 29.62, 29.60, 29.57, 29.51, 29.32, 29.30, 29.0 (2C), 27.01 (all from fatty chain), 23.5 (CH$_3$ α-pyrylium), 22.6 (fatty chain), 21.1 (CH3 γ-pyrylium), 14.0 (CH$_3$ from fatty chain).

Step B. Conversion of 2,4-dimethyl-6-tetradecylpyrylium hexafluorophosphate by tetradecylamine into 2,4-dimethyl-1,6-bis(tetradecylpyridinium) hexafluorphosphate.

2,4-Dimethyl-6-tetradecylpyrylium hexafluorophosphate (10, n=13, 1.5 g, 3.33 mmol) was dissolved in 15 mL chloroform and treated with 0.71 g (3.33 mmol) of tetradecylamine (11, m=13). Triethylamine (0.5 mL) was then added to the brown-yellow solution, which was subsequently refluxed for 5 minutes, treated with 1 mL of acetic acid and refluxed for another hour. The homogenous mixture was treated with 0.2 mL of concentrated aqueous ammonia, refluxed for 5 min., cooled and extracted with 10 mL of water to solve the precipitated inorganic salts. After separation, the chloroform layer was dried on sodium sulfate and evaporated to dryness to yield 2.00 g of crude product. This product was purified by means of flash chromatography (Silica gel 60) using a 20/80 methanol/chloroform (v/v) mobile phase to yield 0.56 g (22%) of pure product, which was recrystallized from ethanol to yield 0.54 g of crystalline compound (12, m=n=13).

Characterization: m.p. 68.5° (determined by differential scanning calorimetry) $^1$H-NMR (CDCl$_3$), δ, ppm: 7.47 (s, 1H: H-3, pyridinium), 7.40 (s, 1H: H-5, pyridinium), 4.35 (t, J=8.4 Hz, 2H: N—CH$_2$), 2.93 (t, J=8.0 Hz, 2H: Cα-CH$_2$), 2.78 (s, 3H: CH$_3$ γ-pyridinium), 2.51 (s, 3H: CH$_3$ α-pyridinium), 1.75 (m, 4H: Cα-CH$_2$CH$_2$+N—CH$_2$CH$_2$), 1.43 (m, 4H: Cα-CH$_2$CH$_2$CH$_2$+N—CH$_2$CH$_2$CH$_2$), 1.16-1.40 (m, 40H: 20 CH$_2$ from fatty chain), 0.87 (t, J=6.7 Hz, 6H: 2CH$_3$ from fatty chains); $^{13}$C-NMR (CDCl$_3$), δ, ppm: 157.8 (C-4, pyridinium), 157.2 (C-6, pyridinium), 154.0 (C-2, pyridinium), 128.9 (C-3, pyridinium), 127.2 (C-5, pyridinium), 51.7 (N—CH$_2$), 33.0 (Cα-CH$_2$), 31.9, 29.64, 29.62, 29.57, 29.44, 29.42, 29.35, 29.32, 29.1, 28.9, 28.7, 28.6, 22.64 (all from fatty chains), 21.5 (CH3 γ-pyridinium), 20.9 (CH$_3$ α-pyridinium), 14.1 (2C: 2CH$_3$ from fatty chains).

Figure 9:
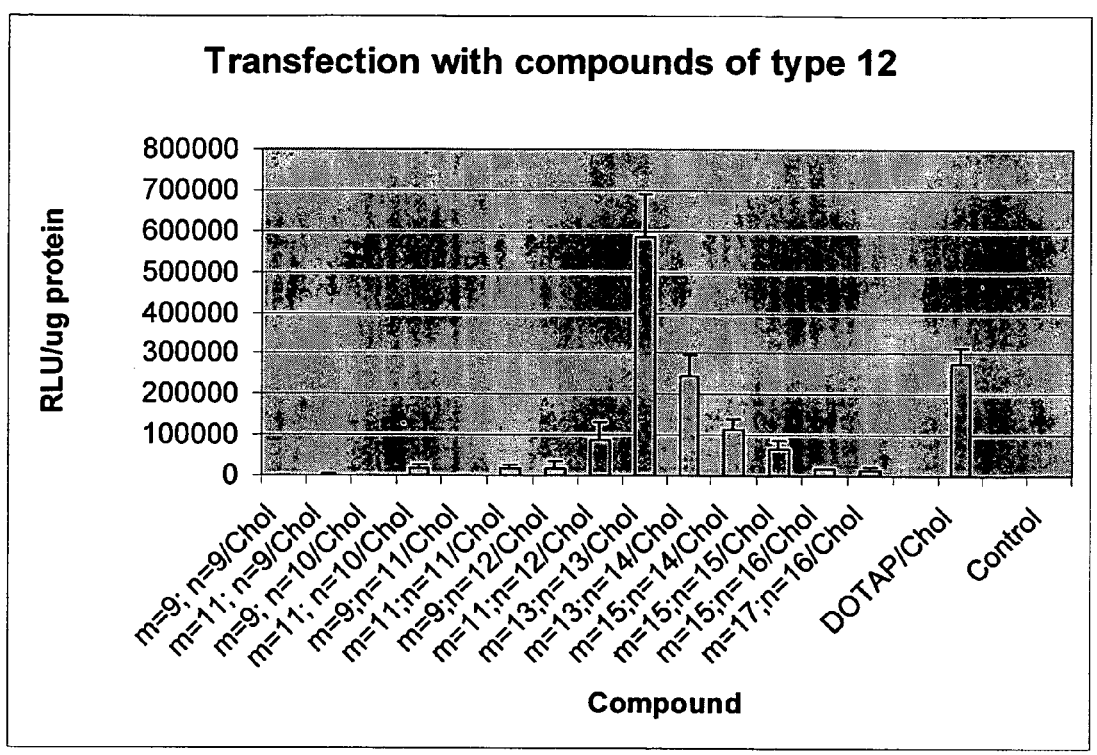
FIG. 9. Transfection data for dialkyl pyridinium lipids of type 12 (conditioned with cholesterol as co-lipid, at 1:1 molar ratio), on NCI-H23 tumor cell line.

For transfection efficiency see FIG. 9.

EXAMPLE 4

Synthesis of 1,6-bis(2,4-dimethyl-6-tetradecylpyridinium-1-yl)hexane di(hexafluorophosphate), (16, m=6, n=13)

2,4-Dimethyl-6-tetradecylpyrylium hexafluorophosphate (10, n=13, 1 g, 2.22 mmol) was dissolved in 10 mL of chloroform and treated with 0.09 g (0.75 mmol) of 1,6-hexanediamine. Triethylamine (0.2 mL) was then added to the brown-orange solution, which was subsequently refluxed for 5 minutes, treated with 0.5 mL of acetic acid and refluxed for another hour. The homogenous mixture was treated with 0.2 mL of concentrated aqueous ammonia, refluxed for 5 min., cooled and extracted with 10 mL of water to solve the precipitated inorganic salts. After separation, the chloroform layer was dried on sodium sulfate and evaporated to dryness to yield 0.95 g of crude product. This product was purified by means of flash chromatography (Silica gel 60) using a 20/80 mixture of methanol/chloroform (v/v) as mobile phase to afford 0.15 g (yield 20%) of purified product, which was recrystallized from ethanol yielding 0.14 g of crystalline compound (16, m=6, n=13).

Characterization: m.p. 189.9° (determined by differential scanning calorimetry) $^1$H-NMR (CDCl$_3$), δ, ppm: 7.42 (s, 2H: 2H3 pyridinium), 7.58 (s, 2H: 2H5 pyridinium), 4.42 (t, J=8.4 Hz, 4H: 2CH$_2$—N), 3.01 (t, J=7.9 Hz, 4H: 2CH$_2$—Cα), 2.82 (s, 6H, 2CH$_3$ γ-pyridinium), 2.53 (s, 6H, 2CH3 α-pyridinium), 1.88 (m, 4H, 2CH$_2$CH$_2$—N), 1.75 (quintuplet, J=7.3 Hz, 4H: 2CH$_2$CH$_2$—Cα), 1.64 (m, 4H: 2CH$_2$CH$_2$CH$_2$—N), 1.46 (quintuplet, J=7.4 Hz, 4H: 2CH$_2$CH$_2$CH$_2$—Cα), 1.21-1.40 (m, 20H: 10CH$_2$ from fatty chains), 0.89 (t, J=6.8 Hz, 6H: 2CH3 from fatty chains); $^{13}$C-NMR (CDCl$_3$), δ, ppm: 157.69 (2C6 pyridinium), 157.53 (2C2 pyridinium), 154.36 (2C4 pyridinium), 128.75 (2C3 pyridinium), 127.15 (2C5 pyridinium), 51.56 (2CH$_2$—N), 33.01 (2CH$_2$—Cα), 31.84, 29.62, 29.58, 29.34, 29.28, 29.21, 29.08, 28.83, 28.70, 25.39, 22.60 (all from fatty chains and N,N'-alkyl lariat), 21.53 (2CH$_3$ α-pyridinium), 21.03 (2CH$_3$ γ-pyridinium), 14.03 (2CH$_3$ from fatty chains).

Figure 10:
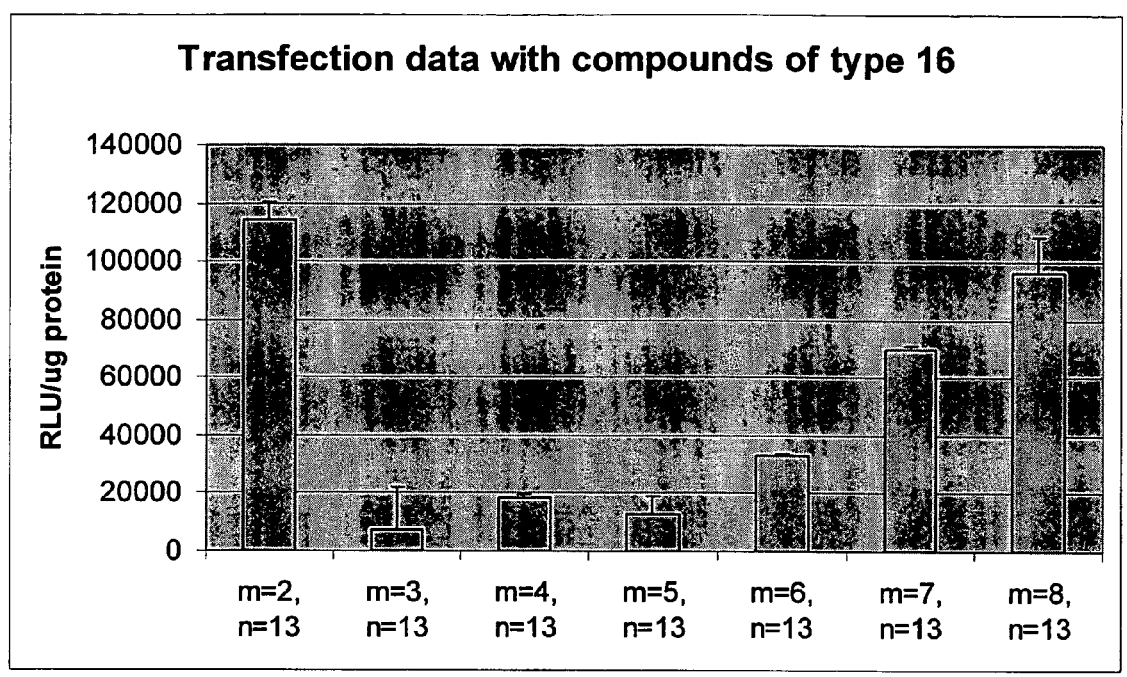
FIG. 10. Transfection data for dicationic lipids of type 16 (conditioned with cholesterol as co-lipid, at 1:1 molar ratio), on NCI-H23 tumor cell line.

For transfection efficiency see FIG. 10.

EXAMPLE 5

Synthesis of 1-(dodecanoyloxyethyl)-2,4-dimethyl-6-pentadecylpyridinium hexafluorophosphate. (20, m=2, n=14, X=O, R=CH$_3$(CH$_2$)$_{10}$CO)

Step A. Synthesis of 2,4-dimethyl-6-pentadecylpyridinium hexafluorophosphate. (10, n=14).

This compound was obtained after the same procedure used in the synthesis of 2,4-dimethyl-6-tetradecylpyrylium hexafluorophosphate 10 (n=13), described previously, starting directly from palmitoyl chloride (30.3 mL, 0.1 mol); yield: 13.9 g (30%).

Characterization: m.p. 80° (determined by differential scanning calorimetry) $^1$H-NMR (CDCl$_3$), δ, ppm: 7.70 (s, 1H: H-3, pyrylium), 7.62 (s, 1H: H-5, pyrylium), 3.06 (t, J=7.8 Hz, 2H: Cα-CH$_2$), 2.86 (s, 3H: CH$_3$ γ-pyrylium), 2.69 (s, 3H: CH$_3$ α-pyrylium), 1.79 (q, J=7.5 Hz, 2H: Cα-CH$_2$CH$_2$), 1.40 (m, 2H: Cα-CH$_2$CH$_2$CH$_2$), 1.25 (m, 24H: 12 CH$_2$ from fatty chain), 0.88 (t, J=6.7 Hz, 3H: CH$_3$ from fatty chain); $^{13}$C-NMR (CDCl$_3$), δ, ppm: 180.9 (C-6, pyrylium), 177.7 (C-4, pyrylium), 174.7 (C-2, pyrylium), 123.8 (C-3, pyrylium), 122.5 (C-5, pyrylium), 34.6 (Cα-CH$_2$—), 31.9, 29.62, 29.51, 29.30, 29.04, 27.0 (all from fatty chain), 23.4 (CH$_3$ α-pyrylium), 22.6 (fatty chain), 21.1 (CH$_3$ γ-pyrylium), 14.0 (CH$_3$ from fatty chain).

Step B. Conversion of 2,4-dimethyl-6-pentadecylpyridinium hexafluorophosphate into 1-(hydroxyethyl)-2,4-dimethyl-6-pentadecylpyridinium hexafluorophosphate. (19, m=2, n=14, X=O).

2-Aminoethanol (0.11 g, 1.8 mmol) was dissolved in 10 mL of chloroform and treated under stirring with 0.92 g (2 mmol) of 2,4-dimethyl-6-pentadecylpyridinium hexafluorophosphate. The solution was refluxed for 1 h, then the homogenous mixture was treated with 0.1 mL of concentrated aqueous ammonia and refluxed for 5 min. After cooling another 20 mL chloroform was added and the organic solution was extracted with Na$_2$SO$_4$ solution (10 mL), dryed on sodium sulfate and evaporated to dryness to yield 1.0 g of crude hydroxy derivative. This product was purified by means of flash chromatography (Silica gel 60) using a 20/80 mixture of methanol/chloroform (v/v) as mobile phase to afford 0.48 g (yield 53%) of purified product, which was used directly in the next step.

Step C. Acylation of 1-(hydroxyethyl)-2,4-dimethyl-6-pentadecylpyridinium hexafluorophosphate (19, m=2, n=14, X=O) with Lauroyl Chloride.

1-(Hydroxyethyl)-2,4-dimethyl-6-pentadecylpyridinium hexafluorophosphate (19, m=2, n=14, X=O, 0.48 g, 0.95 mmol) was dissolved in 10 mL anhydrous acetonitrile and treated, under stirring with 0.4 mL (1.7 mmol) lauroyl chloride and 0.15 mL triethylamine (1.1 mmol). The mixture was heated quickly to reflux and kept at 80° C. for 5 hours. After cooling, the solvent was evaporated in vacuum, and the residue was partitioned between 30 mL of chloroform and 20 mL of water. The aqueous layer was extracted with 30 mL of chloroform, and the combined chloroform layers were washed with 20 mL of water, separated, and dried on sodium sulfate. Evaporation to dryness yielded 1.0 g of crude compound that was purified by means of flash chromatography (silica gel 60, eluted with MeOH:CHCl$_3$ 20:80 v/v). The pure fractions were grouped, evaporated to dryness and the solid was recrystallized from acetonitrile to afford 0.35 g of pure compound, 20, m=2, n=14, X=O, R=CH$_3$(CH$_2$)$_{10}$CO) (yield 53%).

Characterization: m.p. 60.5° (determined by differential scanning calorimetry) $^1$H-NMR (CDCl$_3$), δ, ppm: 7.49 (s, 1H: H-3, pyridinium), 7.40 (s, 1H: H-5, pyridinium), 4.77 (t, J=5.5 Hz, 2H: O—CH$_2$), 4.46 (t, J=5.6 Hz, 2H: N—CH$_2$), 3.04 (t, J=7.9 Hz, 2H: CαPy+-CH$_2$), 2.85 (s, 3H: CH$_3$ γ-pyridinium), 2.54 (s, 3H: CH$_3$ α-pyridinium), 2.24 (t, J=7.5 Hz, 2H: CO—CH$_2$), 1.76 (q, J=7.2 Hz, 2H: Cα-CH$_2$CH$_2$), 1.48 (m, 4H: Cα-CH$_2$CH$_2$CH$_2$+COCH$_2$CH$_2$), 1.14-1.42 (m, 38H: 19 CH$_2$ from fatty chains), 0.88 (t, J=6.4 Hz, 6H: 2CH$_3$ from fatty chains); $^{13}$C-NMR (CDCl$_3$), δ, ppm: 173.0 (CO), 158.7 (C-4, pyridinium), 158.4 (C-2, pyridinium), 155.2 (C-6, pyridinium), 128.9 (C-5, pyridinium), 126.9 (C-3, pyridinium), 60.73 (O—CH$_2$), 49.7 (N—CH$_2$), 33.7 (COCH$_2$), 33.3 (Cα-CH$_2$), 31.9, 29.68, 29.57, 29.42, 29.30 29.32, 29.2, 29.0, 28.4, 24.6, 22.6 (all from fatty chains), 21.7 (CH$_3$ γ-pyridinium), 21.5 (CH$_3$ α-pyridinium), 14.1 (2C: 2CH$_3$ from fatty chains).

Figure 11:
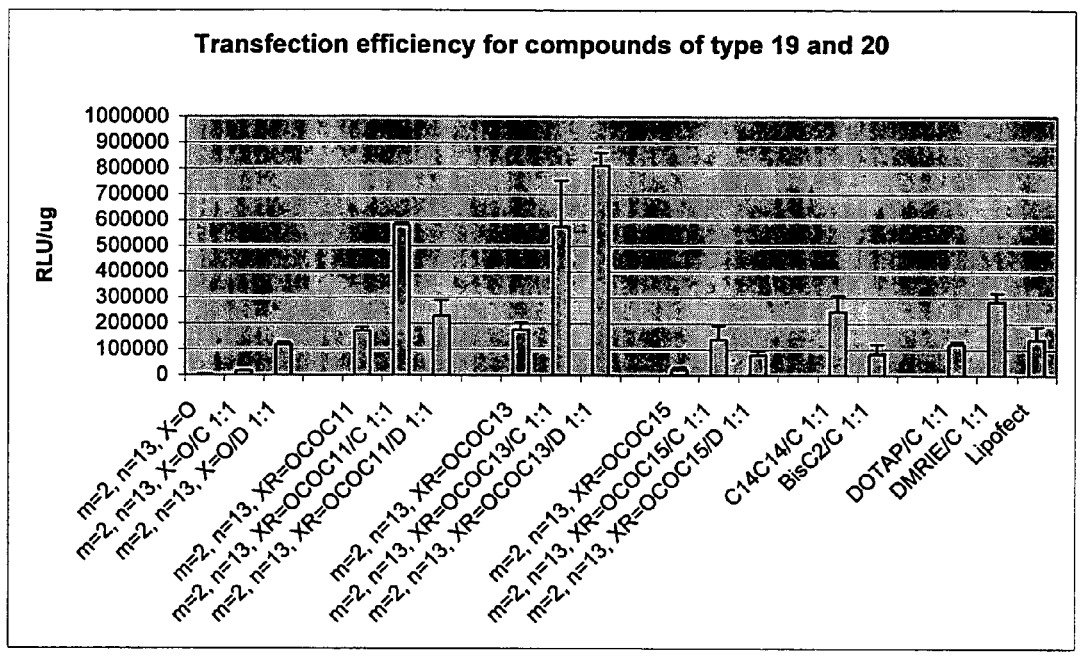
FIG. 11. Transfection data for pyridinium lipids of type 19 and 20 (alone, or conditioned with cholesterol or DOPE as co-lipid, at 1:1 molar ratio), on NCI-H23 tumor cell line.

For examples of transfection efficiency of compounds of type 20 see FIG. 11.

All of the compositions and methods disclosed and claimed herein can be made and executed without undue experimentation in light of the present disclosure. While the compositions and methods of this invention have been described in terms of particular embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

It should be apparent to one of skill in the art that the present disclosure describes pyridinium cationic lipids obtained from pyrylium salts and primary amines. The pyridinium cationic lipids of the present invention are suitable as transfection agents for gene therapy. Also disclosed is a method of synthesizing pyridinium cationic lipids by reacting a pyrylium salt with a primary amine.

It should be particularly apparent that contained herein is a procedure for synthesizing pyridinium cationic lipids (cytofectins) by treatment of a substituted pyrylium salt such as 2,4,6-trimethylpyrylium trifluoromethanesulfonate, hexafluorophosphate, tetrafluoroborate or halide (1) with a primary amine (2, n=0, 1, or 2) having two phenolic hydroxy groups; the resulting pyridinium salt (3) with two phenolic hydroxy groups is diacylated (R being a long-chain acyl group) or dialkylated (R=linear alkyl) yielding a cationic lipid 4.

Also contained herein is a procedure for synthesizing pyridinium cationic lipids (cytofectins) by treatment of a substituted pyrylium salt such as 2,4,6-trimethylpyrylium trifluoromethanesulfonate, hexafluorophosphate, tetrafluoroborate or halide (1) with a tertiary amine (5 or 8) having also a primary amino group. In the case of N,N-dihydroxyethyl-ethylenediamine (5, m=n=2) the resulting pyridinium salt is then diacylated (R being a long-chain acyl group) or dialkylated (R=linear alkyl) yielding a cationic lipid 7. When starting from equimolar amounts of 1 and ethylenediamine, the N-aminoethyl-2,4,6-trimethylpyridinium salt is then dialkylated to afford the cationic lipid 9 (which may alternatively be formed from 1 and 8). Compounds 9 with n=0 (hydrazine derivatives) are not protonated at physiological pH values, unlike compounds 7 or 9 with n≠0, which afford dications under these conditions.

Also contained herein is a procedure for synthesizing pyridinium cationic lipids (cytofectins) by treatment of a substituted pyrylium salt such as 2-alkyl-4,6-dimethylpyrylium hexafluorophosphate, trifluoromethanesulfonate, tetrafluoroborate or halide (10 with a long-chain alkyl group having n=9 through 17) with a primary alkylamine 11 (n=9 through 17) or para-substituted aniline 13 (n=7 through 15), yielding cationic lipids 12 or 14, respectively. Alternatively, the primary amine may be a para-substituted alkyl-benzylamine or alkyl-phenethylamine with a straight-chain alkyl group having 7 through 16 carbon atoms.

Also contained herein is a procedure for synthesizing pyridinium cationic lipids (cytofectins) by treating two moles of a substituted pyrylium salt such as 2-alkyl-4,6-dimethylpyrylium hexafluorophosphate, trifluoromethanesulfonate, tetrafluoroborate or halide (10 with a long-chain alkyl group having n=9 through 17) with one mole of a diamine (15, m=2 through 6, or 17, m=n=2; m=3, n=4) when cationic lipids 16 or 18, respectively, are formed. Analogously, the reaction of 10 may be performed with spermine or with triethylenetetramine.

Also contained herein is a procedure for synthesizing pyridinium cationic lipids (cytofectins) by reacting equimolar amounts of a substituted pyrylium salt such as 2-alkyl-4,6-dimethylpyrylium hexafluorophosphate, trifluoromethanesulfonate, tetrafluoroborate or halide (10 with a long-chain alkyl group having n=9 through 17) with a diamine, a hydroxy-amine, or a thiol-amine. The resulting pyridinium salt 19 (X=NH or O) may be diacylated or dialkylated with a linear-chain derivative affording 20, or treated with a half-molar equivalent of a diacid derivative to yield the gemini derivative 21. When the resulting pyridinium salt 22 has X=S, oxidation affords disulfides 23 or 24.

Also described herein are cytofectins (gene transfer agents) as 2,4,6-trisubstituted pyridinium salts having two hydrophobic chains that may be alkyl groups, esters or ethers attached to the nitrogen heteroatom via various linkers and prepared as indicated in claims 1 through 5 from a pyrylium salt and a primary amine.

Disclosed are pyridinium cationic lipids obtained from pyrylium salts and primary amines. The lipids comprise two long linear chains attached to a pyridinium ring via a variety of tether groups mediating this attachment. The pyridinium cationic lipids of the present invention are suitable as transfection agents for gene therapy. Also disclosed is a method of synthesizing pyridinium cationic lipids by reacting a pyrylium salt with a primary amine.

TABLE 1

Chemical Shifts (δ ppm) and Coupling Constants (J, Hz) in $^{1}$H-NMR Spectra (300 MHz) in different solvent of 1-(2,3-dihydroxipropyl)-2,4,6-trimethylpyridinium perchlorate (19Aa) - assignments are given by means of signal integration, selective decoupling and HETCOR ($^{1}$H-$^{13}$C)

| Solvent | Temperature | H-β | HO-2 | HO-3 | H-1 | H-1 | H-2 | H-3 | H-3 | CH$_3$-α | CH$_3$-γ |
|---|---|---|---|---|---|---|---|---|---|---|---|
| DMSO-d$_6$ | 20° C. | 7.73 s | 5.42 d [5.0] | 5.09 t [5.6] | 4.56 dd [3.6, 14.9] | 4.48 dd [9.5, 14.9] | 3.92 m | 3.56 m [4.6, 5.1, 11.1] | 3.46 m [5.2, 6.7, 11.1] | 2.81 s | 2.49 s |
| DMSO-d$_6$ | 60° C. | 7.70 s | 5.30 bs | 4.90 bs | 4.56 dd [3.6, 14.9] | 4.49 dd [9.3, 14.9] | 3.92 m | 3.57 dd [4.6, 11.1] | 3.48 dd [6.6, 11.1] | 2.81 s | 2.49 s |
| DMSO-d$_6$ + TFA | 20° C. | 7.22 s | — | — | 4.62 dd [3.4, 14.8] | 4.53 dd [9.5, 14.8] | 3.98 m | 3.62 dd [4.6, 11.1] | 3.53 dd [6.6, 11.1] | 2.85 s | 2.51 s |
| DMSO-d$_6$ + TFA | 45° C. | 7.70 s | — | — | 4.62 dd [3.6, 14.8] | 4.54 dd [9.5, 14.8] | 3.98 m | 3.63 dd [4.6, 11.1] | 3.54 dd [6.5, 11.1] | 2.85 s | 2.51 s |
| DMSO-d$_6$ + TFA | 70° C. | 7.68 s | — | — | 4.63 dd [3.6, 14.8] | 4.54 dd [9.3, 14.8] | 3.99 dddd [3.6, 4.6, 6.5, 9.3] | 3.63 dd [4.6, 11.1] | 3.54 dd [6.5, 11.1] | 2.84 s | 2.51 s |
| DMSO-d$_6$ + TFA | 90° C. | 7.66 s | — | — | 4.63 dd [3.8, 15.0] | 4.54 dd [9.1, 15.0] | 3.99 m | 3.64 dd [4.7, 11.2] | 3.55 dd [6.4, 11.2] | 2.84 s | 2.51 s |
| CD$_3$NO$_2$ | 20° C. | 7.60 s | 3.57 d [4.9] | 3.16 t [5.5] | 4.72 dd [9.9, 15.0] | 4.61 dd [3.3, 15.0] | 4.24 dqd* [3.3, 5.1, 9.9*] | 3.79 dt [11.5, 4.7] | 3.73 dt [11.5, 5.1] | 2.88 s | 2.56 s |
| C$_5$D$_5$N | 20° C. | 7.39 s | — | — | 4.98 m [9.1, 14.7] | 4.98 m [9.1, 14.7] | 4.60 m | 4.19 dd [4.6, 11.1] | 4.12 dd [6.3, 11.1] | 2.96 s | 2.27 s |
| D$_2$O | 20° C. | 7.42 s | — | — | 4.48 dd [9.5, 15.1] | 4.40 dd [3.9, 15.1] | 4.03 m | 3.64 dd [4.8, 11.8] | 3.58 dd [5.3, 11.8] | 2.64 s | 2.34 s |
| DMFA - d$_7$ | 20° C. | 7.82 s | 5.67 d [4.9] | 5.18 t [5.7] | 4.80 dd [3.8, 15.0] | 4.72 dd [9.3, 14.7] | 4.19 m [4.6] | 3.76 dt [4.7, 11.5] | 3.66 dt [6.5, 11.0] | 2.95 s | 2.56 s |

*dqd represents the multiplicity of a doublet of quartets of doublets; the small doublet of 3.3 Hz is the coupling with one of H-1, the quartet comes from almost equal couplings of H-2 with OH 4.9 Hz and with two H-3 of 4.7 and 5.1 Hz respectively, while the big doublet of 9.9 Hz is the coupling with the other H-1.

TABLE 2

Chemical Shifts (δ ppm) in $^{13}$C-NMR Spectra (75 MHz) in different solvent of 1-(2,3-dihydroxipropyl)-2,4,6-trimethylpyridinium perchlorate (19Aa) - assignments are given by means of signal integration, APT and HETCOR ($^1$H-$^{13}$C)

| Solvent | Temperature | C-γ | C-α | C-β | C-2 | C-3 | C-1 | CH$_3$-α | CH$_3$-γ |
|---|---|---|---|---|---|---|---|---|---|
| DMSO-d$_6$ | 20° C. | 157.05 | 155.20 (broad) | 127.94 t: 128.00 127.95 127.90 | 69.79 | 63.62 | 54.74 | 21.20 (broad) | 20.81 |
| DMSO-d$_6$ | 60° C. | 156.79 | 154.97 (broad) | 127.71 t: 127.75 127.71 127.67 | 69.55 | 63.36 | 54.59 | 20.89 (sharp) | 20.48 |
| DMSO-d$_6$ + TFA | 20° C. | 157.70 | 155.83 (broad) | 128.53 t: 128.58 128.53 128.48 | 70.47 | 64.18 | 55.38 | 21.68 (broad) | 21.11 |
| DMSO-d$_6$ + TFA | 45° C. | 157.54 | 155.69 (sharp) | 128.38 (broad)* | 70.35 | 64.07 | 55.30 | 21.47 (sharp) | 20.91 |
| DMSO-d$_6$ + TFA | 70° C. | 157.40 | 155.56 | 128.23 (sharp) | 70.24 | 63.69 | 55.21 | 21.28 | 20.79 |
| CD$_3$NO$_2$ | 20° C. | 159.92 | 156.90 (broad) | 129.70 | 71.64 | 65.17 | 55.37 | 22.19 | 21.62 |
| C$_5$D$_5$N | 20° C. | 157.67 | 155.46 (broad) | 128.52 | 71.21 | 64.79 | 55.56 | 21.58 (broad) | 20.91 |
| D$_2$O | 20° C. | 161.01 | 157.52 (broad) | 130.89 (broad) | 72.13 | 65.49 | 56.33 | 23.49 (broad) | 23.08 |
| DMFA-d$_7$ | 20° C. | 158.26 | 156.32 (broad) | 128.82 (broad) | 71.10 | 64.79 | 55.70 | 21.61 (broad) | 21.11 |

*At the temperature of 318 K (45° C.) coalescence occurred for the three separate signals of C-β.

TABLE 3

Chemical Shifts (δ ppm) and Coupling Constants (J, Hz) in $^1$H-NMR Spectra (300 MHz) of compounds of type 19, 20, 23, and 24. Assignments are given by means of signal integration, selective decoupling and HETCOR ($^1$H-$^3$C)

| Nr. | Comp. | Solvent | Hβ (Hβ$_A$) | (Hβ$_B$) | Ph | OH (2-OH) | (3-OH) | CH$_2$ (1) H$_A$ | H$_B$ |
|---|---|---|---|---|---|---|---|---|---|
| 1 | 19Aa | DMSO-d$_6$ | 7.73 s | | — | 5.42 d [5.0] | 5.09 t [5.6] | 4.56 dd [3.6; 14.9] | 4.48 dd [9.5; 14.9] |
| 2 | 20Aa | CDCl$_3$ | 7.54 s | | — | — | — | 4.89 dd [9.7; 15.7] | 4.82 dd [4.7; 15.7] |
| 3 | 19Ab | DMSO-d$_6$ | 7.70 s | | — | not seen | | 4.55 dd [3.6; 14.9] | 4.48 dd [9.5; 14.9] |
| 4 | 20Ab | CDCl$_3$ | 7.49 s | | — | — | — | 4.87 dd [9.7; 15.8] | 4.80 dd [4.8; 15.8] |
| 5 | 19Ba | DMSO-d$_6$ | 8.39 s | | 8.32 d [6.6]; 7.84-7.90 m; 7.60-7.70 m | not seen | | 4.76 dd [3.8; 14.1] | 4.43 dd [9.8; 14.1] |
| 6 | 20Ba | CDCl$_3$ | 7.92 s | | 7.49-7.85 m | — | — | 5.08 dd [3.1; 14.4] | 5.01 dd [8.8; 14.5] |
| 7 | 19Bb | DMSO-d$_6$ | 8.39 s | | 8.23 d [6.5]; 7.87 m; 7.66 m | not seen | | 4.77 dd [3.7; 14.1] | 4.43 dd [9.8; 14.1] |
| 8 | 20Bb | CDCl$_3$ | 7.91 s | | 7.81 d [6.4]; 7.52-7.69 m | — | — | 5.21 dd [2.7; 15.1] | 5.03 dd [9.9; 15.1] |
| 9 | 23Aa | DMSO-d$_6$ | 7.75 d [2.0] | 7.71 d [2.0] | — | 5.36 bs | | 4.01 dd [8.4; 12.2] | |
| 10 | 24Aa | CDCl$_3$ | 7.62 s | | — | — | | 4.80 dd [7.9; 12.3] | |
| 11 | 23Ab | DMSO-d$_6$ | 7.76 d [2.0] | 7.72 d [2.0] | — | 5.62 bs | | 3.99 dd [8.5; 12.2] | 3.90 dd [5.6; 12.2] |
| | | DMSO-d$_6$ + TFA | 7.68 d [1.8] | 7.65 d [1.8] | — | | | 3.99 dd [8.4; 12.2] | 3.90 dd [5.6; 12.2] |
| 12 | 24Ab | CDCl$_3$ | 7.63 d [2.2] | 7.62 d [2.2] | — | — | | 4.80 dd [8.0; 12.4] | |
| 13 | 23Ba | DMSO-d$_6$ | 8.39 bs | | 8.24 d [6.8]; 7.55-7.83 m | 5.36 t [5.2] | | 3.60 dd [5.0; 8.0] | 3.56 dd [5.0; 8.0] |
| | | DMSO-d$_6$ (75° C.) | 8.31 s | | 8.18 d [6.7]; 7.55-7.83 m | 5.19 bs | | 3.56 dd [8.2; 11.6] | |
| 14 | 24Ba | CDCl$_3$ | 7.79-7.86 bs | | 7.38-7.78 m | — | | 4.38 dd [7.3; 12.2] | |
| 15 | 23Bb | DMSO-d$_6$ | 8.38 bs | | 8.24 d[6.9]; 7.55-7.85 m | 5.48 t [5.2] | | 3.58 dd [5.1; 8.0] | 3.54 dd [5.1; 8.0] |
| | | DMSO-d$_6$+ TFA | 8.39 bs | | 8.24 d [6.8]; 7.55-7.86 m | not seen | | 3.60 dd [8.4; 11.6] | |
| 16 | 24Bb | CDCl$_3$ | | | 7.47-8.03 m | — | | 4.78 dd [6.9; 12.3] | |

TABLE 3-continued

Chemical Shifts (δ ppm) and Coupling Constants (J, Hz) in ¹H-NMR Spectra (300 MHz) of compounds of type 19, 20, 23, and 24. Assignments are given by means of signal integration, selective decoupling and HETCOR (¹H-³C)

| | | | CH$_2$ (3) | | CH$_3$ (Py+) | | | CH$_3$CO (acetates) | |
|---|---|---|---|---|---|---|---|---|---|
| Nr. | CH | H$_A$ | | H$_B$ | α | (α') | γ | (2-) | (3-) |
| 1 | 3.92 m [4.6; 6.5; 9.3] | 3.56 m [5.1; 4.6; 11.1] | | 3.46 m [5.2; 6.7; 11.1] | 2.81 s | | 2.49 s | — | — |
| 2 | 5.49 m [4.7] | 4.46 dd [4.0; 11.2] | | 4.29 dd [4.6; 11.2] | 2.88 s | | 2.54 s | 2.13 s | 1.93 s |
| 3 | 3.92 m | 3.57 dd [4.6; 11.0] | | 3.48 dd [6.7; 11.0] | 2.80 s | | 2.49 s | — | — |
| 4 | 5.48 m [4.1; 4.8] | 4.45 dd [4.1; 12.3] | | 4.27 dd [4.9; 12.3] | 2.86 s | | 2.53 t [0.7] | 2.12 s | 1.92 s |
| 5 | 3.28 m | 2.94 dd [5.0; 11.1] | | 2.80 dd [6.3; 11.1] | — | | — | — | — |
| 6 | 4.93 m | 3.74 dd [4.6; 12.1] | | 3.46 dd [4.1; 12.1] | — | | — | 1.92 s | 1.76 s |
| 7 | 3.28 m | 2.94 dd [4.9; 11.1] | | 2.80 dd [6.2; 11.1] | — | | — | — | — |
| 8 | 4.90 m | 3.75 dd [4.7; 12.1] | | 3.48 dd [4.5; 12.1] | — | | — | 1.91 s | 1.76 s |
| 9 | 5.27 m | | 3.92 dd [5.6; 12.3] | | 2.84 s | 2.81 s | 2.48 s | — | |
| 10 | 5.61 m | | 4.65 dd [5.6; 12.3] | | 2.94 s | 2.90 s | 2.58 s | 2.02 s | |
| 11 | 5.31 m | 3.07 dd [4.8; 14.6] | | 3.02 dd [4.8; 14.6] | 2.91 s | 2.82 s | 2.46 s | — | |
| | 5.29 m [2.7; 7.0] | 3.05 dd [4.9; 14.5] | | 3.02 dd [4.7; 14.5] | 2.85 s | 2.79 s | 2.43 s | — | |
| 12 | 5.61 m [0.7; 6.6] | | 4.63 dd [5.5; 12.4] | | 2.92 s | 2.88 s | 2.57 s | 2.00 s | |
| 13 | 5.08 m [6.9] | 3.35 dd [5.4; 11.5] | | 3.31 dd [5.5; 11.5] | — | | — | — | — |
| | 5.14 m | | 3.36 dd [6.5; 11.6] | | — | | — | — | — |
| 14 | 5.35 m [6.9] | | 4.00 dd [6.4; 12.2] | | — | | — | 1.97 s | |
| 15 | 5.27 m [6.9] | | 3.31 m | | — | | — | — | — |
| | 5.15 m | | 3.36 dd [6.2; 11.6] | | — | | — | — | — |
| 16 | 5.34 m [6.7] | | 4.04 dd [6.5; 12.2] | | — | | — | 1.94 s | |

TABLE 4

Chemical Shifts (δ ppm) in ¹³C-NMR Spectra (75 MHz), in different, solvents of compounds of type 19, 20, 23, and 24; assignments by signal integration, APT and HETCOR (¹H-¹³C)

| | | | C=O (Acetates) | | | Cα(Py+) | | Ph - Substituents of Py+ | | | | |
|---|---|---|---|---|---|---|---|---|---|---|---|---|
| Nr. | Comp. | Solvent | C=O (2) | C=O (3) | Cγ(Py+) | (Cα) | (Cα') | CqPhγ | CqPhα | CγPhγ | CβPhγ | CαPhγ |
| 1 | 19Aa | DMSO-d$_6$ | — | — | 157.05 | 155.20 broad | | — | — | — | — | — |
| 2 | 20Aa | CDCl$_3$ | 170.28 | 169.48 | 158.96 | 155.31 | | — | — | — | — | — |
| 3 | 19Ab | DMSO-d$_6$ | — | — | 155.46 | 157.54 | | — | — | — | — | — |
| 4 | 20Ab | CDCl$_3$ | 170.35 | 169.54 | 158.83 | 155.52 | | — | — | — | — | — |
| 5 | 19Ba | DMSO-d$_6$ | — | — | 157.49 | 154.53 | | 133.44 | 133.81 | 132.77 | 131.19 | 128.91 |
| 6 | 20Ba | CDCl$_3$ | 169.67 | 169.65 | 157.50 | 156.55 | | 133.47 | 132.59 | 132.51 | 131.36 | 129.57 broad |
| 7 | 19Bb | DMSO-d$_6$ | — | — | 157.40 | 154.52 | | 133.44 | 133.82 | 132.76 | 131.18 | 128.91 |
| 8 | 20Bb | CDCl$_3$ | | 169.61 | 157.58 | 156.10 | | 133.32 | 132.63 | 132.47 | 131.22 | 129.43 |
| 9 | 23Aa | DMSO-d$_6$ | | — | 157.38 | 156.72 | 155.26 | — | — | — | — | — |
| 10 | 24Aa | CDCl$_3$ | | 170.32 | 159.64 | 156.18 | 154.78 | — | — | — | — | — |
| 11 | 23Ab | DMSO-d$_6$ | | — | 157.07 | 156.79 | 155.11 | — | — | — | — | — |

TABLE 4-continued

Chemical Shifts (δ ppm) in $^{13}$C-NMR Spectra (75 MHz), in different, solvents of compounds of type 19, 20, 23, and 24; assignments by signal integration, APT and HETCOR ($^1$H-$^{13}$C)

| Nr. | | Solvent | | | | | | | | |
|---|---|---|---|---|---|---|---|---|---|---|
| 12 | 24Ab | CDCl$_3$ | 170.32 | 159.65 | 156.22 | 154.84 | — | — | — | — |
| 13 | 23Ba | DMSO-d$_6$ | — | ?* | 153.45 | 132.79 | 133.76 broad | 132.44 | 130.78 | 138.76 |
| | | DMSO-d$_6$ (75° C.) | — | 157.57 | 153.29 | 132.54 | 133.41 | 131.98 | 130.37 | 128.29 |
| 14 | 24Ba | CDCl$_3$ | 169.64 | ? | 156.51 | 133.53 | 132.74 broad | 132.32 | 131.45 | 129.10 broad |
| 15 | 23Bb | DMSO-d$_6$ | — | ? | 153.33 | 133.79 | 132.81 | 132.40 | 130.73 | 128.76 |
| 16 | 24Bb | CDCl$_3$ | 169.42 | 157.85 | 155.35 | 133.46 | 132.71 | 132.45 | 131.32 | 128.16 |

| | Ph - Substituents of Py+ | | | Cβ(Py+) | | CH | CH$_2$ | | Me-substituents of Py+ | | | CH$_3$CO (acetates) | |
|---|---|---|---|---|---|---|---|---|---|---|---|---|---|
| Nr. | CγPhα | CβPhα | CαPhα | Cβ | Cβ' | (C2) | 3-CH$_2$ | 1-CH$_2$ | CH$_3$α | CH$_3$α' | CH$_3$γ | (2-Ac) | (3-A) |
| 1 | — | — | — | 127.95 | | 69.72 | 63.49 | 54.71 | 21.20 | 20.80 | | — | — |
| 2 | — | — | — | 128.74 | | 68.37 | 62.44 | 51.50 | 21.46 | 21.51 | | 20.56 | 20.3 |
| 3 | — | — | — | 128.26 | | 69.01 | 63.70 | 54.88 | 21.46 | 21.10 | | — | — |
| 4 | — | — | — | 128.62 | | 68.55 | 62.49 | 51.58 | 21.40 | 21.53 | | 20.55 | 20.3 |
| 5 | 129.80 | 129.32 | 130.02 | 126.08 | | 68.84 | 63.61 | 58.24 | — | — | | — | — |
| 6 | 129.57 broad | 128.17 | 129.78 | 126.58 | | 69.09 | 61.67 | 54.33 | — | — | | 20.73 | 20.2 |
| 7 | 129.88 broad | 129.32 | 130.01 | 126.96 | | 68.83 | 63.60 | 58.26 | — | — | | — | — |
| 8 | 129.72 | 128.03 | 129.72 | 126.23 | | 69.11 | 61.62 | 54.55 | — | — | | 20.62 | 20.2 |
| 9 | — | — | — | 130.05 | 128.36 | 70.57 | 59.28 | | 23.05 | 21.70 | 20.62 | — | |
| 10 | — | — | — | 131.12 | 129.46 | 63.51 | 61.75 | | 23.07 | 22.18 | 21.48 | 20.42 | |
| 11 | — | — | — | 129.83 | 128.16 | 70.43 | 58.98 | | 23.09 | 21.67 | 20.57 | — | |
| 12 | — | — | — | 130.99 | 129.35 | 63.50 | 61.62 | | 22.84 | 21.93 | 21.32 | 20.30 | |
| 13 | 129.55 | 128.52 broad | 129.84 | ? | | 73.27 | 60.26 | | — | — | | — | |
| | 129.14 | 128.08 | 129.47 | 126.57 | | 73.01 | 60.04 | | — | — | | — | |
| 14 | 129.61 broad | 128.52 | 129.53 | ? | | 65.84 | 62.67 | | — | — | | 20.42 | |
| 15 | 129.54 | 128.46 (split in 3 signals: 128.60, 128.46, 128.25) | 129.91 | 126.86 broad | | 73.41 | 60.19 | | — | — | | — | |
| 16 | 129.70 | 128.88 broad | 129.51 | 128.88 | | 66.30 | 62.58 | | — | — | | 20.29 | |

*"?" signifies that the signal is so broad it disappeared in the baseline noise.

TABLE 5

Chemical Shifts (δ, ppm) and Coupling Constants (J, Hz) in $^1$H-NMR Spectra (300 MHz) of pyridinio lipids of type 21 and 25 (in CDCl$_3$). Assignments are given by means of signal intensity, selective decoupling and HETCOR ($^1$H-$^{13}$C).

| | Hβ | | CH$_2$(1) | | | CH$_2$(3) | | CH$_3$(Py+) | | |
|---|---|---|---|---|---|---|---|---|---|---|
| Comp | (Hβ$_A$) | (Hβ$_B$) | H$_A$ | H$_B$ | CH | H$_A$ | H$_B$ | α | α' | γ |
| 21AaP | 7.45 s | | 4.87 d [7.3] | 5.52 m [4.0; 5.2;] | | 4.49 dd [4.0; 12.3] | 4.24 dd [5.2; 12.3] | 2.88 s | 2.52 s | |
| 21AaS | 7.46 s | | 4.89 d [7.5] | 5.52 m [5.2; 12.3] | | 4.50 dd [4.0; 12.4] | 4.25 dd [5.2; 12.3] | 2.89 s | 2.52 s | |
| 21AaO | 7.45 s | | 4.88 d [7.4] | 5.52 m [4.2; 5.4] | | 4.49 dd [4.0; 12.3] | 4.25 dd [5.2; 12.3] | 2.88 s | 2.53 s | |
| 25AaP | 7.62 d [2.1] | 7.58 d [2.1] | 4.83 dd [7.6; 12.4] | 5.58 m [6.6] | | 4.65 dd [5.8; 12.4] | | 2.95 s | 2.88 s | 2.58 s |
| 25AaS | 7.62 brs | 7.59 brs | 4.85 dd [7.6; 12.3] | 5.55 m | | 4.66 dd [5.7; 12.3] | | 2.97 s | 2.90 s | 2.58 s |
| 25AaO | 7.59 d [2.2] | 7.55 d [2.2] | 4.85 dd [7.4; 12.3] | 5.55 m [6.7] | | 4.66 dd [6.0; 12.3] | | 2.95 s | 2.89 s | 2.58 s |
| 21AbP | 7.44 s | | 4.83 dd [7.4] | 5.51 m [3.9; 5.2] | | 4.48 dd [3.9; 12.2] | 4.24 dd [5.3; 12.2] | 2.86 s | 2.51 s | |
| 21AbS | 7.45 s | | 4.87 m [2.6; 12.4] | 5.52 m | | 4.48 dd [3.9; 12.2] | 4.23 dd [5.0; 12.2] | 2.88 s | 2.53 s | |

TABLE 5-continued

Chemical Shifts (δ, ppm) and Coupling Constants (J, Hz) in ¹H-NMR Spectra (300 MHz) of pyridinio lipids of type 21 and 25 (in CDCl₃). Assignments are given by means of signal intensity, selective decoupling and HETCOR (¹H-¹³C).

| | | | | | | | | |
|---|---|---|---|---|---|---|---|---|
| 21AbO | | 7.38 s | 4.88-4.94 m | 5.51 m [4.6; 5.0] | 4.48 dd [4.2; 12.4] | 4.23 dd [5.4; 12.3] | 2.89 s | 2.52 s |
| 25AbP | 7.60 d [1.9] | 7.56 d [1.9] | 4.82 dd [7.5; 12.4] | 5.54 m [5.8; 7.5] | | 4.64 dd [5.8; 12.4] | 2.93 s | 2.86 s | 2.57 s |
| 25AbS | 7.66 s | 7.63 s | 4.97 dd [7.4; 12.3] | 5.61 m [5.6; 6.6] | | 4.75 dd [5.8; 12.3] | 3.04 s | 2.95 s | 2.59 s |
| 25AbO | 7.70 s | 7.67 s | 4.95 dd [7.6; 12.4] | 5.61 m | | 4.73 dd [5.8; 12.4] | 3.04 s | 2.94 s | 2.60 s |

FATTY chain

| Comp | 3-COCH₂ Hₐ | 3-COCH₂ Hᵦ | CO—CH₂ COCH₂ | CO—CH₂—CH₂ 3- CH₂ | CO—CH₂—CH₂ 2- CH₂ | CH=CH | (CH₂)n | CH₃ |
|---|---|---|---|---|---|---|---|---|
| 21AaP | 2.22 dt [7.4; 7.4; 16.1] | 2.08 dt [7.4; 7.4; 16.1] | 2.36 t [7.5] | 1.41 qnt [7.4] | 1.62 qnt [7.4] | — | 1.10-1.38 m | 0.88 [6.7] |
| 21AaS | 2.22 dt [7.5; 7.5; 16.0] | 2.08 dt [7.4; 7.4; 16.1] | 2.36 t [7.5] | 1.41 qnt [7.5] | 1.62 qnt [7.5] | — | 1.00-1.36 m | 0.88 [6.3] |
| 21AaO | 2.22 dt | 2.08 dt | 2.36 t [7.5] | 1.41 qnt [7.4] | 1.62 m | 5.26-5.41 m | 1.03-1.38 m | 0.88 [6.7] |
| 25AaP | | 2.27 t [7.5] | | 1.50 qnt [7.0] | | — | 1.00-1.40 m | 0.88 [6.7] |
| 25AaS | | 2.27 t [7.5] | | 1.50 qnt | | — | 1.00-1.40 m | 0.88 [6.7] |
| 25AaO | | 2.27 t [7.5] | | 1.50 m | | 5.27-5.44 m | 1.20-1.40 m | 0.88 [6.7] |
| 21AbP | 2.21 dt [7.4; 7.4 16.1] | 2.07 dt [7.4; 7.4; 16.1] | 2.35 t [7.5] | 1.40 qnt [7.2] | 1.62 qnt [7.2] | — | 1.08-1.34 m | 0.88 [6.8] |
| 21AbS | 2.21 dt [7.4; 7.4; 16.1] | 2.07 dt [7.4; 7.4; 16.1] | 2.37 t [7.4] | 1.40 qnt [7.2] | 1.62 qnt [7.2] | — | 1.00-1.36 m | 0.88 [6.4] |
| 21AbO | 2.23 dt [7.4; 7.4; 16.1] | 2.07 dt [7.4; 7.4; 16.1] | 2.37 t [7.4] | 1.42 qnt [7.4] | 1.63 qnt [7.4] | 5.28-5.42 m | 1.20-1.38 m | 0.88 [6.7] |
| 25AbP | | 2.26 t [7.4] | | 1.50 m | | — | 1.00-1.40 m | 0.88 [6.7] |
| 25AbS | | 2.26 t [7.4] | | 1.50 m | | — | 1.00-1.40 m | 0.88 [6.3] |
| 25AbO | | 2.26 dt [1.5; 7.4] | | 1.50 m | | 5.27-5.42 m | 1.03-1.42 m | 0.88 [6.7] |

TABLE 6

Chemical Shifts (δ, ppm) in ¹³C-NMR Spectra (75 MHz) in different solvents of pyridinio lipids of type 21 and 25 (in CDCl₃); assignments are given by means of signal intensity, APT and HETCOR (¹H-¹³C)

| Comp | C=O 2-CO | C=O 3-CO | C(Py⁺) γ | C(Py⁺) α | C(Py⁺) (α') | C(Py⁺) β | C(Py⁺) (β') | CH | CH₂ 3-CH₂ | CH₂ 1-CH₂ | OCOCH₂ 2-OCOCH₂ Hₐ | OCOCH₂ 2-OCOCH₂ Hᵦ | OCOCH₂ 3-OCOCH₂ |
|---|---|---|---|---|---|---|---|---|---|---|---|---|---|
| 21AaP | 173.06 | 172.38 | 158.58 | 155.55 | | 128.61 | | 68.39 | 62.36 | 51.97 | 33.86 | | 33.65 |
| 21AaS | 173.05 | 172.36 | 158.59 | 155.53 | | 128.62 | | 68.38 | 62.36 | 51.93 | 33.85 | | 33.63 |
| 21AaO | 173.07 | 172.38 | 158.60 | 155.54 | | 128.62 | | 68.42 | 62.39 | 51.99 | 33.87 | 33.83 | 33.63 |
| 25AaP | 173.16 | | 159.60 | 155.94 | 155.00 | 131.18 | 129.34 | 63.63 | 61.60 | | 33.62 | | |
| 25AaS | 173.14 | | 159.63 | 155.94 | 154.97 | 131.11 | 129.33 | 63.64 | 61.65 | | 33.59 | | |
| 25AaO | 173.20 | | 159.59 | 155.93 | 154.96 | 131.14 | 129.34 | 63.64 | 61.61 | | 34.07 | 33.95 | 33.63 |
| 21AbP | 173.08 | 172.38 | 158.55 | 155.59 | | 128.51 | | 68.42 | 62.35 | 51.76 | 33.85 | | 33.64 |
| 21AbS | 173.07 | 172.38 | 158.58 | 155.58 | | 128.53 | | 68.40 | 62.35 | 51.73 | 33.85 | | 33.63 |
| 21AbO | 173.07 | 172.38 | 158.48 | 155.62 | | 128.49 | | 68.47 | 62.38 | 51.89 | 34.05 | 33.81 | 33.61 |
| 25AbP | 173.16 | | 159.60 | 155.96 | 155.05 | 131.08 | 129.25 | 63.63 | 61.53 | | 33.60 | | |

TABLE 6-continued

Chemical Shifts (δ, ppm) in $^{13}$C-NMR Spectra (75 MHz) in different solvents of pyridinio lipids of type 21 and 25 (in CDCl$_3$); assignments are given by means of signal intensity, APT and HETCOR ($^1$H-$^{13}$C)

| | | | | | | | | | |
|---|---|---|---|---|---|---|---|---|---|
| 25AbS | 173.21 | 159.40 | 156.03 | 155.28 | 131.11 | 129.26 | 63.80 | 61.70 | 33.66 |
| 25AbO | 173.18 | 159.36 | 156.09 | 155.28 | 131.13 | 129.30 | 63.84 | 61.66 | 33.64 |

| | OCOCH$_2$CH$_2$ | | | | | | | CH$_3$ from Py$^+$ | | |
|---|---|---|---|---|---|---|---|---|---|---|
| | 2-OCOCH$_2$<u>CH$_2$</u> | | 3- | | | | | | | |
| Comp | H$_A$ | H$_B$ | OCOCH$_2$<u>CH$_2$</u> | CH=CH | (CH$_2$)n | <u>CH$_2$</u>CH$_3$ | CH$_3$ | α | (α') | γ |
| 21AaP | 22.74 | | 24.52 | — | 31.88, 29.68, 29.66, 29.63, 29.58, 29.48, 29.43, 29.33, 29.28, 29.18, 29.10, 28.89 | 22.65 | 14.08 | 21.63 | | 21.75 |
| 21AaS | 24.73 | | 24.51 | — | 31.87, 29.65-29.60 m, 29.46, 29.42, 29.31, 29.27, 29.17, 29.08, 28.86 | 22.64 | 14.06 | 21.60 | | 21.73 |
| 21AaO | 24.72 | 24.65 | 24.50 | 130.11, 129.98, 129.68, 129.48 | 31.87, 29.72, 29.66, 29.64, 29.48, 29.42, 29.28, 29.18, 29.10, 29.03, 28.94 | 22.64 | 14.08 | 21.64 | | 21.73 |
| 25AaP | 24.59 | | | | 31.88, 29.66, 29.62, 29.59, 29.44, 29.32, 29.22, 28.99 | 22.65 | 14.08 | 23.10 | 22.33 | 21.54 |
| 25AaS | 24.55 | | | | 31.84, 29.68-29.38 m, 29.28, 29.16, 29.10, 29.01, 28.94, 28.77 | 22.61 | 14.03 | 23.13 | 22.38 | 21.54 |
| 25AaO | 24.91 | 24.70 | 24.58 | 130.04, 129.96, 129.69, 129.59 | 31.86, 29.73, 29.65, 29.56, 29.48, 29.42, 29.28, 29.18, 29.12, 29.05, 28.95 | 22.64 | 14.08 | 23.14 | 22.39 | 21.59 |
| 21AbP | 24.75 | | 24.53 | | 31.89, 29.68, 29.66, 29.63, 29.58, 29.48, 29.43, 29.33, 29.28, 29.19, 29.11, 28.88 | 22.65 | 14.08 | 21.54 | | |
| 21AbS | 24.74 | | 24.52 | | 31.88, 29.68-29.58 m, 29.47, 29.42, 29.31, 29.27, 29.17, 29.09, 28.87 | 22.64 | 14.07 | 21.54 | | |
| 21AbO | 24.72 | 24.49 | 24.49 | 130.09, 129.95, 129.68, 129.47 | 31.85, 29.78-29.50 m, 29.47 m, 29.26, 29.18, 29.12, 29.04, 28.94 | 22.63 | 14.06 | 21.55 | | 21.61 |
| 25AbP | 24.59 | | | | 31.88, 29.66, 29.63, 29.59, 29.44, 29.32, 29.21, 28.99 | 22.65 | 14.07 | 22.94 | 22.16 | 21.45 |
| 25AbS | 24.59 | | | | 31.86, 29.63 m, 29.41, 29.30, 29.18, 29.14, 28.98 | 22.62 | 14.05 | 23.29 | | 21.61 |
| 25AbO | 24.58 | | | 130.04, 129.90, 129.70, 129.55 | 31.85, 29.70, 29.64, 29.47, 29.40, 29.27, 29.13, 29.08, 29.02, 28.94 | 22.63 | 14.06 | 23.34 | | 21.62 |

What is claimed is:

1. A compound useful as a gene transfer agent, the compound having Formula I:

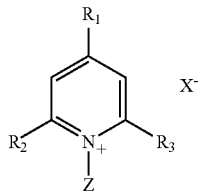

Formula I wherein $R^1$ is selected from the group consisting of $C_{1-25}$ alkyl; $C_{2-25}$ alkenyl; $C_{2-25}$ alkynyl; $C_{1-25}$ alkoxy; $C_{1-25}$ alkylaminomethyl; $C_{1-25}$ dialkylaminomethyl; phenyl; phenyl substituted with one or more substitutents selected from the group consisting of $C_{1-5}$ alkyl, $C_{2-5}$ alkenyl, $C_{2-5}$ alkynyl, $C_{1-5}$ alkoxy, and $C_{1-5}$ amino; styryl; and styryl substituted with one or more substitutents selected from the group consisting of $C_{1-25}$ alkyl, $C_{2-25}$ alkenyl; $C_{2-25}$ alkynyl, $C_{1-25}$ alkoxy, and $C_{1-25}$ dialkylamino;

$R^2$ and $R^3$ are $C_{1-25}$ alkyl, $C_{2-25}$ alkenyl; or $C_{2-25}$ alkynyl;

wherein X is selected from the group consisting of halogen, perchlorate, tetrafluoroborate, trifluoromethanesulfonate, methanesulfonate, p-toluenesulfonate, methosulfate, sulfoacetate, acetate, trifluoroacetate, hemisuccinate and hexafluorophosphate, and wherein Z is

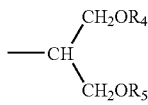

wherein $R_4$ and $R_5$ are independently selected from the group consisting of $C_{1-25}$ alkyl, $C_{2-25}$ alkenyl; $C_{2-25}$ alkynyl; $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl.

2. The compound of claim 1, wherein said Formula I is 1-(1,3-dimyristoyloxypropane-2-yl)-2,4,6-trimethylpyridinium hexafluorophosphate.

3. The compound of claim 1, wherein Formula I is selected from the group of compounds consisting of 1-(2,3-dihydroxypropyl)-2,4,6-trimethylpyridinium hexafluorophosphate, 1-(2,3-dilauroyloxypropyl)-2,4,6-trimethylpyridinium hexafluorophosphate, 1-(2,3-dimyristoyloxypropyl)-2,4,6-trimethylpyddinium hexafluorophosphate, 1-(2,3-dipamitoyloxypropyl)-2,4,6-trimethylpyridinium hexafluorophosphate, 1-(2,3-distearoyloxypropyl)-2,4,6-trimethylpyridinium hexafluorophosphate, 1-(2,3-dioleoyloxypropyl)-2,4,6-trimethylpyridinium hexafluorophosphate, 1-(1,3-dihydroxypropane-2-yl)-2,4,6-trimethylpyridinium hexafluorophosphate, 1-(1,3-dilauroyloxypropane-2-yl)-2,4,6-trimethylpyridinium hexafluorophosphate, 1-(1,3-dimyristoyloxypropane-2-yl)-2,4,6-trimethylpyridinium hexafluorophosphate, 1-(1,3-dimyristoyloxypropane-2-yl)-2,4,6-trimethylpyridinium perchlorate, 1-(1,3-dimyristoyloxypropane-2-yl)-2,4,6-trimethylpyridinium tetrafluoroborate, 1-(1,3-dimyristoyloxypropane-2-yl)-2,4,6-trimethylpyridinium chloride, 1-(1,3-dimyristoyloxypropane-2-yl)-2,4,6-trimethylpyridinium iodide, 1-(1,3-dipamitoyloxypropane-2-yl)-2,4,6-trimethylpyridinium hexafluorophosphate, 1-(1,3-distearoyloxypropane-2-yl)-2,4,6-trimethylpyridinium hexafluorophosphate, 1-(1,3-dioleoyloxypropane-2-yl)-2,4,6-trimethylpyridinium hexafluorophosphate, 1-(3,4-dihydroxyphenylethyl)-2,4,6-trimethylpyridinium hexafluorophosphate, 1-(3,4-dioctanoyloxyphenylethyl)-2,4,6-trimethylpyridinium hexafluorophosphate, 1-(3,4-didecanoyloxyphenylethyl)-2,4,6-trimethylpyridinium hexafluorophosphate, 1-(3,4-dilauroyloxyphenylethyl)-2,4,6-trimethylpyridinium hexafluorophosphate, 1-(3,4-dimyristoyloxyphenylethyl)-2,4,6-trimethylpyridinium hexafluorophosphate, 1-(3,4-dipalmitoyloxyphenylethyl)-2,4,6-trimethylpyridinium hexafluorophosphate, 1-(3,4-distearoyloxyphenylethyl)-2,4,6-trimethylpyridinium hexafluorophosphate, and 1-(3,4-dioleoyloxyphenylethyl)-2,4,6-trimethylpyridinium hexafluorophosphate.

4. A method of preparing a compound according to claim 1, the method comprising: reacting a compound having the formula:

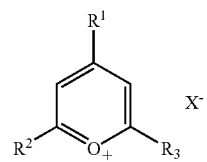

Formula II wherein $R^1$ is selected from the group consisting of $C_{1-25}$ alkyl; halogeno $C_{1-25}$ alkyl, $C_{2-25}$ alkenyl; $C_{2-25}$ alkynyl; $C_{1-25}$ alkoxy; $C_{1-25}$ alkylaminomethyl; $C_{1-25}$ dialkylaminomethyl; phenyl; phenyl substituted with one or more substitutents selected from the group consisting of $C_{1-5}$ alkyl, $C_{2-5}$ alkenyl, $C_{2-5}$ alkynyl, $C_{1-5}$ alkoxy, and $C_{1-5}$ amino; styryl; and styryl substituted with one or more substitutents selected from the group consisting of $C_{1-25}$ alkyl, $C_{2-25}$ alkenyl, $C_{2-25}$ alkynyl, $C_{1-25}$ alkoxy, and $C_{1-25}$ dialkylamino;

$R^2$ and $R^3$ are $C_{1-25}$ alkyl, $C_{2-25}$ alkenyl; $C_{2-25}$ alkynyl;

wherein X is selected from the group consisting of halogen, perchlorate, tetrafluoroborate, trifluoromethanesulfonate, sulfoacetate, and hexafluorophosphate; with a primary amine.

5. The method of claim 4, wherein the primary amine contains one or more hydroxyl groups and wherein the method further comprises alkylating or acylating the one or more hydroxyl groups.

6. The method of claim 4, wherein the primary amine is selected from the group consisting of:

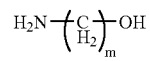

wherein m is 1-25

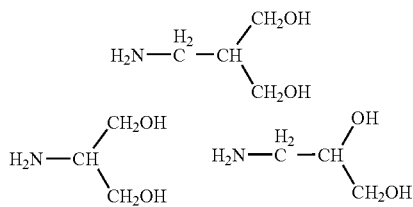

-continued

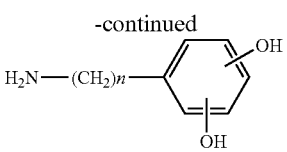

wherein n is 0-25, and

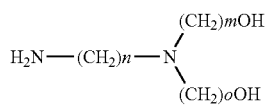

wherein n, m, and o are independently 0-25,
and wherein the method further comprises acylating the one or more hydroxyl groups with an acylhalide having the formula $R_4C(O)X$, wherein $R_4$ is selected from the group consisting of $C_{1-25}$ alkyl, $C_{2-25}$ alkenyl; $C_{2-25}$ alkynyl, $C_{1-25}$ acyl, perfluoro $C_{1-25}$ alkyl; perfluoro $C_{1-25}$ acyl; poly(ethyleneoxy)alkyl, poly(ethyleneoxy)acyl, and cholesteryloxycarbonyl.

7. The method of claim 4, wherein the primary amine comprises one or more hydroxyl groups and the method further comprises forming the tosylate or trifluoromethanesulfonate ester of the one or more hydroxyl groups and reacting the tosylate or trifluoromethanesulfonate ester with an alcohol having the formula $R_4OH$, wherein $R_4$ is selected from the group consisting of $C_{1-25}$ alkyl, $C_{2-25}$ alkenyl; $C_{2-25}$ alkynyl, perfluoro $C_{1-25}$ alkyl, poly(ethyleneoxy)alkyl, in the presence of a strong base such as potassium t-butoxide or sodium hydride.

8. The method of claim 4, wherein the primary amine contains two or more primary amine groups.

9. The method of claim 4, wherein two equivalents of a compound having Formula II are reacted with a primary amine having two amine groups.

10. The method of claim 4, wherein two equivalents of a compound having Formula II are reacted with a primary amine having the formula $NH_2(CH_2)mNH_2$, wherein m is 0-25, to yield a compound having the formula

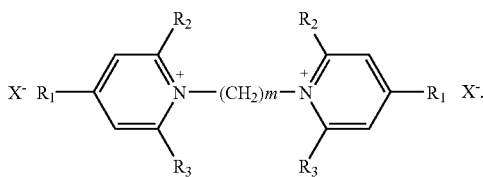

11. The method of claim 4, wherein two equivalents of a compound having Formula II are reacted with a primary amine having the formula $NH_2[(CH_2)_mNH]_k(CH_2)_oNH_2$, wherein m, k, and o are independently 0-25, to yield a compound having the formula

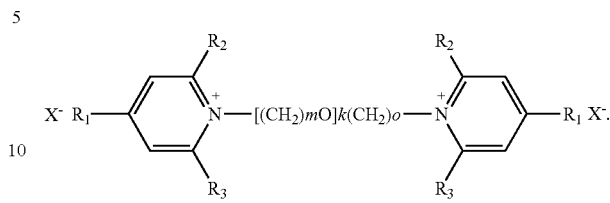

12. The method of claim 4, wherein two equivalents of a compound having Formula II are reacted with a compound having the formula $NH_2[(CH_2)_mN(R_9)]_k(CH_2)_oNH_2$, wherein m, k, and o are independently 0-25 and R9 is selected from the group consisting of $C_{1-25}$ alkyl, hydroxy $C_{1-25}$ alkyl, amino $C_{1-25}$ alkyl, $C_{2-25}$ alkenyl; $C_{2-25}$ alkynyl, $C_{1-25}$ acyl, hydroxy $C_{1-25}$ acyl, amino $C_{1-25}$ acyl, $C_{1-25}$ alkyloxycarbonyl, t-butyloxycarbonyl, adamantyloxycarbonyl, perfluoro $C_{1-25}$ alkyl; perfluoro $C_{1-25}$ acyl; poly(ethyleneoxy)alkyl, poly(ethyleneoxy)acyl, and cholesteryloxycarbonyl, to yield a compound having the formula

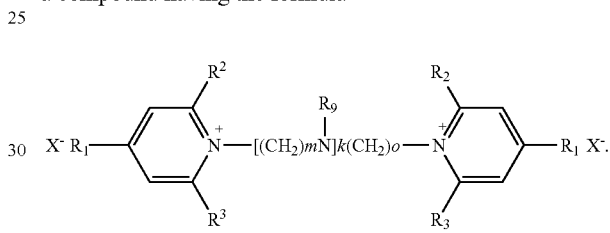

13. A method of transfecting eukaryotic cells comprising mixing at least one plasmid or polynucleotide with the compound of claim 1.

14. The method of claim 13, wherein said at least one plasmid or polynucleotide is selected from the group consisting of DNA, RNA, oligonucleotides, and truncated oligonucleotides.

15. The method of claim 13, further comprising mixing a helper lipid with the mixture of said at least one plasmid or polynucleotide and said compound, wherein said helper lipid is cholesterol or dioleolyphosphatidylethanolamine.

16. The method of claim 15, wherein the ratio of said compound to said helper lipid is about 1.0:0.1 to about 1.0:1.5.

* * * * *